United States Patent
Ramanan et al.

(10) Patent No.: US 9,687,177 B2
(45) Date of Patent: Jun. 27, 2017

(54) DETECTION OF SLEEP CONDITION

(75) Inventors: Dinesh Ramanan, Telopea (AU); Jeffrey Peter Armitstead, North Sydney (AU)

(73) Assignee: ResMed Limited (AU)

( * ) Notice: Subject to any disclaimer, the term of this patent is extended or adjusted under 35 U.S.C. 154(b) by 1271 days.

(21) Appl. No.: 13/383,341

(22) PCT Filed: Jul. 14, 2010

(86) PCT No.: PCT/AU2010/000894
§ 371 (c)(1),
(2), (4) Date: Mar. 28, 2012

(87) PCT Pub. No.: WO2011/006199
PCT Pub. Date: Jan. 20, 2011

(65) Prior Publication Data
US 2012/0179061 A1  Jul. 12, 2012

Related U.S. Application Data

(60) Provisional application No. 61/226,069, filed on Jul. 16, 2009.

(51) Int. Cl.
*A61B 5/08* (2006.01)
*A61B 5/087* (2006.01)
(Continued)

(52) U.S. Cl.
CPC .......... *A61B 5/087* (2013.01); *A61B 5/02405* (2013.01); *A61B 5/4809* (2013.01);
(Continued)

(58) Field of Classification Search
USPC .................................... 600/538; 128/201.23
See application file for complete search history.

(56) References Cited

U.S. PATENT DOCUMENTS 5,101,831 A   4/1992 Koyama et al.
5,280,791 A   1/1994 Lavie
(Continued)

FOREIGN PATENT DOCUMENTS

CN   1713850 A    12/2005
EP   2000090 A2   12/2008
(Continued)

OTHER PUBLICATIONS

Aittokallio, Tero, et al. "Analysis of inspiratory flow shapes in patients with partial upper-airway obstruction during sleep." Chest Journal 119.1 (2001): 37-44.*
(Continued)

*Primary Examiner* — Michael Kahelin
*Assistant Examiner* — Mitchell E Alter
(74) *Attorney, Agent, or Firm* — Lerner, David, Littenberg, Krumholz & Mentlik, LLP

(57) ABSTRACT

Automated devices provide methodologies for determining sleep conditions, which may be in conjunction with treatment of sleep disordered breathing by a pressure treatment apparatus such as a continuous positive airway pressure device. Based on a measure of respiratory airflow, respiratory characteristics are extracted to detect arousal conditions, sleep stability, sleep states and/or perform sleep quality assessments. The methodologies may be implemented for data analysis by a specific purpose computer, a monitoring device that measures a respiratory airflow and/or a respiratory treatment apparatus that provides a respiratory treatment regime based on the detected conditions.

33 Claims, 32 Drawing Sheets

(51) Int. Cl.
  *A61B 5/024* (2006.01)
  *A61B 5/00* (2006.01)
  *A61M 16/00* (2006.01)
  *A61B 5/0205* (2006.01)
  *A61M 16/06* (2006.01)

(52) U.S. Cl.
  CPC .......... *A61B 5/4812* (2013.01); *A61B 5/4815* (2013.01); *A61B 5/4818* (2013.01); *A61B 5/7475* (2013.01); *A61M 16/0051* (2013.01); *A61M 16/0069* (2014.02); *A61B 5/0205* (2013.01); *A61B 5/0871* (2013.01); *A61B 5/7267* (2013.01); *A61M 16/0066* (2013.01); *A61M 16/0666* (2013.01); *A61M 2016/0027* (2013.01); *A61M 2016/0036* (2013.01); *A61M 2205/15* (2013.01); *A61M 2205/50* (2013.01); *A61M 2205/502* (2013.01); *A61M 2205/52* (2013.01)

(56) References Cited

U.S. PATENT DOCUMENTS

| | | |
|---|---|---|
| 5,485,851 A | 1/1996 | Erickson |
| 5,704,345 A | 1/1998 | Berthon-Jones |
| 6,029,665 A | 2/2000 | Berthon-Jones |
| 6,138,675 A | 10/2000 | Berthon-Jones |
| 6,152,129 A | 11/2000 | Berthon-Jones |
| 6,345,619 B1 | 2/2002 | Finn |
| 6,532,957 B2 | 3/2003 | Berthon-Jones |
| 6,675,797 B1 | 1/2004 | Berthon-Jones |
| 7,128,069 B2 | 10/2006 | Farrugia et al. |
| 7,276,031 B2 | 10/2007 | Norman et al. |
| 2002/0014240 A1 | 2/2002 | Truschel |
| 2002/0185131 A1* | 12/2002 | Madaus et al. .......... 128/204.26 |
| 2002/0193839 A1 | 12/2002 | Cho et al. |
| 2004/0111041 A1 | 6/2004 | Ni et al. |
| 2005/0020932 A1 | 1/2005 | Haberland et al. |
| 2005/0038353 A1 | 2/2005 | Rapoport et al. |
| 2005/0042589 A1 | 2/2005 | Hatlestad et al. |
| 2005/0080349 A1 | 4/2005 | Okada et al. |
| 2005/0209513 A1 | 9/2005 | Heruth et al. |
| 2005/0267362 A1 | 12/2005 | Mietus et al. |
| 2006/0000475 A1 | 1/2006 | Matthews et al. |
| 2006/0070624 A1 | 4/2006 | Kane et al. |
| 2006/0070625 A1 | 4/2006 | Ayappa et al. |
| 2006/0102179 A1 | 5/2006 | Rapoport et al. |
| 2006/0270941 A1 | 11/2006 | Xie et al. |
| 2007/0089745 A1 | 4/2007 | Gabriel et al. |
| 2007/0208269 A1 | 9/2007 | Mumford et al. |
| 2007/0276278 A1 | 11/2007 | Coyle et al. |
| 2008/0045813 A1 | 2/2008 | Phuah et al. |
| 2008/0306351 A1 | 12/2008 | Izumi |
| 2009/0038616 A1 | 2/2009 | Mulcahy et al. |
| 2009/0306530 A1 | 12/2009 | Platt |
| 2010/0131028 A1 | 5/2010 | Hsu et al. |
| 2010/0152546 A1 | 6/2010 | Behan et al. |
| 2011/0203588 A1* | 8/2011 | Armitstead et al. ..... 128/204.21 |

FOREIGN PATENT DOCUMENTS

| | | |
|---|---|---|
| JP | 2005342188 A | 12/2005 |
| WO | 9716216 A1 | 5/1997 |
| WO | 02/28281 A1 | 4/2002 |
| WO | 2004032719 A2 | 4/2004 |
| WO | 2004/112680 A2 | 12/2004 |
| WO | 2005051470 A1 | 6/2005 |
| WO | 2008037020 A1 | 4/2008 |
| WO | 2008/138040 A1 | 11/2008 |
| WO | 2009002238 A1 | 12/2008 |

OTHER PUBLICATIONS

Hudgel, David W., et al. "Mechanics of the respiratory system and breathing pattern during sleep in normal humans." Journal of Applied Physiology 56.1 (1984): 133-137.*

Ayappa, Indu, et al. "Irregular respiration as a marker of wakefulness during titration of CPAP." Sleep 32.1 (2009): 99.*

Ayappa et al., P391 Automated detection of irregular respiration: A marker of wakefulness, Abstract/Sleep Medicine 7 (2006) S1-S127, pp. S83-S84.

SensAwake Sensitive to Sleep, Fisher & Paykel Healthcare.

Ayappa, et al., Respiration During CPAP Titration, Irregular Respiration as a Marker of Wakefulness During Titration of CPAP, Sleep, vol. 32, No. 1, 2009.

International Search Report and Written Opinion, PCT/AU10/00894, dated Dec. 2, 2010.

Extended European Search Report for Application No. EP10799282 dated Aug. 13, 2014.

* cited by examiner

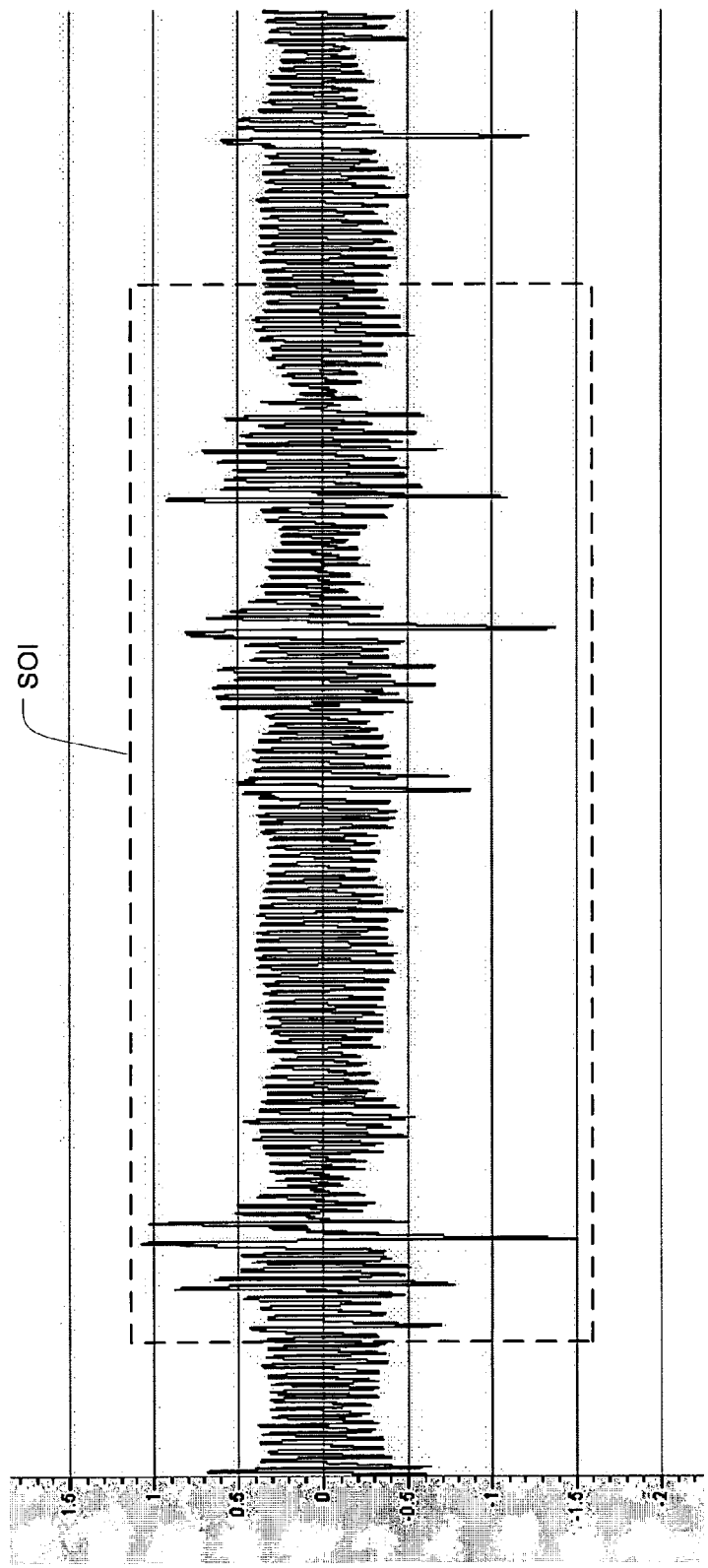
FIG. 23-A

IPFV

| 2540A | IA (<=0.001) | IB (<=0.003) | IC (<=0.009) | ID (<=10) |
|---|---|---|---|---|
| O_Awake | OA=0.05 | OB=0.1 | OC=0.25 | OD=0.7 |
| O_NREM | OA=0.85 | OB=0.8 | OC=0.25 | OD=0.1 |
| O_REM | OA=0.1 | OB=0.1 | OC=0.5 | OD=0.2 |

EPFV

| 2540B | IA (<=0.001) | IB (<=0.003) | IC (<=0.009) | ID (<=10) |
|---|---|---|---|---|
| O_Awake | OA=0.05 | OB=0.1 | OC=0.25 | OD=0.7 |
| O_NREM | OA=0.85 | OB=0.8 | OC=0.25 | OD=0.1 |
| O_REM | OA=0.1 | OB=0.1 | OC=0.5 | OD=0.2 |

TSLBV

| 2540C | IA (<=0.001) | IB (<=0.003) | IC (<=0.009) | ID (<=10) |
|---|---|---|---|---|
| O_Awake | OA=0.05 | OB=0.1 | OC=0.25 | OD=0.7 |
| O_NREM | OA=0.85 | OB=0.8 | OC=0.25 | OD=0.1 |
| O_REM | OA=0.1 | OB=0.1 | OC=0.5 | OD=0.2 |

I75AV

| 2540D | IA (<=0.001) | IB (<=0.003) | IC (<=0.009) | ID (<=10) |
|---|---|---|---|---|
| O_Awake | OA=0.1 | OB=0.1 | OC=0.05 | n/a |
| O_NREM | OA=0.8 | OB=0.6 | OC=0.75 | n/a |
| O_REM | OA=0.1 | OB=0.3 | OC=0.2 | n/a |

FIG. 25

TABLE 2600A

| State = Awake | RULE 1 | RULE 2 | RULE 3 | RULE 4 | RULE 5 | RULE 6 | RULE 7 | RULE 8 |
|---|---|---|---|---|---|---|---|---|
| T11 | 1 | 0.9 | 0.45 | 1 | 0.9 | 0.45 | 0.6 | 0.45 |
| T13 | 0 | 0.1 | 0.45 | 0 | 0.05 | 0.45 | 0.3 | 0.45 |
| T14 | 0 | 0.1 | 0.1 | 0 | 0.05 | 0.1 | 0.1 | 0.1 |

TABLE 2600B

| State = NREM | RULE 9 | RULE 10 | RULE 11 | RULE 12 |
|---|---|---|---|---|
| T31 | 0.7 | 0.2 | 0.25 | 0.3 |
| T33 | 0.25 | 0.7 | 0.5 | 0.4 |
| T34 | 0.05 | 0.1 | 0.25 | 0.3 |

TABLE 2600C

| State = REM | RULE 13 | RULE 14 | RULE 15 |
|---|---|---|---|
| T41 | 0.3 | 0.3 | 0.4 |
| T43 | 0.2 | 0.3 | 0.2 |
| T44 | 0.5 | 0.4 | 0.4 |

FIG. 26

TABLE 2700A

| State = Awake | RULE 1 | RULE 2 | RULE 3 |
|---|---|---|---|
| T12 | 0 | 0 | 1 |

TABLE 2700B

| State = NREM Sleep | RULE 4 | RULE 5 | RULE 6 | RULE 7 | RULE 8 |
|---|---|---|---|---|---|
| T32 | 0 | 0 | 1 | 1 | 1 |

TABLE 2700C

| State = NREM Sleep T | RULE 9 | RULE 10 | RULE 11 | RULE 12 | RULE 13 |
|---|---|---|---|---|---|
| T21 | 1 | 0 | 1 | 0 | 0 |
| T22 | 0 | 1 | 0 | 1 | 1 |
| T23 | 1 | 0 | 0 | 0 | 0 |
| T24 | 1 | 0 | 0 | 0 | 0 |

TABLE 2700D

| State = REM | RULE 14 | RULE 15 | RULE 16 |
|---|---|---|---|
| T42 | 0 | 0 | 1 |

FIG. 27

DETECTION OF SLEEP CONDITION

CROSS-REFERENCE TO RELATED APPLICATIONS

The present application is a national phase entry under 35 U.S.C. §371 of International Application No. PCT/AU2010/000894 filed Jul. 14, 2010, published in English, which claims priority from U.S. Provisional Patent Application No. 61/226,069 filed Jul. 16, 2009. The disclosures of said applications are incorporated by reference herein.

FIELD OF THE TECHNOLOGY

The present technology relates to methods and apparatus for detection of a condition of sleep and related characteristics.

BACKGROUND OF THE TECHNOLOGY

Patients with OSA may experience recurrent apnoeas or hypopnoeas during sleep that are only terminated by the patient arousing. These recurrent respiratory dysfunction events cause sleep fragmentation and stimulation of the sympathetic nervous system. This can have severe consequences for the patient including day-time sleepiness (with the attendant possibility of motor-vehicle accidents), poor mentation, memory problems, depression and hypertension. Patients with OSA are also likely to snore loudly, thus also disturbing their partner's sleep.

Patients may also experience other events that may interrupt sleep. For example, Periodic Limb Movement (PLM) is a repeated cramping or spasm of the legs during sleep. These leg movement events may be considered a sleep disorder when they disrupt sleep and lead to daytime sleepiness.

Patients with OSA are typically treated with constant positive airway pressure (CPAP). The positive pressure prevents collapse of the patient's airway during inspiration, thus preventing recurrent respiratory system events (e.g., apnoeas or hypopnoeas) and their sequelae. Such a respiratory treatment apparatus can function to supply the patient with a supply of clean breathable gas (usually air, with or without supplemental oxygen) at the therapeutic pressure or pressures, at appropriate times during the subject's breathing cycle.

Respiratory treatment apparatus typically include a flow generator, an air filter, a mask or cannula, an air delivery conduit connecting the flow generator to the mask, various sensors and a microprocessor-based controller. The flow generator may include a servo-controlled motor and an impeller. The flow generator may also include a valve capable of discharging air to atmosphere as a means for altering the pressure delivered to the patient as an alternative to motor speed control. The sensors measure, amongst other things, motor speed, gas volumetric flow rate and outlet pressure, such as with a pressure transducer, flow sensor or the like. The apparatus may optionally include a humidifier and/or heater elements in the path of the air delivery circuit. The controller may include data storage capacity with or without integrated data retrieval/transfer and display functions.

While these devices may typically be configured to detect sleep disordered breathing events of the apnea or hypopnea type, they do not usually provide more detailed information to the user about sleep. Thus, it may be desirable to develop methods and apparatus for detecting these and other conditions of sleep to more completely assess sleep quality.

SUMMARY OF THE TECHNOLOGY

A first aspect of some embodiments of the present technology is to provide methods and devices to detect sleep quality.

Another aspect of some embodiments of the present technology is to provide methods and devices to detect sleep state.

A further aspect of some embodiments of the present technology is to provide methods and devices to detect sleep stability.

A still further aspect of some embodiments of the present technology is to provide methods and devices to detect arousal from sleep.

Some embodiments include a method for controlling a processor to detect a sleep state from a measured flow of breathable gas. The method of the processor may involve determining a plurality of respiratory characteristics from a measure of respiratory flow. It may also involve detecting a state from potential sleep states comprising a Non-REM sleep state and a REM sleep state. The detecting of the state may be based on the determined respiratory characteristics. The processor may then indicate the detected state.

In some embodiments, the potential sleep states may further include an awake state. Similarly, the REM sleep state may be a light REM state and the potential sleep states may also include a deep REM state.

In some embodiments, the processor determines the detected state by calculating probabilities representative of transitions between each potential sleep state with data from the plurality of respiratory characteristics, and determines the detected state as a function of a most probable one of the calculated probabilities. Optionally, the plurality of respiratory characteristics may include one or more of a measure of inspiratory peak flow variation, a measure of expiratory peak flow variation, a measure of a ratio of an expiratory peak flow location and expiratory time, a measure of an expiratory peak flow location variation, a measure of an area of an expiratory peak flow, a measure of an area of an expiratory peak flow variation, a measure of a time from expiratory peak flow to inspiration start, a measure of a time since last confirmed breath variability, a measure of a high breath frequency period, and a measure of inspiratory time variability.

One or more of the aforementioned methods may be implemented as a sleep state detection apparatus including a controller configured with the method(s). The controller may optionally be coupled with a flow sensor to measure the flow of breathable gas. The controller may then also include a processer controlled flow generator to provide a controlled respiratory pressure treatment regime based on the detected state.

Some embodiments of the present technology may include method for controlling a processor to classify a sleep arousal condition from a measured flow of breathable gas. The method of the processor may include determining a plurality of respiratory characteristics from a measure of respiratory flow. The processor may detect a disturbance from the plurality of respiratory characteristics. The disturbance may be indicative of an arousal condition. The processor may then assess whether the disturbance is a non-respiratory related arousal. The processor may then indicate that the detected disturbance represents an arousal based from an event other than a symptom of respiratory dysfunction.

In some embodiments, the assessment may involve determining a measure indicative of respiratory flow limitation, such as flow flattening detection. The assessing may also involve detecting an absence of respiratory flow limitation. In some such embodiments, the plurality of respiratory characteristics may include one or more of a measure of time to reach a proportion of inspiratory peak flow, a measure of area above a proportion of inspiratory peak flow, a measure of area above a proportion of inspiratory peak flow variation, and a measure of time between a proportion of inspiratory peak flow and expiratory peak flow. Optionally, the aforementioned assessing of whether the disturbance is a non-respiratory related arousal may be based on a detection of a sleep state. The assessing may also involve detecting mask leak so that an arousal due to mask leak may be detected.

One or more of the aforementioned methods may be implemented as a sleep arousal state classifying apparatus including a controller configured with the method(s). The controller may optionally be coupled with a flow sensor to measure the flow of breathable gas. The controller may then also include a processer controlled flow generator to provide a controlled respiratory pressure treatment regime based on the detected sleep arousal state.

In still further embodiments, a method may be implemented to control a processor in assessing sleep stability from a measured flow of breathable gas. The method of the processor may include determining a plurality of respiratory characteristics from a measure of respiratory flow. The method may also include detecting a disturbance from the plurality of respiratory characteristics, the disturbance indicative of an arousal condition. The method may also include determining a degree of the disturbance. The degree may be indicative of an extent to which the arousal condition has interrupted sleep. The processor may then indicate the degree of the disturbance.

In some embodiments, the determining of the degree of disturbance may involve calculating a ratio of a respiratory characteristic attributable to the disturbance with a common respiratory characteristic attributable to flow data prior to an occurrence of the disturbance. In such an example, the flow data may represent a plurality of breathing cycles. In some examples of this embodiment, the respiratory characteristic(s) attributable to the disturbance may be at least one of a measure of time to reach a proportion of inspiratory peak flow, a measure of area above a proportion of inspiratory peak flow, a measure of area above a proportion of inspiratory peak flow variation, and a measure of time between a proportion of inspiratory peak flow and expiratory peak flow.

Optionally, a determination of the degree of disturbance may involve calculating an average of ratios of a variance of a plurality of respiratory characteristics attributable to the disturbance with a variance of a common plurality of respiratory characteristics attributable to flow data prior to an occurrence of the disturbance where the flow data represents a plurality of breathing cycles.

Moreover, in some embodiments the method of the processor may further involve determining a level of autonomic activation from the determined degree of the disturbance and patient characteristic data. For example, the autonomic activation may include a data value of a heart rate variability and/or a data value of a pulse transit time. Thus, the determining of the level of autonomic activation may involve selecting at least one of a heart rate variability value and a pulse transit time value. This selecting may include accessing a data structure indexed by the determined degree of disturbance and the patient characteristic data, such as a patient age and a patient weight.

One or more of the aforementioned methods may be implemented as a sleep stability assessment apparatus including a controller configured with the method(s). The controller may optionally be coupled with a flow sensor to measure the flow of breathable gas. The controller may then also include a processer controlled flow generator to provide a controlled respiratory pressure treatment regime based on the assessed sleep stability.

In some embodiments of the present technology, a method for controlling a processor determines a sleep quality indicator from a measured flow of breathable gas. In the method, processor determines a plurality of respiratory characteristics from a measure of respiratory flow. It also determines a sleep state measure and a sleep stability from the plurality of respiratory characteristics. It then determines and indicates a sleep quality index from the sleep state measure and the stability measure.

The sleep quality index may be derived by the processor with a ratio of a determined sleep time of a treatment session and the sleep stability measure. In some embodiments, the sleep quality index may be derived as a function of a ratio of sleep time during a treatment session and the sleep stability measure. The sleep quality index may also be derived as a function of a duration of awake periods during the treatment session. In some embodiments, the sleep state measure may include at least one of a REM state, a non-REM state and an awake state and a measure of duration for the sleep state measure. Moreover, the sleep stability measure may be derived as a function of a determined flow disturbance and flow data preceding the flow disturbance. In addition, the determination of the sleep stability measure may include detecting an arousal from sleep based on the flow disturbance.

One or more of the aforementioned methods may be implemented as a sleep quality detection apparatus including a controller configured with the method(s). The controller may optionally be coupled with a flow sensor to measure the flow of breathable gas. The controller may then also include a processer controlled flow generator to provide a controlled respiratory pressure treatment regime based on the detected sleep quality.

Still further embodiments of the present technology may involve a method for detecting periodic breathing. The method may include determining a set of respiratory features from a measure of respiratory flow. It may further include thresholding the set of respiratory features. It may further include detecting a periodic breathing state based on the thresholding. In some such embodiments, the set of respiratory features may include an area of an inspiratory flow curve. For example, the set of respiratory features may include a ratio of a measure of ventilation and a breath time. The method may also involve setting the periodic breathing state as a function of a counter. The counter may optionally represent a number of processed breaths.

In some embodiments, the method may be implemented as a device to detect periodic breathing. For example, a processor may be configured to determine a set of respiratory features from a measure of respiratory flow, to threshold the set of respiratory features and to detect a periodic breathing state based on the thresholding.

Some additional embodiments of the technology may involve a method for detecting sleep onset. The method may include determining a set of respiratory features from a measure of respiratory flow. The method may also include thresholding the set of respiratory features. The method may then include determining a sleep state score based on the thresholding. This sleep state score may be indicative of a sleep state. The method may then involve detecting sleep onset as a function of the thresholding and the determined sleep state score. In some such embodiments, the set of respiratory features may include a function of a determined expiratory peak flow location. Optionally, the function may be a difference between (a) a ratio of the expiratory peak flow location and an expiratory time and (b) an average of a plurality of the ratios determined over a number of breaths. Moreover, the method may also involve, based on the detecting, outputting a sleep onset index representing a transition into a first sleep period for a treatment session.

In some embodiments, the method may be implemented as a device to detect sleep onset. For example, a processor may be configured to determine a set of respiratory features from a measure of respiratory flow. The processor may also be configured to threshold the set of respiratory features, to determine a sleep state score based on the thresholding and to detect a sleep onset state based on the thresholding and the determined sleep state score.

In still further embodiments, the technology involves a respiratory treatment apparatus. The apparatus may include a flow generator to generate a flow of breathable gas at a pressure above atmospheric pressure to a patient interface. It may further include a flow sensor to measure a flow of the breathable gas attributable to patient respiration. It may further include a controller coupled to the flow generator and the flow sensor. This controller, such as one or more processors, may be configured to detect one of a plurality of sleep states substantially based on data from the measure of flow from the flow sensor. The controller being further configured to control a respiratory pressure treatment regime based on the detected sleep state.

For example, this respiratory pressure treatment regime may include control of an expiratory pressure relief where the controller reduces a pressure reduction amount of the expiratory pressure relief when the detected one of the plurality of sleep states is a state attributable to sleep. Moreover, the respiratory pressure treatment regime may include an expiratory pressure relief control where the controller increases a pressure reduction amount of the expiratory pressure relief when the detected one of the plurality of sleep states is a state attributable to wakefulness. Still further, the respiratory pressure treatment regime may include a detection of events from data of the measure of flow where the events include at least one of an apnea and a hypopnea and where the events are scored when the detected one of the plurality of sleep states is a state attributable to sleep. Optionally, the detected events may be separately reported in association with detected sleep states.

In some embodiments, the respiratory pressure treatment regime may include automatic adjustment of a therapeutic pressure level where the controller increases the therapeutic pressure level in response to a detection of a respiratory abnormality and reduces the therapeutic pressure level in response to a comparison of a sleep stability index and a threshold.

Still further the respiratory pressure treatment regime may include a detection of cardiogenic flow from the measure of flow where the detection of cardiogenic flow is controlled when the detected one of the plurality of sleep states is a state attributable to sleep. This respiratory pressure treatment regime may also include a detection of a central apnea based on the detection of a presence of cardiogenic flow. In such cases, the detected one of the plurality of sleep states may be an NREM state.

Additional features of the present respiratory technology will be apparent from a review of the following detailed discussion, drawings and claims.

BRIEF DESCRIPTION OF DRAWINGS

The present technology is illustrated by way of example, and not by way of limitation, in the figures of the accompanying drawings, in which like reference numerals refer to similar elements including:

FIG. 23-A is a graph of a respiratory flow signal that may be characterized as a non-REM sleep transition;

FIG. 25 includes tables with example input and output values for thresholding features with the graph of FIG. 24;

FIG. 26 has three tables with example values of rules that govern the state transition probabilities used for determining sleep state;

FIG. 27 has four tables with example values of additional rules that govern the state transition probabilities used for determining sleep state;

DETAILED DESCRIPTION

Figure 1:
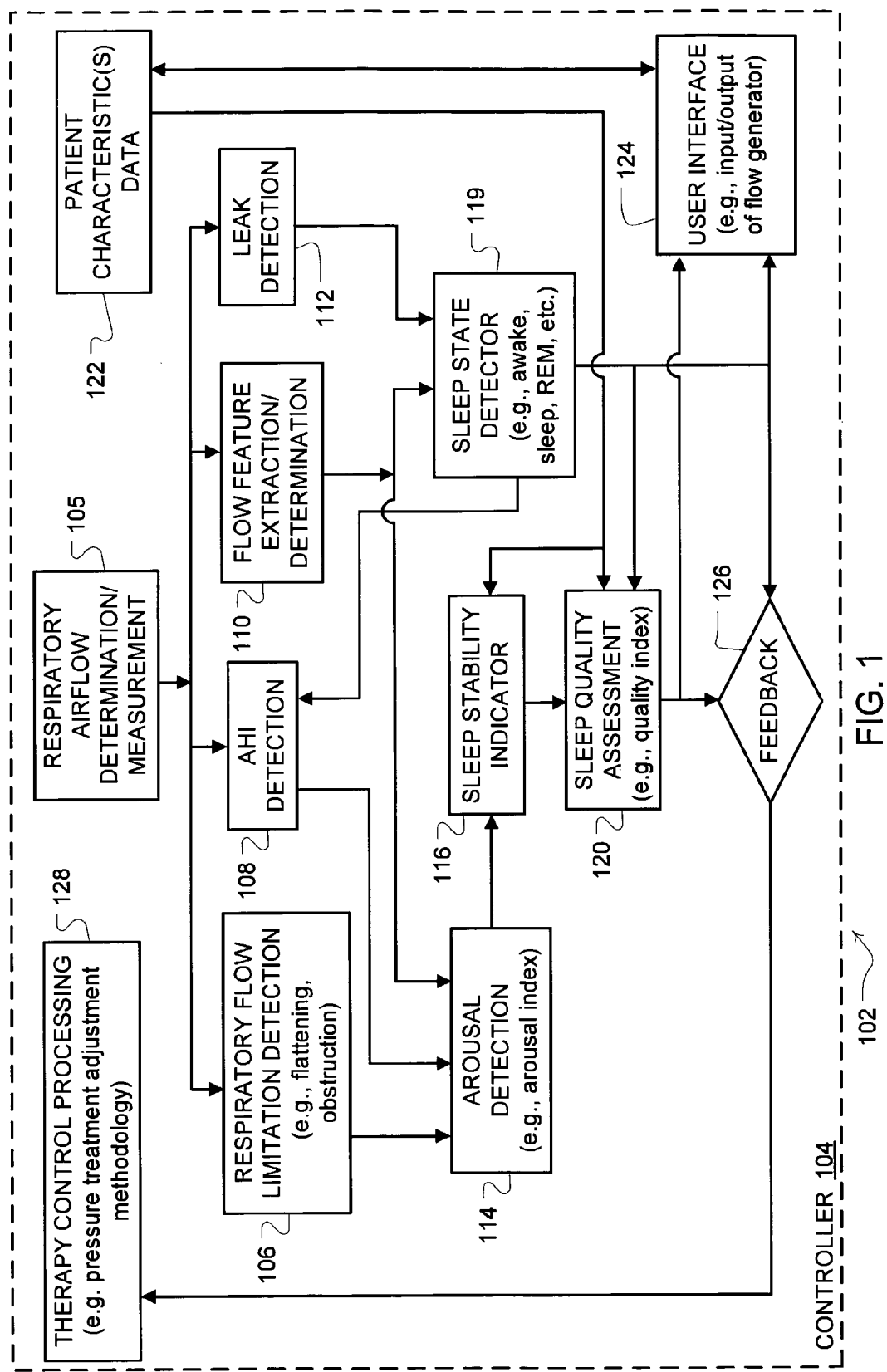
FIG. 1 is a block diagram of an example controller for a sleep condition detection apparatus of the present technology.

As illustrated in FIG. 1, embodiments of the present technology may include a sleep condition detection device 102 or apparatus having a controller 104 that may have one or more processors to implement particular sleep state and/or sleep arousal detection methodologies such as the algorithms described in more detail herein. In the example embodiment, the system of the controller may have multiple components or modules that control the various aspects of the controller. The components or modules may be implemented with integrated chips, a memory and/or other control instruction, data or information storage medium. For example, programmed instructions encompassing such detection methodologies may be coded on integrated chips in the memory of the device or apparatus to form an application specific integrated chip (ASIC). Such instructions may also or alternatively be loaded as software or firmware using an appropriate data storage medium in which they reside to then control one or more programmable processors.

In the illustrated embodiment of FIG. 1, the controller 104 may have access to data from a respiratory flow signal or may otherwise include an optional flow measurement module 105. With such a module, the controller may directly measure respiratory flow. Thus, the processor may control the assessment or detection of sleep conditions as described in more detail herein based on previously recorded respiratory flow data from a prior sleep session. Alternatively, the detection may be performed during a sleep session contemporaneously with the measuring of a respiratory flow signal using a present measuring of flow data with a flow sensor. Thus, in some embodiments, the device itself may optionally be implemented with a flow sensor for measuring a respiratory flow signal for use with implemented methodologies. For example, flow to or through a nasal cannula or mask may be measured using a pneumotachograph and differential pressure transducer or similar device such as one employing a bundle of tubes or ducts to derive a flow signal. Optionally, a flow signal may be inferred from other sensors, such as, a motor current sensor as described in PCT/AU2005/001688 filed on Nov. 2, 2005, the entire disclosure of which is incorporated herein by cross reference.

As discussed in more detail herein, flow data may be processed by optional modules such as a flow limitation detection module 106, apnea and/or hypopnea (AHI) detection module 108, respiratory flow characteristic or feature extraction module 110 and leak detection module 112. The AHI detection module 108 may also utilize input from the sleep state detection module 114 in the determination of apnea and/or hypopnea events. Output signals or data from the flow limitation detection module 106, AHI detection module 108 and respiratory feature extraction module 110 may be processed by the arousal detection module 114. Similarly, output from the leak detection module 112 and respiratory feature extraction module 110 may be processed by the sleep state detection module 118. Still further, output signals or data from the arousal detection module 114 and patient characteristics data store 122 may be processed by the sleep stability detection module 116. A sleep quality detection/assessment module 120 may then process output data or signals from the sleep stability detection module 116, the patient characteristics data store 122 module and the sleep state detection module 118. Output signals or data from the sleep quality assessment module 120 may then be displayed with a user interface module 124 and/or serve as input to a feedback control module 126, which serves to modify or make adjustments to the settings of a therapy control processing module 128, such as a pressure treatment therapy setting.

In some embodiments of the present technology, the detectors and modules of the controller may be implemented with to the following features and functions.

A. Patient Characteristic(s) Store Module

This module may control the storing of data and information characteristics of patients utilizing the sleep condition detection device 102. The data may be input via the user interface module 124, which may optionally include a keyboard, buttons of a panel, touch screen etc. For example, under the control of the module, the device may prompt a patient or clinician to select or enter one or more patient characteristics such as: age, sex, weight, height, BMI and/or pre-existing condition data (e.g., a health condition that may potentially affect heart rate variability, a health condition that may potentially be involved in creating differences in airflow patterns, other current physiological condition, etc.). Such health conditions may include asthma, emphysema, chronic cardiovascular disease, for example. The stored data may in turn be utilized by other modules of the device.

These patient characteristics may be utilized to weight an output of the methodologies described herein. For example, there may not be an absolute airflow feature that can be used as a mean for every patient to compare to in detection of different sleep states. Thus, the patient characteristics may be used to adjust sensitivity of the feature extractor (or the thresholds to which the respiratory characteristics are compared). In this way, the significance of the characteristics of the airflow may be more accurately assessed for different patients. For example, a patient who is above the age of 50 will naturally have lesser stability in the upper airway. Therefore, a system or method of the present technology may be selectively less severe on assessing flow stability for such patients.

Other uses of the patient characteristics by the system are described in more detail herein.

B. Flow Limitation Detection Module

The respiratory flow limitation detection module 106 may be configured to detect a measure of a limitation of respiratory flow from flow signal data. For example, the device may be configured to detect a measure of flow limitation, such as a fuzzy flow limitation measure as disclosed in PCT/AU08/000,647, filed on May 9, 2008, (published as International Patent Application Publication No. WO/2008/138040) and U.S. Provisional Patent Application No. 60/965,172 filed on Aug. 17, 2007, the disclosures of which are hereby incorporated herein by reference. Optionally, it may be configured to detect flow limitation by analysis of flattening of the flow data. For example, the flattening may be determined by the method disclosed in U.S. Pat. No. 5,704,345, the entire disclosure of which is incorporated herein by cross reference.

C. AHI Detection Module

In some embodiments, the flow data may be processed to detect or score hypopneas and/or apneas (e.g., obstructive apneas and/or central apneas). For example, the device may be configured to detect an obstructive apnea, partial obstruction and/or central apnea by any of the methods described in U.S. Pat. Nos. 6,138,675 and 6,029,665, the entire disclosures of which are incorporated herein by cross reference.

In some embodiments, the AHI detection module 108 may be modified to exclude scoring of events based on the leak detection module 112. For example, if leak is detected, it may disable any contemporaneously scored event until leak is not detected. In this way, the AHI may be calculated with respect to total mask-on time. That is, the time the actual mask is worn by the patient rather than total sleep time of the patient. This can result in avoiding an overestimate in the performance of a flow generator (FG).

Thus, in some embodiments, the AHI may optionally be combined with a flattening indicator and leak indicator to provide a simple sleep quality score that may yield an elementary insight into sleep quality.

D. Leak Detection Module

Accordingly, in some embodiments, the flow data may be processed to detect the presence of a leak, such as a leak associated with the dislodgement of a mask or a high leak. For example, a high leak may be considered a leak in excess of a certain quantity threshold (e.g., a leak of greater than about 0.4 Liters per second (1/s)). By way of further example, the device may be configured to detect when a leak is occurring or has occurred by any of the methods described in U.S. Pat. Nos. 6,152,129 and/or 6,532,957, the entire disclosures of which are incorporated herein by cross reference. Leak detection may optionally serve to assist in classifying arousal from sleep that is due to mask leak as well as to exclude AHI scoring in the presence of leak as previously mentioned.

E. Feature Extraction Module

One or more respiratory flow characteristics may be determined by the feature extraction module 110. In typical embodiments, the features may be determined by processing respiratory flow data. The features may optionally be calculated on a breath-by-breath basis or by use of a sliding window comprising several breath cycles. The features may then serve as indicators or input for the other modules of the system. For example, depending on the data from one or more of the measured characteristics, various conclusions may be drawn in other modules about sleep conditions with the flow data. The following are example features that may be detected or determined from the flow data.

1. Inspiratory Peak Flow Variation

Figure 2:
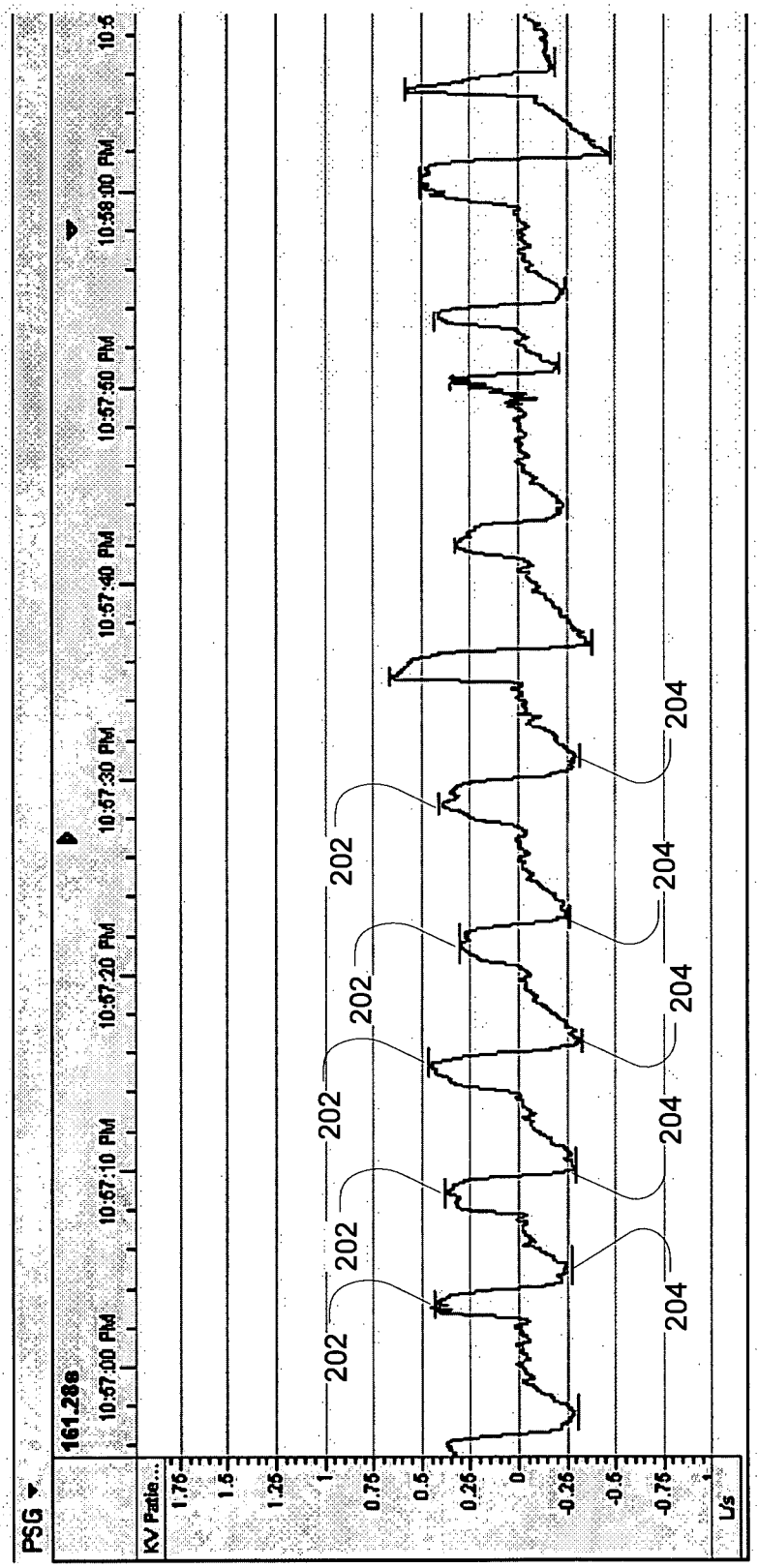
FIG. 2 is an illustration of inspiratory and expiratory peak flow variation characteristics of a respiratory flow signal.

This respiratory flow characteristic may be determined by calculating a variance of the Inspiratory Peak Flow. Such a characteristic is illustrated in FIG. 2. The variation may be determined with a sliding window including a plurality of breaths (e.g., 5 breaths). As illustrated in FIG. 2, the calculation utilizes the inspiratory peak flow values 202 for a group of consecutive breaths. When assessed by the state detector with suitable thresholds, this value may be indicative of different sleep states as follows:

(a) Awake State: exhibits high levels of Inspiratory Peak Flow Variation.
(b) REM Sleep State: exhibits moderate levels of Inspiratory Peak Flow Variation.
(c) NREM Sleep State: exhibits minimal levels of Inspiratory Peak Flow Variation.

This inspiratory peak flow variation feature may be labeled herein as "IPFV".

2. Expiratory Peak Flow Variation

This respiratory flow characteristic may be determined by calculating a variance of the Expiratory Peak Flow. Such a characteristic is illustrated in FIG. 2. The variation may be determined with a sliding window including a plurality of breaths (e.g., 5 breaths). As illustrated in FIG. 2, the calculation utilizes the expiratory peak flow values 204 for a group of consecutive breaths. When assessed by the state detector with suitable thresholds, this value may be indicative of different sleep states as follows:

(a) Awake State: exhibits high levels of Expiratory Peak Flow Variation
(b) REM Sleep State: exhibits moderate levels of Expiratory Peak Flow Variation
(c) NREM Sleep State: exhibits minimal levels of Expiratory Peak Flow Variation.

This expiratory peak flow variation feature may be labeled herein as "EPFV".

3. Expiratory Peak Flow Location/Expiratory Time Ratio

Figure 3:
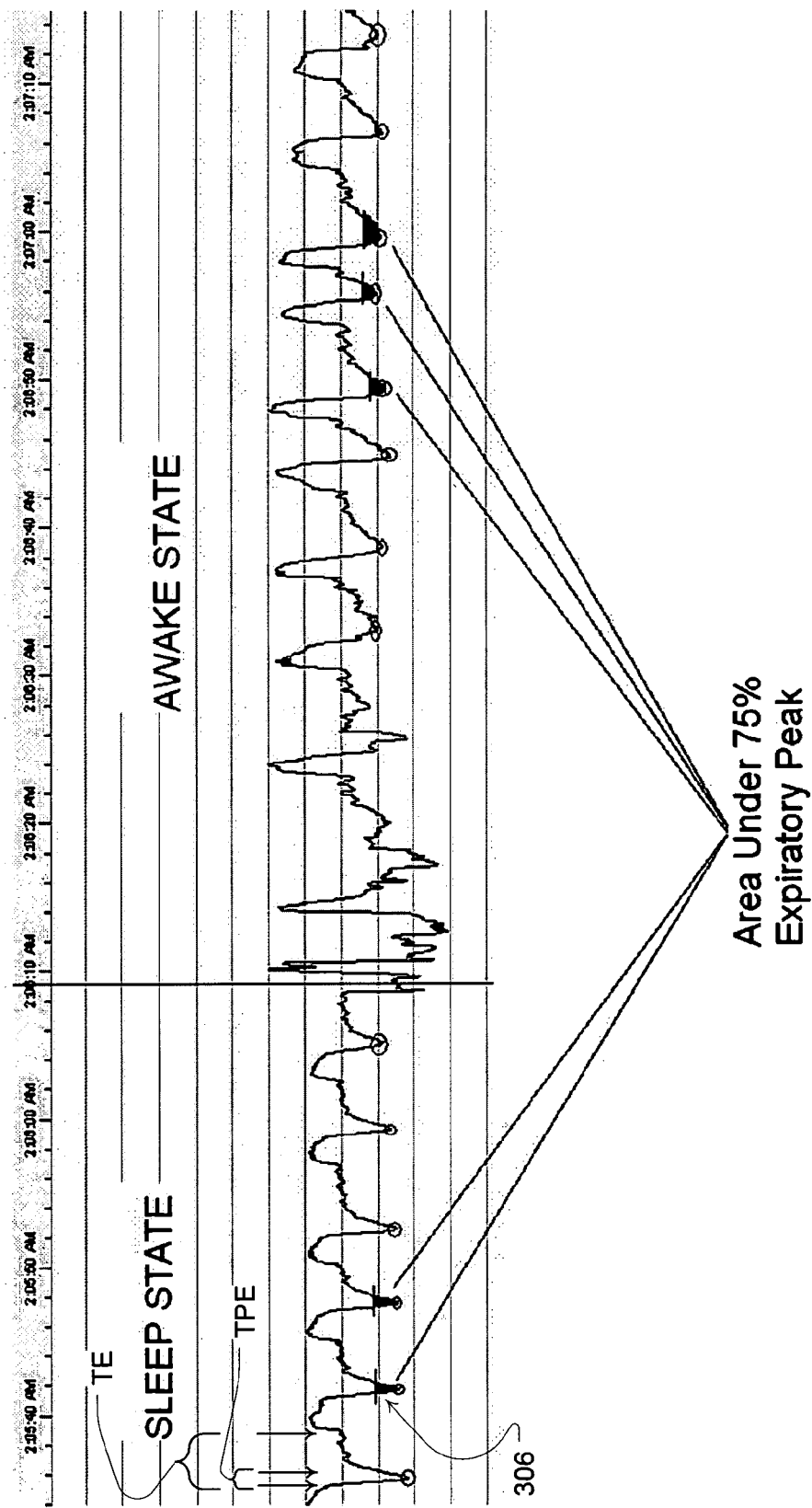
FIG. 3 is an illustration further characteristics of a respiratory flow signal including an expiratory peak flow location to expiratory time ratio and area under a proportion of an expiratory peak.

As illustrated in FIG. 3, this respiratory flow characteristic may be calculated as a ratio between a time taken to reach Expiratory Peak Flow (TPE) from the beginning of expiration to the total Expiratory Time (TE). The ratio is illustrated in FIG. 3. When assessed by the state detector with suitable thresholds, this value may be indicative of different sleep states as follows:

(a) Awake State: exhibits a large Expiratory Peak Flow Location/Expiratory Time Ratio compared to sleep states
(b) REM Sleep State: exhibits a small Expiratory Peak Flow Location/Expiratory Time ratio compared to awake state.
(c) NREM Sleep State: exhibits a small Expiratory Peak Flow Location/Expiratory Time ratio compared to awake state.

4. Expiratory Peak Flow Location/Expiratory Time Ratio Variation

This respiratory flow characteristic may be calculated as a variation (e.g., variance) of the ratio of the prior characteristic. The variation may be determined with a sliding window including a plurality of breaths (e.g., 5 breaths).

When assessed by the state detector with suitable thresholds, this value may be indicative of different sleep states as follows:
- (a) Awake State: exhibits a large Expiratory Peak Flow Location/Expiratory Time ratio Variation from one breath to another.
- (b) REM Sleep State: exhibits small Expiratory Peak Flow/Expiratory Time ratio Variation from one breath to another.
- (c) NREM Sleep State: exhibits small Expiratory Peak Flow/Expiratory Time ratio Variation from one breath to another.

5. Area Under 75% Expiratory Peak Flow

This respiratory flow characteristic may be calculated as a proportion of the area of the Expiratory Flow curve (e.g., between 75% and 100%) of Expiratory Peak Flow. An example of the expiratory peak flow area 306 is illustrated in FIG. 3. When assessed by the state detector with suitable thresholds, this value may be indicative of different sleep states as follows:
- (a) Awake State: exhibits a larger area below 75% Expiratory Peak Flow.
- (b) REM Sleep State: exhibits a small area below 75% Expiratory Peak Flow
- (c) NREM Sleep State: exhibits a small area below 75% Expiratory Peak Flow 6. Area Under 75% Expiratory Peak Flow Variation This respiratory flow characteristic may be calculated as a variation (e.g., variance) of the area of the prior characteristic. The variation may be determined with a sliding window including a plurality of breaths (e.g., 5 breaths). When assessed by the state detector with suitable thresholds, this value may be indicative of different sleep states as follows:
- (a) Awake State: exhibits a larger variation in the area below 75% Expiratory Peak Flow from one breath to another.
- (b) REM Sleep State: exhibits a small variation in the area below 75% Expiratory Peak Flow from one breath to another.
- (c) NREM Sleep State: exhibits a small variation in the area below 75% Expiratory Peak Flow from one breath to another.

7. Time from 75% Expiratory Peak Flow to Start Inspiration

Figure 4:
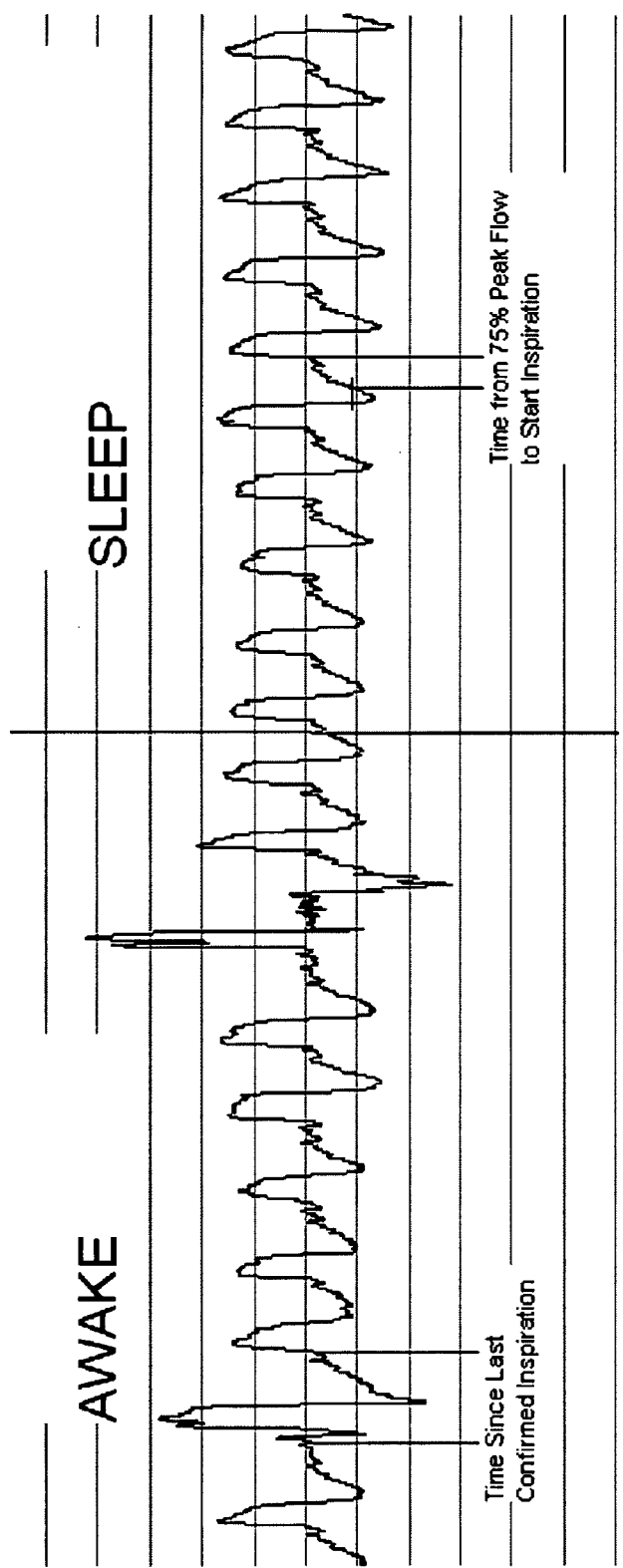
FIG. 4 is an illustration of further characteristics of a respiratory flow signal including a time from a proportion of expiratory peak flow and time since last confirmed inspiration.

This respiratory flow characteristic may be calculated as a time between a proportion (e.g., 75%) of Peak Flow of the rising part of the Expiratory Peak Flow and a start of the next Inspiration. This characteristic is illustrated in FIG. 4. When assessed by the state detector with suitable thresholds, this value may be indicative of different sleep states as follows:
- (a) Awake State: exhibits a slower rise time from 75% Expiratory Peak Flow to Start Inspiration
- (b) REM Sleep State: exhibits a faster rise time from 75% Expiratory Peak Flow to start Inspiration
- (c) NREM Sleep State: exhibits a faster rise time from 75% Expiratory Peak Flow to start inspiration 8. Time Since Last Confirmed Breath This respiratory flow characteristic may be calculated as a time from the last confirmed inspiration. The characteristic is illustrated in FIG. 4. Such a characteristic may be assessed with suitable thresholds by the arousal detector described in more detail herein.

9. Time Since Last Confirmed Breath Variability

This respiratory flow characteristic may be calculated as a variation (e.g., variance) of the time from last confirmed inspiration of the prior characteristic. The variation may be determined with a sliding window including a plurality of breaths (e.g., 5 breaths). When assessed by the state detector with suitable thresholds, this value may be indicative of different sleep states as follows:
- (a) Awake State: exhibits a large variation in the Time Since Last Confirmed Breath from one breath to another.
- (b) REM Sleep State: exhibits a moderate variation in the Time Since Last Confirmed Breath from one breath to another.
- (c) NREM Sleep State: exhibits a small variation in the Time Since Last Confirmed Breath from one breath to another.

This Time Since Last Confirmed Breath Variability feature may be labeled herein as "TSLBV".

10. High Breath Frequency Periods

Figure 5:
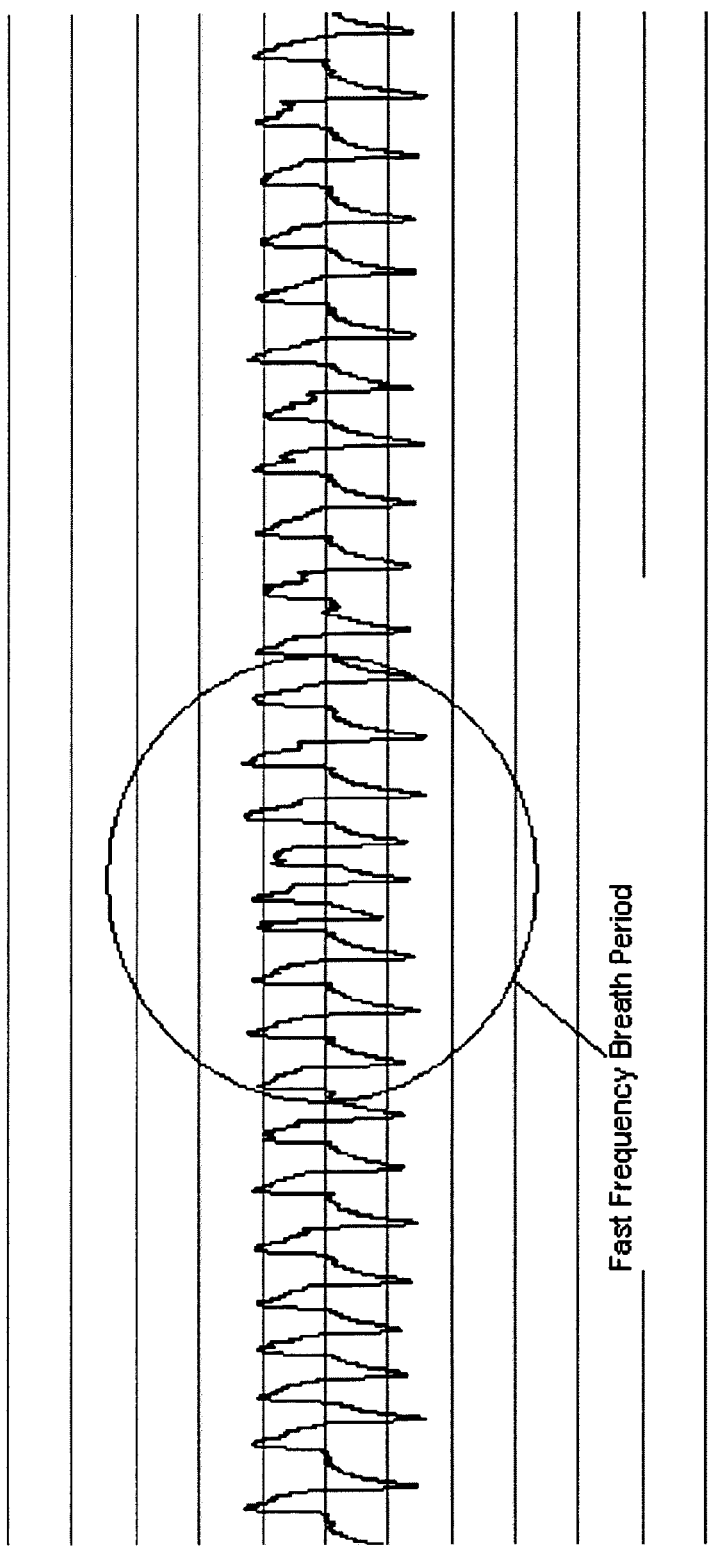
FIG. 5 is an illustration of an high breath frequency characteristic of a respiratory flow signal.

This respiratory flow characteristic may be calculated by a scan for any small sections of high frequency breathing over a sliding breath epoch (e.g., 15 breaths). The feature is illustrated in FIG. 5. When assessed by the state detector with suitable thresholds, this value may be indicative of REM breathing.

11. Inspiratory Time Variability

This respiratory flow characteristic may be calculated as a variation (e.g., variance) in the inspiratory time. The variation may be determined with a sliding window including a plurality of breaths (e.g., 5 breaths). When assessed by the state detector with suitable thresholds, this value may be indicative of different sleep states as follows:
- (a) Awake State: exhibits large variation in Inspiratory Time
- (b) REM Sleep State: exhibits moderate variation in Inspiratory Time
- (c) Sleep State: exhibits small variation in Inspiratory Time 12. Breath Consistency Checker This feature may be implemented to determine whether there is consistency in the following respiratory flow characteristics from breath to breath over a period of a number of breaths (e.g., 5 breaths). The consistency check considers Inspiration Time, Inspiratory Peak Flow Location, Expiration Time, Expiratory Peak Flow Location. Minor differences in the characteristics may be deemed consistent.

13. Feature Consistency Checker

This feature checks for a variation in the respiratory flow characteristics previously identified (e.g., characteristics 1-12) over a multiple breath period (e.g., 30 breaths). For example, an automated analysis of any of the features over a period of a number of breaths (e.g., 30) may identify whether any feature is consistent or has significant variation. For example, in an awake period, a Peak Flow Variability feature will be on average higher than in a sleep period. Such a value may not be above a required awake threshold each time it is calculated, such as over a period of 30 breaths, but there may be a significant proportion above the threshold that may be evaluated.

14. Time to Reach 95% Inspiratory Peak Flow

Figure 6:
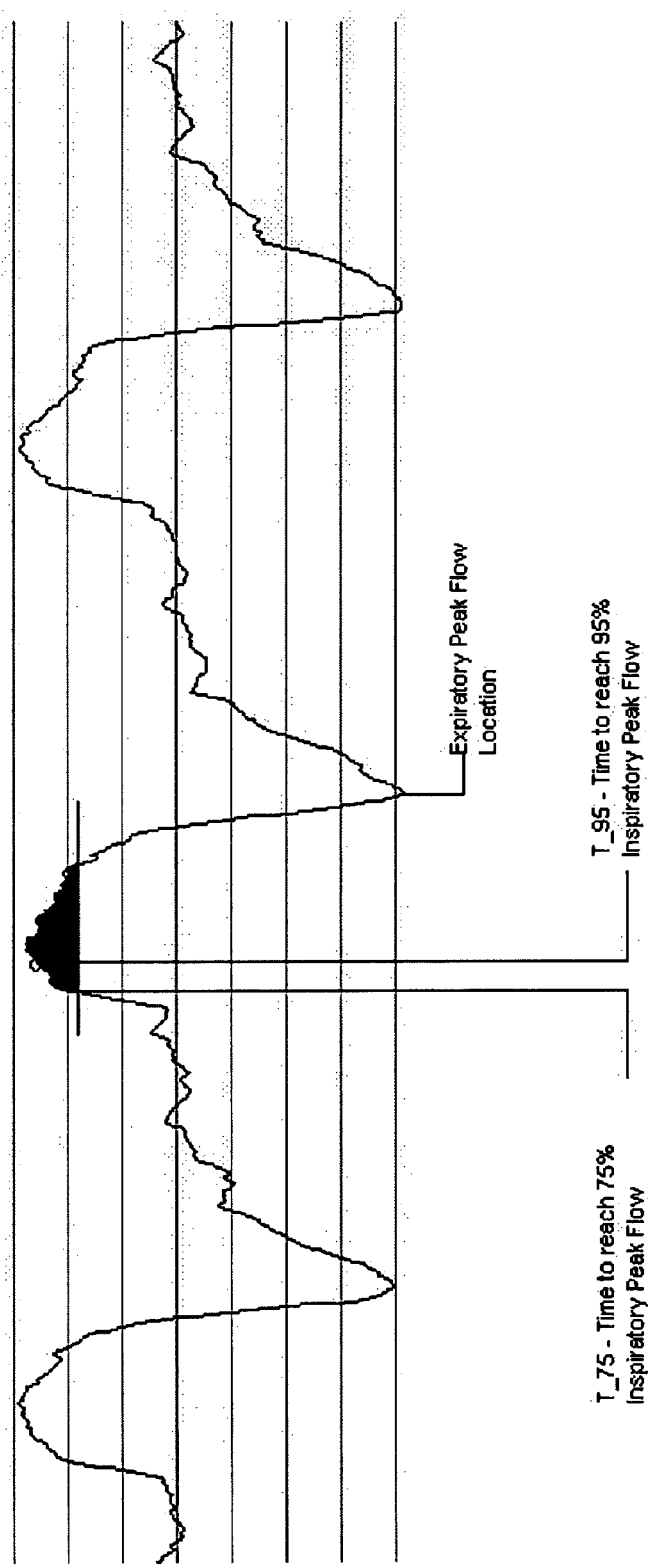
FIG. 6 is an illustration of further characteristics of a respiratory flow signal including a time to reach a proportion of inspiratory peak flow, area above a proportion of inspiratory peak flow and a time between a proportion of peak flow and an expiratory peak flow location.

This respiratory flow characteristic may be calculated as a time it takes for a breath to reach a proportion (e.g., 95%) of inspiratory peak flow from the beginning of inspiration. This 95% time characteristic is shown in FIG. 6 with reference character $T\_95$. This respiratory flow characteristic feature may be utilized in the assessment by the arousal detection module 114.

15. Area Above 75% Inspiratory Peak Flow

This respiratory flow characteristic may be calculated as the area of the inspiratory peak flow curve above a proportion (e.g., 75%) of Inspiratory Peak Flow. This respiratory flow characteristic feature may be utilized in the assessment by the arousal detection module 114. A 75% time characteristic (T_75), which is a time at which a breath reaches a proportion (e.g., 95%) of inspiratory peak flow, may be determined to then calculate the area as shown by the shaded region of FIG. 6. This Area above 75% Inspiratory Peak Flow feature may be labeled herein as "IP75A".

16. Area Above 75% Inspiratory Peak Flow Variation

This respiratory flow characteristic may be calculated as the variance in the area of the preceding respiratory flow characteristic. The variance may be determined with a sliding window including a plurality of breaths (e.g., 5 breaths). This respiratory flow characteristic feature may be utilized in the assessment by the arousal detection module 114. This Area above 75% Inspiratory Peak Flow Variation feature may be labeled herein as "I75AV".

17. Time Between 95% Inspiratory Peak Flow and Expiratory Peak Flow

This respiratory flow characteristic may be calculated as a time between a proportion (e.g., 95%) of the rising side of the Inspiratory Peak Flow curve and the Expiratory Peak Flow location. This respiratory flow characteristic may be utilized in the assessment by the arousal detection module 114.

18. Current Breath 3mvTtot Ratio to Previous Breath 3mvTtot

A 3mvTtot Ratio may be calculated as the 3mvTtot from the current breath divided by the 3mvTtot from a previous breath. The 3mvTtot may be determined as the ratio between the average minute ventilation (e.g., a three minute ventilation) and a total breath period (e.g., time period for the duration of the current breath). The minute ventilation may be determined as the average ventilation taken during preceding minutes (e.g., in a range of about two to five minutes, but preferably three minutes).

19. Current Breath IPkFlow to a Portion of Current Breath IPkFlow:

A ratio of the peak inspiratory flow (IPkFlow) and a portion (e.g., 75%) of the peak inspiratory flow (IPkFlow) from the current breath of the inspiratory flow. This feature may be labeled herein as "PF75PF".

F. Sleep/Awake Detection Module

Figure 7:
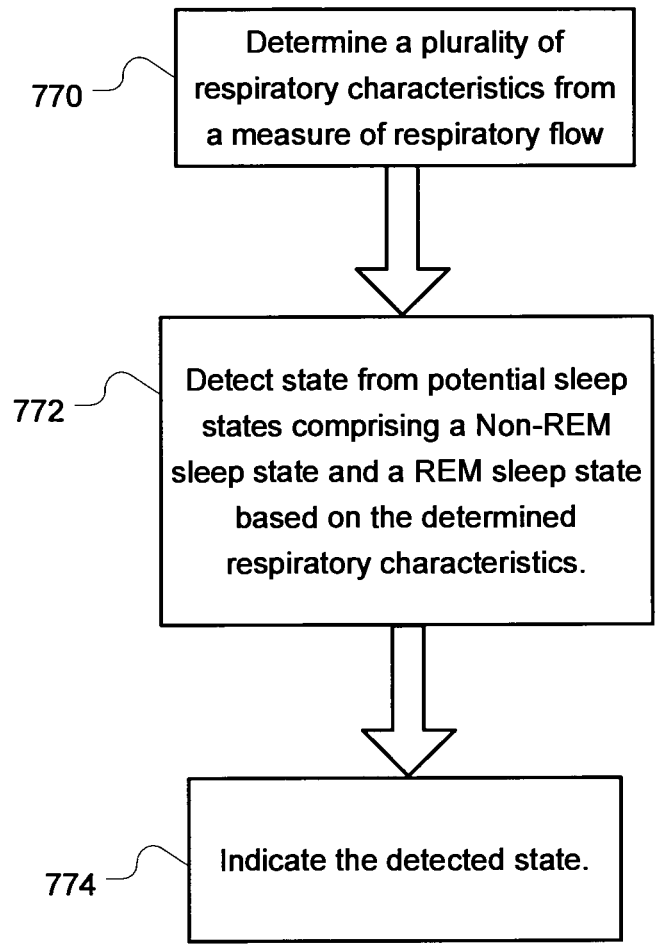
FIG. 7 is a flow diagram of an example embodiment of a methodology for controlling an apparatus to detect a sleep state based on data from a flow sensor.

An example methodology associated with the sleep state detection module 118 is illustrated in FIG. 7. Essentially, the detector may be implemented with a methodology to detect a sleep state from data representing a measured flow of breathable gas. At 770, the method may involve determining a plurality of respiratory characteristics from a measure of respiratory flow. Although the extraction of such respiratory characteristics may be integrated with the sleep state detector, this extraction may correspond with data provided from the feature extraction module 110. At 772, the method of the sleep detector may also involve detecting a state from potential sleep states such one or more of a Non-REM sleep state, a REM sleep state, Phasic REM state, Tonic REM state, a Deep REM sleep state and/or a Light REM sleep state. At 774, the detecting of the state may be based on the determined respiratory characteristics. In such embodiments, this state detection is substantially based on the determined respiratory characteristics in the sense that any of these states may be detected from data taken by a respiratory flow sensor and without traditional sleep stage sensor determination techniques (i.e., data analysis from electroencephalogram (E.E.G.), electromyography (E.M.G.) and electrooculography (E.O.G.) sensors.) or respiratory effort bands. A processor may then indicate the detected state. For example, it may store the detected state in memory, apply it to the input of another module (e.g., the sleep quality assessment module 120) and/or produce it as output such as on a display of the user interface module 124.

In one example embodiment, the respiratory characteristics extracted from the flow signal may be processed to classify the sleep state as a Markov Classification system. In such an embodiment, a Non-Stationary Markov Classification system may be employed to identify the sleep state of the patient.

The name Markov model is derived from one of the assumptions which allows this system to be analyzed; namely the Markov property. The Markov property states: given the current state of the system, the future evolution of the system is independent of its history. At each step the system may change its state from the current state to another state, or remain in the same state, according to a certain probability distribution. The changes of state are called transitions, and the probabilities associated with various state-changes are called transition probabilities.

Mathematically, the Markov property can be represented as:

$$Pr(X_{n+1}=x|X_n=x_n, \ldots, X_1=x_1)=Pr(X_{n+1}=x|X_n=x_n).$$

Where:

X—is a random variable

N—is a number representing a particular state $Pr(X_{n+1}=x|X_n=x_n)$ is more commonly represented as $P_{i,j}$ ($i=X_n$, $j=x$). These computations determine the probability of the state transitioning from state $x_n$ to x. A state transition matrix may contain probabilities of a state changing to any one of the other states (or simply remaining in its current state). In the context of some of the embodiments of the current technology, the sleep state may be the random variable and there may be a number of possible states (e.g., three states in the case of a Non-REM Sleep state, Awake state and a REM sleep state). In this example, therefore, a three dimensional state transition matrix would be calculated. With additional states the matrix and calculations would be increased suitably.

Accordingly, some embodiments, the following methodology may be implemented to determine a sleep state from the respiratory characteristics or features that may be input from the feature extraction module.

(1) Calculate the State Transition Table.

The state transition table can be non-stationary (e.g., vary with time) due to the direct dependence that the transition probabilities have on the features extracted from the flow signal (which also vary over time). Certain features are characteristic of specific sleep stages as previously described. Any number of combinations of such features (e.g., from the feature extractor module) may be used to derive these state transition probabilities. The probabilities may be determined from a set of thresholds for each of the respiratory characteristics. The set of thresholds may be determined through empirical analysis and recorded in the device for the probability assessment. Therefore, at every update of the sleep state, the transition table may be recalculated. This may be performed on a breath-by-breath basis. In the case of three states, there would be nine transitions representing a transition from each state to the other states and from each state to itself.

(2) Calculate the Probabilities of the Current State (e.g., Non-REM Sleep, Awake and REM Sleep) Based on the Previous State.

An output from the leak detection module 112 may optionally provide a conditioner of the probabilities of the matrix. For example, if there high level of detected leak, it may be expected that the flow signal will be less stable or otherwise less indicative of any particular sleep state. It may even be indicative of an awake state. Thus, in some embodiments, the methodology may modify the weighting of the sleep state probability suitably to reduce the affect of leak.

(3) Output the Most Likely Sleep State.

Accordingly, the sleep state detection module may produce a Sleep/Awake indicator or index indicative of various detected states by breaking down and analyzing the respiratory flow signal to associate them with certain stages of sleep (e.g., 1=awake, 2=non-REM, 3=REM or 1=awake, 2=non-REM, 3=light REM, 4=deep REM etc.). An advantage of such an approach is that it may be used to provide an indication of the total sleep time when the method is used to log the duration of each state. It may also be implemented to provide information on a patient's sleep structure (e.g., a timing, frequency and duration of awake intervals, Non-Rapid Eye Movement (NREM) sleep intervals, Rapid Eye Movement (REM) sleep intervals, Deep Rapid Eye Movement (DREM) sleep intervals and/or Light Rapid Eye Movement (LREM) sleep intervals, etc.). Furthermore, it may also be implemented for an improved AHI calculation when such an index is used with the AHI detection module so as to permit AHI determination with particular reference to the total sleep time as previously discussed.

Example Sleep State Detector Embodiment

Figure 20:
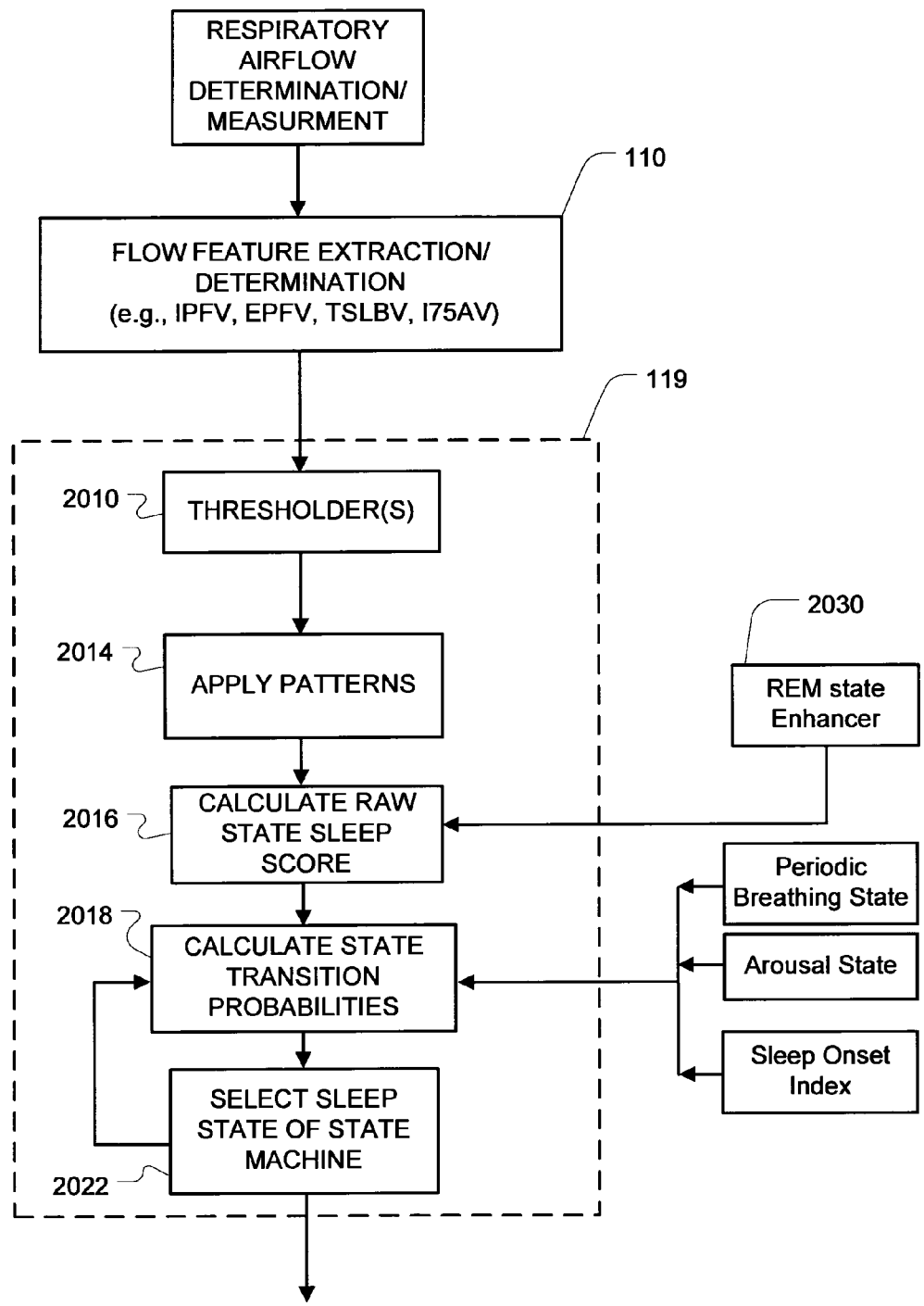
FIG. 20 illustrates a processing methodology of an example sleep state detector.
Figure 22:
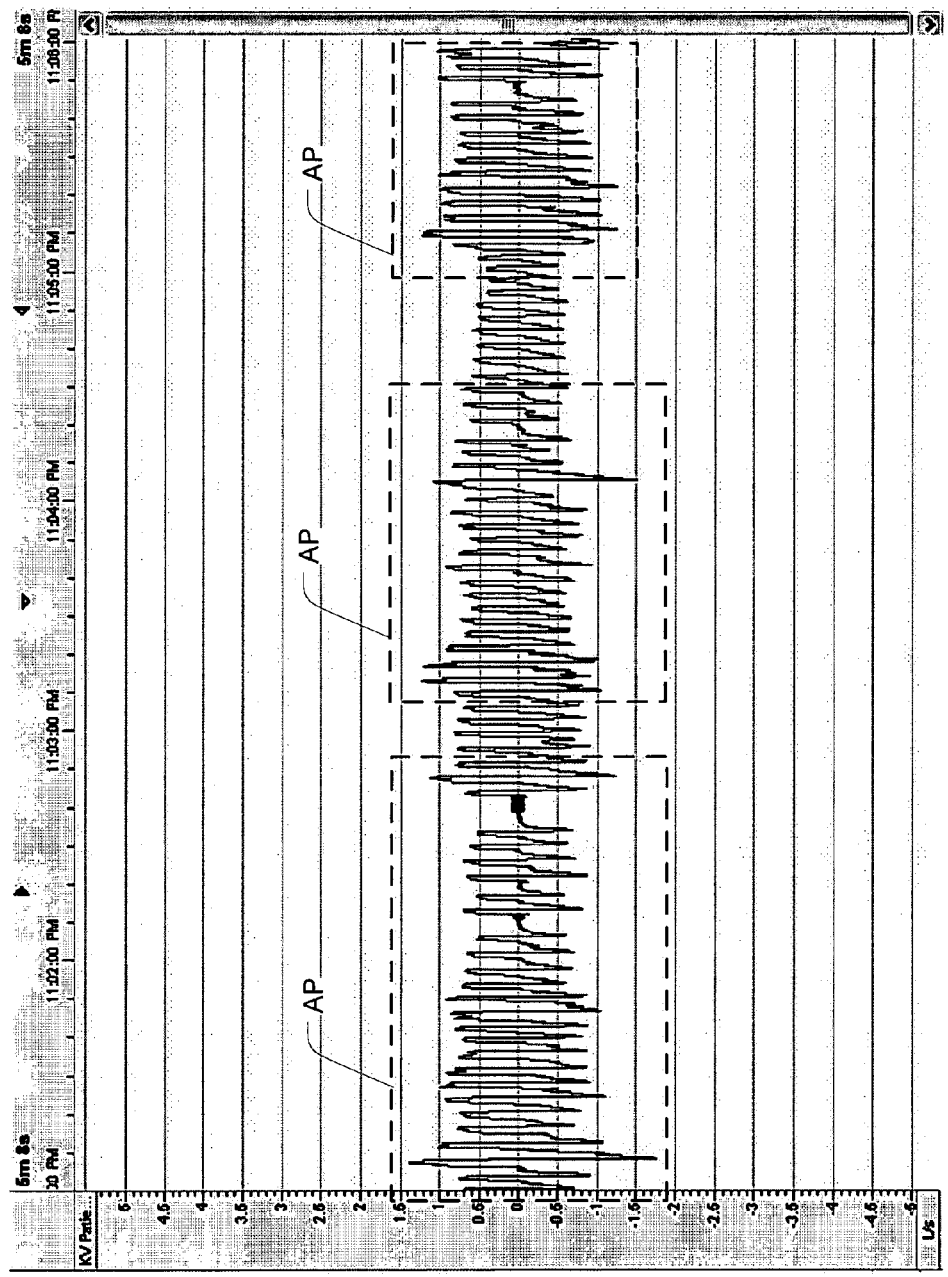
FIG. 22 is a graph of a typical respiratory airflow signal from a person while he is awake.
Figure 23:
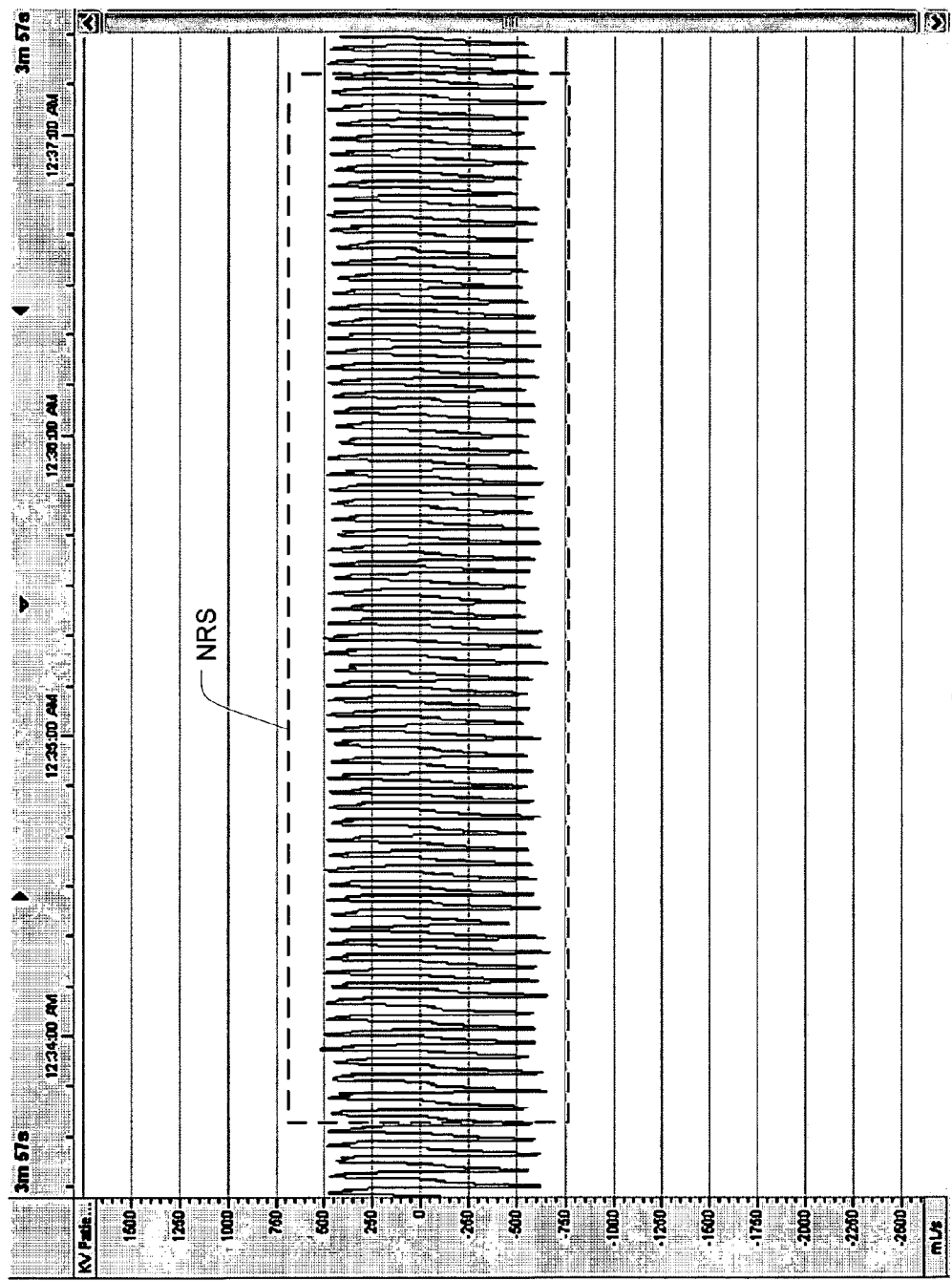
FIG. 23 is a graph of a typical respiratory airflow signal from a person who is asleep.

In a further example embodiment of the technology, a sleep state detection module 119 may be configured with the processing illustrated in the block flow diagram of FIG. 20. The processing represents a calculation of a sleep state of the patient. To this end, traditional R&K PSG based scoring divides sleep into 6 stages:

i.) Awake
ii.) NREM Stage 1
iii.) NREM Stage 2
iv.) NREM Stage 3
v.) NREM Stage 4
vi.) REM This type of sleep stage scoring is based on many different biosignals including EEG, EOG and respiratory effort bands. In the current embodiment, sleep stage is estimated primarily based on analysis of the respiratory flow signal. For this reason, characterizing the detailed sleep architecture with all of the stages of R&K PSG is not implemented with this module. Rather, sleep state detection by the present embodiment is compressed into the following four states:

i.) Awake
ii.) NREM Sleep Transition (effectively Stage 1 sleep)
iii.) NREM Sleep (Stages 2,3,4)
iv.) REM To this end, the Awake state and REM sleep state may be considered to be similar to the R&K sleep scoring. These states in relation to the respiratory flow are illustrated in FIG. 22 (awake) and FIG. 23 (NREM). The NREM Sleep state may be considered to be stages 3 and 4 (slow wave sleep) and parts of stage 2. Respiratory flow is steady and metronomic during this stage as illustrated in FIG. 23. The NREM SLEEP state 2114 in relation to respiratory flow is illustrated in the NREM sleep region (shown as box NRS) of FIG. 23. This region may be characterized by the detector as NREM SLEEP state 2114.

The NREM Sleep T (Transition) is effectively stage 1 sleep where there is the transition from Awake to Sleep. At sleep onset, there is typically some level of ventilator sleep instability (due to a change in $CO_2$ set point from awake to sleep). This is usually associated with stage 1 of sleep and sometimes can extend to stage 2 (as may typically be seen in an EEG). The respiratory flow will tend to be arrhythmic during this period. Examples of the arrhythmic periods (AP) of an awake state are illustrated in FIG. 22. This pattern of ventilator instability is not limited to only the first awake-sleep transition of the night. It can potentially occur in later parts of the night if or when the patient arouses and attempts to transition back into sleep.

In the detection of the above referenced states, the detector of the current embodiment will process one or more features of the feature extractor 110 previously discussed, which are based on the data representing respiratory airflow from a flow sensor. The state decision may be further based on Patient Characteristics (e.g., Age, BMI, Sex, Current Physiological Condition) from the patient characteristics data 122, data from the arousal module 144 and/or data from the leak detection module 112.

Figure 21:
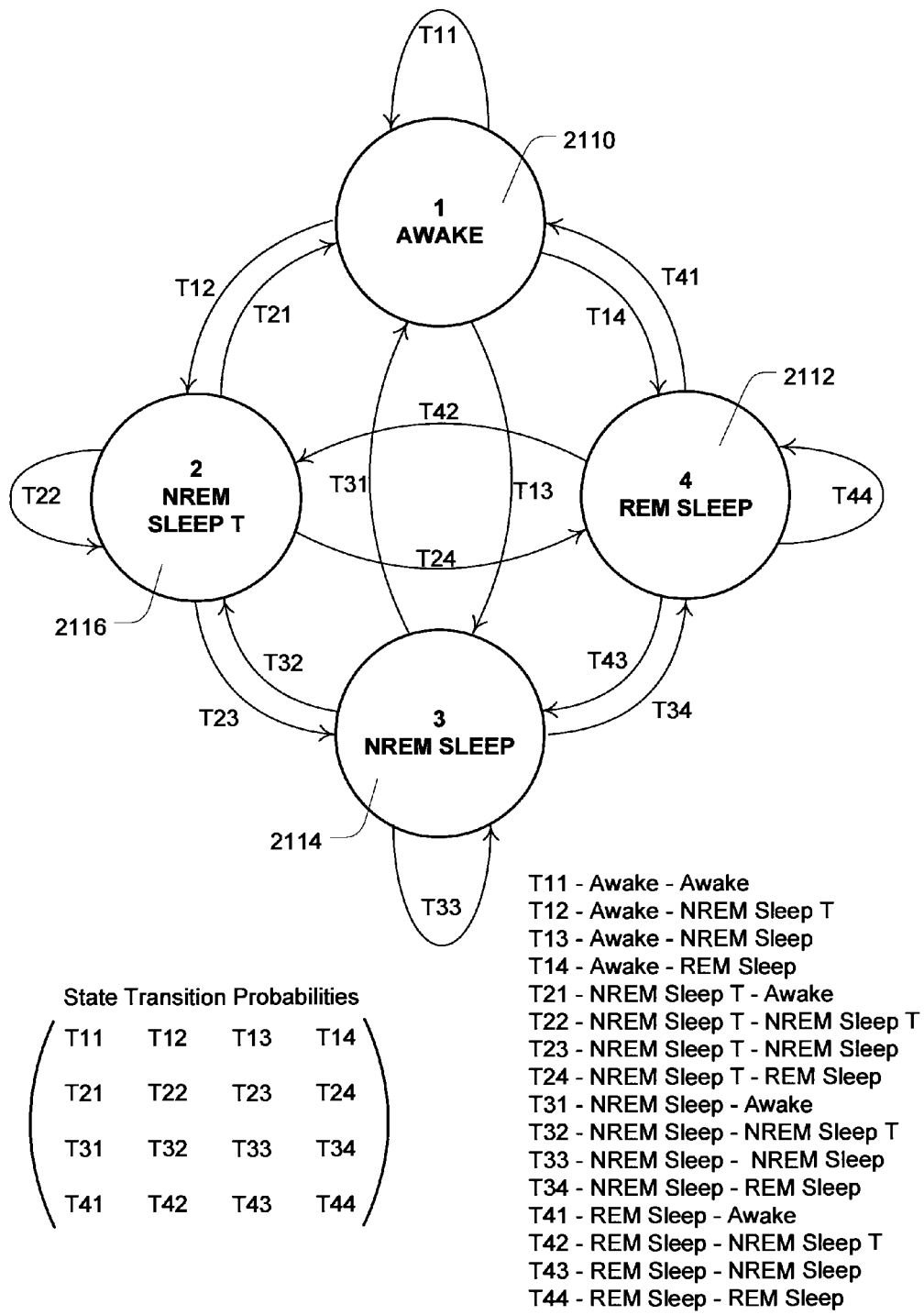
FIG. 21 shows a finite state machine state diagram for implementing detectable sleep condition states in an example embodiment of a sleep state detector.

In this embodiment, a finite state machine is implemented to classify sleep stages. As illustrated in FIG. 21, three fundamental states are defined: an Awake state 2110; a REM Sleep state 2112; and a NREM Sleep State 2114. A new sleep state is determined at the end of each breath cycle by calculating transition probabilities. The transition from one state to the next or to the same state is based on the most probable of the transition probabilities shown in FIG. 21 (labeled as Transition Probability T11, T12, etc).

Theoretically, a patient has a probability to transition from any one state to another at any point in time. However, the physiology of sleep is such that it is a dynamic quantity and there is an element of randomness to the whole process. Thus, the transition probabilities should be conditioned and updated at the end of each breath cycle. A sleep state is then calculated based on these transition probabilities. Further, conditioning may be implemented to account for the instability (sometimes seen as periodic breathing) that can occur in sleep. An additional state of the finite machine, a NREM Sleep Transition state 2116, is also defined and if a sustained amount of sleep instability is detected, the state machine will transition to this NREM Sleep Transition state. This NREM SLEEP T state 2116 in relation to respiratory flow is illustrated in FIG. 23-A. In the graph, an example sleep instability region (shown as box SOI) occurring at sleep onset can be characterized by the detector as NREM SLEEP T state 2116.

The processing methodology of this example sleep state detection module 119 will now be described in regard to FIG. 20. The detection of sleep state by the module may be based on an analysis of one or more of the features of the feature extractor 110 as discussed above. Based on a measure of respiratory flow, the feature extractor 110 may determine one or more of the features. In this example embodiment, the IPFV (Inspiratory Peak Flow Variability), EPFV (Expiratory Peak Flow Variability), TSLBV (Time Since Last Breath Variability) and I75AV (Area above 75% Inspiratory Peak Flow Variability) features may be analyzed.

Figure 24:
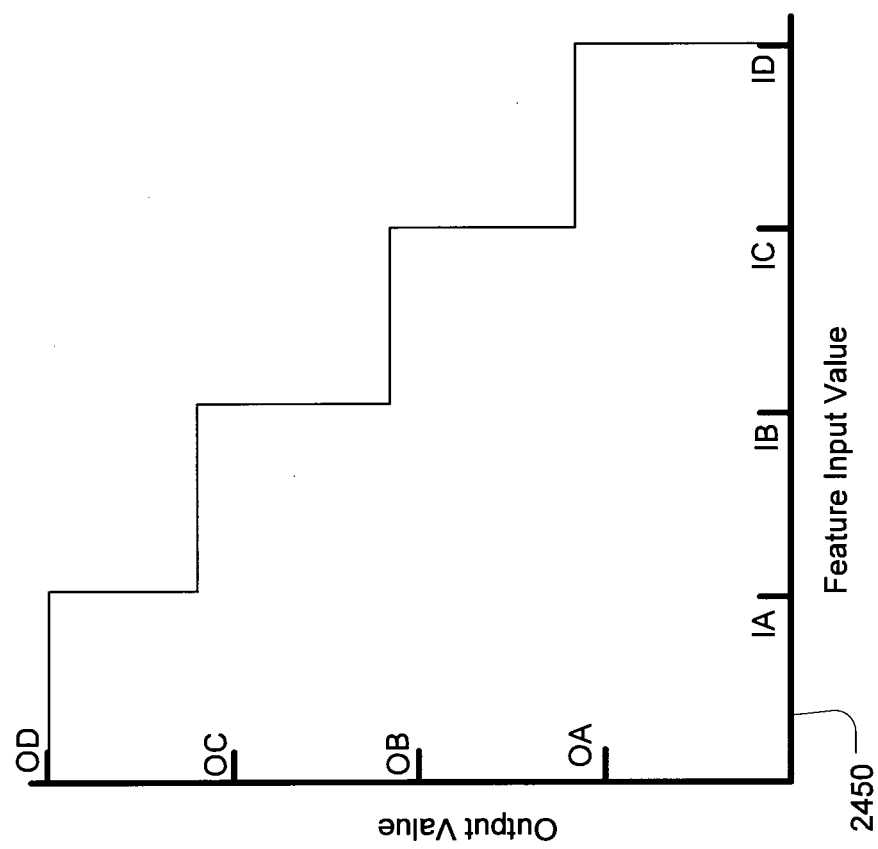
FIG. 24 shows an example graph of a generic threshold function for features analyzed by a sleep state detector of the technology.
Figure 28:
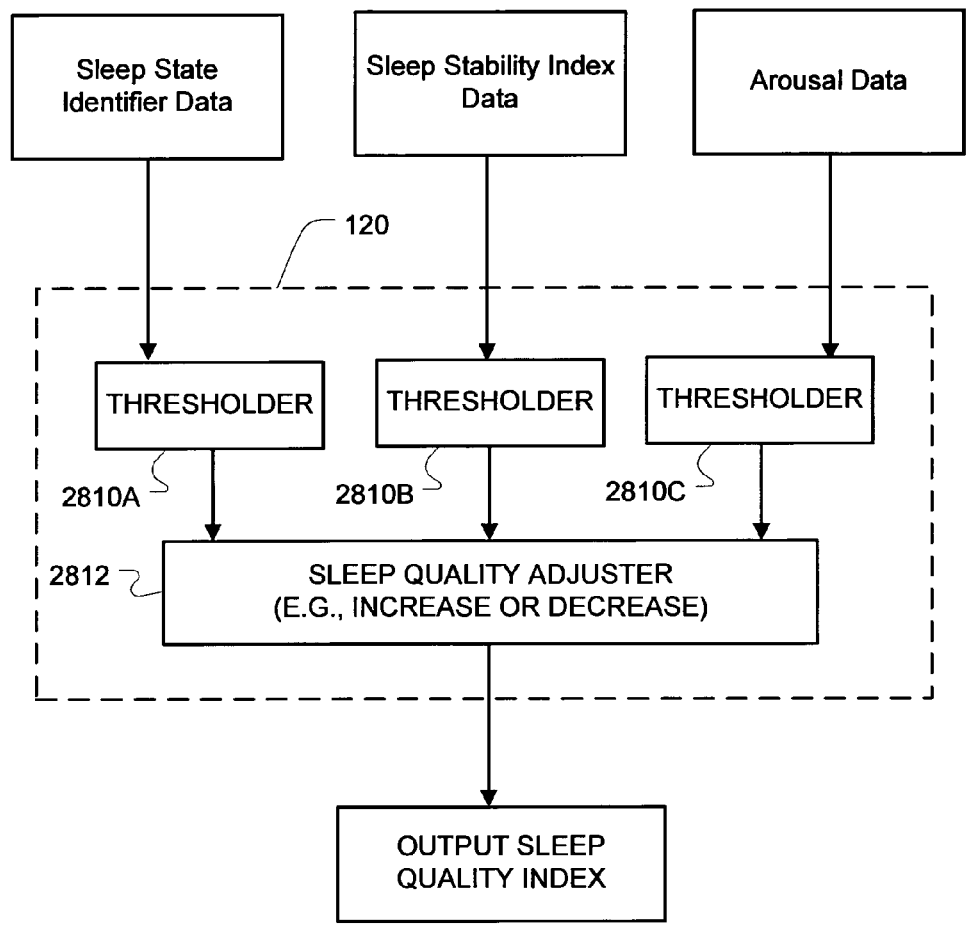
FIG. 28 is a block diagram of the processing components of an example sleep quality assessment module.

Each feature is provided to a thresholder 2010 where one or more threshold function(s) such as the examples illustrated in FIGS. 24 and 25 are applied to each feature of the feature subset. However, depending on the number of states, each feature will typically be applied to a threshold for each possible fundamental sleep state as illustrated in the tables of FIG. 25.

For example, when thresholding of the IPFV feature, the function of graph 2450 of FIG. 24 may be implemented with the example input values IA, IB, IC and ID and example output values OA, OB, OC and OD taken from table IPFV (shown as table at reference character 2540A in FIG. 25) for each possible sleep state. As previously mentioned in these tables, the input values IA, IB, IC etc. represent consecutive ranges for the output values. Thus, for table IPFV (shown as table at reference character 2540A in FIG. 25), IA is a range from less than 0.001 up to and including 0.001. IB is a value of a range greater than the range of IA up to and including 0.003. IC is a value of a range greater than the range of IB up to and including 0.009. ID is a value of a range greater than the range of IC up to and including 10, which may be considered a maximum possible input value. For example, in the case of the IPFV feature having a determined value of 0.003, an output value, which may be considered a sleep state weight, of 0.1 is selected as the output that is attributable to the Awake state for the IPFV feature. Further, an output value of 0.8 is selected as the output that is attributable to the NREM state for the IPFV feature and an output value of 0.1 is selected as the output that is attributable to the REM state for the IPFV feature. Similarly, output weights are selected for the EPFV feature. However, in the case of the EPFV feature, the input and output values for function of graph 2450 for each state will be based on the values of the EPFV table (shown as table at reference character 2540B in FIG. 25). Similarly, weights attributed to the fundamental sleep states will be determined for the TSLBV feature and I75AV feature with their respective tables (shown as table TSLBV at reference character 2540C and table I75AV at reference character 2540D in FIG. 25).

Although specific values are illustrated in the tables of FIG. 25 it will be understood that these are merely examples. Other values may be implemented and may be empirically determined either from a group of patients or for a particular patient. Thus, these values may be learned with processing based on machine learning and pattern recognition techniques. Examples of techniques that may be adopted include cluster analysis, support vector machines and Bayesian classification.

The output weights are then provided to a pattern applier 2014. In this processing, data for patterns of various individual features are combined. To this end, weights associated with several subsets of features are likely to contain information more indicative of sleep stage than compared to individual features. Thus, a pattern may be considered one or more features that collectively represent information indicative of sleep stage. Moreover, a range of patterns may be collectively utilized to identify sleep stage. In this regard, an ideal set of these patterns will contain information that meet the following conditions:

i.) The patterns contain sleep stage specific information.

ii.) Any two patterns do not contain the same information about a sleep stage.

While the first condition can be satisfied relatively easily, the second condition can be more challenging. Given the nature of the respiratory flow signal and subsequently calculated features, it is a difficult task to produce patterns with little or no overlap. Thus, a judicious combination of these patterns may be implemented in order to obtain the necessary information.

For example, in one embodiment, the pattern applier may implement the following patterns (P1, P2, P3, P4 and P5):

| Pattern ID | Feature Subset |
| --- | --- |
| P1 | IPFV, EPFV, TSLBV |
| P2 | IPFV, EPFV |
| P3 | TSLBV |

-continued

| Pattern ID | Feature Subset |
| --- | --- |
| P4 | IPFV |
| P5 | IPFV, I75AV |

Based on the patterns, the feature weights from the thresholder for each sleep state are combined, for example, by summing the weights. Thus, for each pattern ($P_1 \ldots P_N$), and each state ($S_1 \ldots S_I$) there will be I×N pattern scores produced. For the above five pattern example, and in the case of three states, there will be twenty pattern scores (i.e., P1_awake, P1_NREM_sleep, P1_rem, . . . , P5_awake, P5_NREM_sleep, P5_nrem).

An example of the overall pattern weight calculation follows:

Features used: IPFV, EPFV, TSLBV

Feature weights (wn) from threshold functions:
  Awake Score:
    IPFV: w11
    EPFV: w12
    TSLBV: w13
  NREM Sleep Score:
    IPFV: w21
    EPFV: w22
    TSLBV: w23
  REM Sleep Score:
    IPFV: w31
    EPFV: w32
    TSLBV: w33

Patterns used:

| Pattern ID | Feature Subset |
| --- | --- |
| P1 | IPFV, EPFV, TSLBV |
| P2 | IPFV, EPFV |
| P3 | TSLBV |

Calculate Pattern Weights:
  P1_awake=$\alpha$*(w11+w12+w13)
  P1_NREM sleep=$\beta$*(w21+w22+w23)
  P1_rem=$\mu$*(w31+w32+w33)
  P2_awake=$\alpha$1*(w11+w12)
  P2_NREM sleep=$\beta$1*(w21+w22)
  P2_rem=$\mu$1*(w31+w32)
  P3_awake=$\alpha$2*w13
  P3_NREM sleep=$\beta$2*w23
  P3_rem=$\mu$2*w33

In this calculation, biasing factors $\alpha$, $\beta$, $\mu$, $\alpha$1, $\beta$1, $\mu$1, $\alpha$2, $\beta$2 and $\mu$2 may be implemented as shown above. The factors may permit some adjustment to the pattern scoring based on one or more of the patient characteristics of the patient characteristics data 122. For example, one or more of these may be set to 1 if none of the particular patient characteristics would tend to make the particular pattern more or less indicative of a particular state. However, other values may used and may be determined empirically based on the patient characteristics.

The raw sleep state calculator 2016 would then generate a particular raw sleep state score for each state by combining the respective state scores. In the above example, the raw sleep state calculator 2016 would then produce the following Raw Awake Scores:

Awake=P1_awake+P2_awake+P3_awake;

NREM_Sleep=P1_NREM_sleep+P2_NREM_sleep+ P3_NREM_sleep;

REM=(P1_rem+P2_rem+P3_rem)*(REM_Enhancer_Index);

In this embodiment, a REM enhancer factor (designated "REM_Enhancer_Index") may be utilized. This factor is produced by the REM State Enhancer 2030 shown in FIG. 20. The processing of the REM State Enhancer 2030 is discussed in more detail herein. This essentially provides an additional weight for adjusting (e.g. by multiplication) the raw REM sleep score.

Generally, in this processing, the weights are calculated only for pattern-based scores such as the NREM state, REM state or Awake state. The NREM Sleep T state of the graph of FIG. 21 may be considered a "state" dependant score rather than a pattern dependant score. In this regard, any values for this transition state are based on a Periodic State and Arousal State at the time of probability calculation as discussed in more detail herein with regard to the transition probabilities of FIG. 27.

The raw state scores are then processed by the state transition probability calculator 2018. This processing generally involves a determination of state transition probabilities such as the transition probabilities identified in the chart of FIG. 21 according to the probability methods discussed herein. These probabilities may be considered a further conditioning step in the sleep stage calculation process. Example probability values are shown in the tables of FIGS. 26 and 27. Generally, the transition probabilities may be combined with the raw score for a given state, for example, by multiplication, to generate a modified sleep state score. In this way, the raw sleep scores may be biased by the transition probabilities. However, for purposes of the NREM Sleep T state, its raw state score may be assumed to be 1 such that the transition probabilities will become the modified state score for this state.

In this regard, given the nature of the physiology of sleep, there is an element of randomness that is taken into account in determining sleep state. For example, the first awake phase (i.e., prior to the onset of sleep) is more likely to be larger (e.g., a longer time period) than subsequent awake states throughout the night. The first sleep stage of the night should not be a REM phase unless the patient has a specific REM sleep disorder. Thus, certain rules may be applied in determining the state transition probabilities to account for some of these conditions. Examples of these transition conditions and their associated probabilities are discussed in more detail herein in reference to FIGS. 26 and 27.

Moreover, some of the transition probabilities may be based on a Sleep Onset Index, which is discussed in more detail herein. Generally, the sleep onset index may be a binary index. For example, if it reads a value 1, this represents that the patient is in sleep (either NREM Sleep or NREM Sleep T). Similarly, if it reads 0, this represents that the patient is in Awake State. However, if the patient is in the first Awake state for the night and this index reads 0, all transition probabilities that govern a state change to any of the three sleep states will be zero. (e.g., T12, T13 and T14 will be zero if Sleep Onset Index is 0).

Based on the modified sleep state scores, a state selector 2020 may then determine the next sleep state. By comparison of the modified sleep state scores, a next state may be selected. For example, the modified sleep state score with the greatest score may be considered the detected state of the states of the state machine of FIG. 21.

The process of the detection methodologies discussed for sleep state detection may be considered by the following example:
Example
Current Sleep State of Finite Machine=Awake State 2110
Calculated Raw Sleep State Scores:
Awake=0.1
NREM_Sleep=0.5
REM_Sleep=0.2
NREM_Sleep_T=1

Transition Probabilities needed based on current sleep state are T11, T12, T13, T14. Reference may be made to table 2600A for T11, T13 and T14 and it may be assumed that Rule 6 applies for this example. Reference to table 2700A may be made for T12 and it may be assumed that Rule 2 applies.
T11=0.45
T12=0
T13=0.45
T14=0.1
Modified Sleep State Score:
Awake=Awake*T11=0.045
NREM_Sleep_T=T12=0
NREM_Sleep=NREM_Sleep*T13=0.225
REM_Sleep=REM_Sleep*T14=0.02

Since NREM_Sleep has the highest score, the next sleep state can be set to the NREM_Sleep state 2114.

G. REM State Enhancer

REM state is the most difficult sleep state to detect when analyzing only the respiratory airflow signal. Therefore, some specialized features can be specifically implemented to capture features of "REM-type" airflow so as to enhance REM sleep detection. The combined output of these features provides an Enhanced REM State and may be, in part, implemented by the processing of the REM State Enhancer 2030 shown in FIG. 20.

For example, the following additional features may be determined, which may optionally, at least in part, be implemented by the processing feature extractor 110. To this end, a respiratory airflow is captured and processed to calculate the following REM-specific features:

1.) VtRat—This is a simple ratio between the current breath inspiratory tidal volume ($Vt_{curr}$) and the previous breath tidal volume ($Vt_{prev}$). In some embodiments, this ratio may be calculated according the following equation.

$$\frac{(Vt_{Curr} - Vt_{prev})}{(Vt_{curr} + Vt_{prev})}$$

2.) Deviation from Sinusoidal Curve—This feature determines a sinusoidal waveform based on amplitude and frequency of the current inspiratory breath. Then a subtraction is performed between the estimated sinusoidal curve and the actual inspiratory breath profile and the result is stored in a buffer. The variance of the values in the buffer is then calculated. The sinusoidal curve may be modified based on the patient's breathing profile. For example, machine learning or pattern recognition processing may be employed. Examples of techniques which may be adopted for this may include cluster analysis, support vector machines and Bayesian classification. In an example implementation, a simple square-root sinusoidal profile with variable amplitude and frequency may be used. Thus, based on this profile, the example calculation can be represented mathematically as follows:

$$\mathrm{var}(\sqrt{(\alpha \cdot \sin(\omega t + \phi) - \mathrm{InspFlowVec})})$$

Where α is the amplitude, ω is the frequency, t is time (in continuous domain and sample number in discrete time) and ψ is the phase.

3.) Feature Consistency Index—This index is a measure of how consistently the feature set exceeds a set threshold. The following steps are involved with calculation of this index:
  i. A collection of breaths is taken and the above referenced features are calculated for each breath and stored in threshold buffer. For example, five breaths may be taken and the determined features associated with those breaths are stored in a threshold buffer.
  ii. The features are applied to threshold functions. The threshold functions are similar to those described previously. Each time that a feature value of the feature set exceeds a set threshold, a consistency counter is incremented (e.g., by 1). For example, in a set of 5 breaths, if a feature is above the threshold for 4 of the breaths, the consistency counter would be 4.
  iii. The Feature Consistency Index is then derived by taking the ratio between feature consistency counter and the total breath collection sample size. For example, if the counter was 4 and total collection of breaths used was 5, then the Feature consistency Index will be 80%.

The Feature Consistency Index may then be output by the REM State Enhancer 2030 to serve as the RemEnhancer Index as previously discussed.

H. Transition Probability Rules

As previously mentioned, transition probabilities condition raw sleep scores in order to produce the modified sleep score. However, prior to defining how these probabilities are calculated, some general points about the natural sleep cycle may be considered:
  (a) The first awake period of the night (i.e., Sleep Onset) is more than likely going to be the longest awake period for the night.
  (b) Subsequent Awake periods will not last for more than 120 seconds unless there are external causes for awakening (e.g., Mask readjustment, going for a toilet break, being woken up by someone else or any medical conditions, such as nocturnal asthma attacks).
  (c) The first sleep transition from awake state will not be REM sleep unless the patient has a REM sleep disorder.
  (d) As part of the natural sleep cycle, a patient having been in deep sleep for more than 20 to 30 minutes is getting closer to a small awakening.

Based on the above, the following rules have been defined. However, there are many ways to interpret the above information ((a) to (d)) and to define corresponding rules. Thus, the following rules and the transition probabilities values associated therewith are merely examples. Other rules and values may be derived by machine learning or pattern recognition techniques. Examples of such techniques which may be adopted include cluster analysis, support vector machines and Bayesian classification.

Rules:

Rule 1—Patient is in 1st awake period for the night and has been in awake for less than or equal to 10 minutes.

Rule 2—Patient is in 1st awake period for the night and has been in awake for greater than 10 minutes but less than or equal to 20 minutes.

Rule 3—Patient is in 1st awake phase for the night and has been in awake for greater than 20 minutes.

Rule 4—Patient is in the 2nd awake phase for the night and has been in this state for less than or equal to 10 minutes.

Rule 5—Patient is in the 2nd awake phase for the night and has been in this state for greater than 10 minutes and less than or equal to 20 minutes.

Rule 6—Patient is in the 2nd awake phase for the night and has been in this state for greater than 20 minutes.

Rule 7—Patient is in the 3rd or a later phase of awake state and has been in this state for less than or equal to 60 seconds Rule 8—Patient is in 3rd or later phase of awake state and has been in this state for greater than 60 seconds.

Rule 9—Time since start of therapy is less than or equal to 20 minutes.

Rule 10—Time since start of therapy is greater than 20 minutes and patient has been in NREM sleep state for less than or equal to 20 minutes.

Rule 11—Time since start of therapy is greater than 20 minutes and patient has been in NREM sleep state for greater than 20 minutes and less than or equal to 30 minutes.

Rule 12—Time since start of therapy is greater than 20 minutes and patient has been in NREM sleep state for greater than 30 minutes.

Rule 13—Patient has been in REM sleep state for less than or equal to 10 minutes.

Rule 14—Patient has been in REM sleep state for greater than 10 minutes and less than or equal to 20 minutes.

Rule 15—Patient has been in REM sleep state for greater than 20 minutes.

The tables of FIG. 26 (i.e., Table 2600A, Table 2600B Table 2600C and Table 2600D) summarize the association of these rules with probability values that may be implemented to govern the state transition probabilities. In this embodiment, only one specific rule may be applicable at any one time. Based on which rule satisfies the current conditions (e.g., the current sleep state, the time spent in the present sleep state and the overall point in time of the night's sleep), the output of the tables may be applied as the transition probabilities as previously discussed. For example, if processing determines that Rule 5 is true and the current state of the machine is Awake, then the transition probability T11 will be 0.9, T13 will be 0.05 and T14 will be 0.05. The remaining transition probabilities of the tables may be similarly determined.

I. Periodic Breathing & Arousal Based Transition Probabilities

As illustrated in FIG. 20, another set of rules in the determination of transition probabilities by the state transition probability calculator 2018 may be based on the output of the periodic breathing detector and the arousal detector. For example, the periodic state detector controls the transitions to and from NREM Sleep T state. To this end, the following example rules and the related values that are illustrated in the tables of FIG. 27 may also govern the state transition probability values.

Rules

Rule 1—Patient current state is Awake
  Periodic State Counter is 0 (i.e., patient has been in periodic State for 0 breaths).

Rule 2—Patient current state is Awake
  Periodic State Counter is greater than 0 but less than or equal to 50 (i.e., patient has been in Periodic State for greater than 0 but less than or equal to 50 breaths).

Rule 3—Patient current state is Awake
  Periodic State Counter is greater than 50 (i.e., patient has been in Periodic State for greater than 50 breaths).

Rule 4—Patient current state is NREM Sleep
  Periodic State Counter is 0 (i.e., patient has been in Periodic State for 0 breaths).

Rule 5—Patient current state is NREM Sleep

Periodic State Counter is greater than 0 but less than or equal to 50 (i.e., Patient has been in Periodic State for greater than 0 but less than or equal to 50 breaths).

Arousal State Buffer Sum=0 (This buffer contains values from the previous 50 Arousal State values from the previous 50 breaths—so if sum=0 then no arousal has been detected over the previous 50 breaths).

Rule 6—Patient current state is NREM Sleep

Periodic State Counter is greater than 0 but less than or equal to 50 (i.e., patient has been in Periodic State for greater than 0 but less than or equal to 50 breaths).

Arousal State Buffer Sum>0 (This buffer contains values from the previous 50 Arousal State values from the previous 50 breaths. Thus, if the sum of the arousals is greater than zero, one or more arousals have been detected over the previous fifty breaths.)

Rule 7—Patient current state is NREM Sleep

Periodic State Counter is greater than 50 (i.e., patient has been in Periodic State for greater than 50 breaths).

Arousal State Buffer Sum=0 (This buffer contains values from the previous 50 Arousal State values from the previous 50 breaths. Thus, if the sum=0 then no arousal has been detected over the previous 50 breaths).

Rule 8—Patient current state is NREM Sleep

Periodic State Counter is greater than 50 (i.e., patient has been in Periodic State for greater than 50 breaths).

Arousal State Buffer Sum>0 (This buffer contains values from the previous 50 Arousal State values from the previous 50 breaths. Thus, if the sum is greater than zero, 1 or more arousals have been detected over the previous 50 breaths).

Rule 9—Patient current state is NREM Sleep T

Periodic State Counter is 0 (i.e., patient has been in Periodic State for 0 breaths).

Rule 10—Patient current state is NREM Sleep T

Periodic State Counter is greater than 0 but less than or equal to 50 (i.e., Patient has been in Periodic State for greater than 0 but less than or equal to 50 breaths).

Arousal State Buffer Sum=0 (This buffer contains values from the previous 50 Arousal State values from the previous 50 breaths. Thus, if the sum=0 then no arousal has been detected over the previous 50 breaths).

Rule 11—Patient current state is NREM Sleep T

Periodic State Counter is greater than 0 but less than or equal to 50 (i.e., patient has been in Periodic State for greater than 0 but less than or equal to 50 breaths).

Arousal State Buffer Sum>0 (This buffer contains values from the previous 50 Arousal State values from the previous 50 breaths. Thus, if the sum is greater than zero, 1 or more arousals have been detected over the previous 50 breaths).

Rule 12—Patient current state is NREM Sleep T

Periodic State Counter is greater than 50 (i.e., patient has been in Periodic State for greater than 50 breaths).

Arousal State Buffer Sum=0 (This buffer contains values from the previous 50 Arousal State values from the previous 50 breaths—so if sum=0 then no arousal has been detected over the previous 50 breaths).

Rule 13—Patient current state is NREM Sleep T

Periodic State Counter is greater than 50 (i.e., patient has been in Periodic State for greater than 50 breaths).

Arousal State Buffer Sum>0 (This buffer contains values from the previous 50 Arousal State values from the previous 50 breaths. Thus, if the sum is greater than zero, 1 or more arousals have been detected over the previous 50 breaths).

Rule 14—Patient current state is REM Sleep

Periodic State Counter is 0 (i.e., patient has been in Periodic State for 0 breaths).

Rule 15—Patient current state is REM Sleep

Periodic State Counter is greater than 0 but less than or equal to 100 (i.e., patient has been in Periodic State for greater than 0 but less than or equal to 100 breaths).

Rule 16—Patient current state is REM Sleep

Periodic State Counter is greater than 100 (i.e., patient has been in Periodic State for greater than 100 breaths).

The tables of FIG. 27 (i.e., Table 2700A, Table 2700B Table 2700C and Table 2700D) summarize the association of these rules with probability values that may be implemented to govern the state transition probabilities. Based on the assessment of one or more of the rules and depending on the particular state that the machine previously detected in the last breath, the output of the tables may be applied as the transition probabilities as previously discussed. For example, if processing determines that Rule 11 is true and the current state of the machine is NREM Sleep T state 2116, then the transition probability T22 will be 0 (as illustrated in Table 2700C). The remaining transition probabilities of the tables may be similarly determined.

J. Arousal Detection Module

An arousal detection module 114 may determine whether the respiratory flow data represents an arousal from sleep. In this regard, an arousal from sleep can result in a disturbance in the flow signal. Thus, a basic function of this module is to scan the data from the flow signal for such disturbances to indicate whether or not they have occurred. For example, if a disturbance is detected from the respiratory characteristics of the feature extraction module 110, the module may generate a signal or data containing the passage of flow disturbance to the sleep stability module. Optionally, a data packet may be generated to contain data from the flow disturbance as well as data from a period of the flow signal preceding the disturbance (e.g., up to fifteen breaths prior). The data may be used for further classifying the disturbance, such as described in more detail herein.

In addition to optionally utilizing respiratory characteristics from the feature extraction module 110 as previously discussed, additional respiratory characteristics may also be calculated. For example, the following respiratory characteristics may be determined:

(1) A Time to reach a proportion (e.g., 95%) of Inspiratory Peak Flow (2) An Area above a proportion (e.g., 75%) of Inpiratory Peak Flow (3) Area above a proportion (e.g., 75%) Inspiratory Peak Flow Variation (4) Time between a proportion (e.g., 95%) of Inspiratory Peak Flow and Expiratory Peak Flow An embodiment may then detect the disturbance using one or more of the respiratory characteristics. For example, a flow disturbance may be detected by assessing respiratory characteristics 1-4 recited immediately above. These features may be considered indicators of a flow disturbance. Optionally, these characteristics, with or without the prior mentioned respiratory characteristics, may be compared to a set of empirically determined thresholds to detect the disturbance. If the comparisons show that a sufficient disturbance has occurred in the flow signal the module may so indicate, for example, by outputting a positive signal or data indication (e.g., a 1 if yes otherwise a 0 if no).

Thus, an example methodology of the module may proceed on a breath-by-breath basis as follows:

(1) Import features from feature extractor.
(2) Calculate additional feature (1-4) recited immediately above).
(3) Import the current sleep state from the sleep state detection module.
(4) determine whether a flow disturbance is present.
(5) If there is a flow disturbance, check the sleep state. If the patient is in a sleep state, collect flow data from the disturbance and preceding breaths (e.g., 15 breaths) and output the data (e.g., to the sleep quality module). If there is a flow disturbance and the patient is NOT in a sleep state, no action need be taken. If there is no flow disturbance in the breath, no action need be taken.

In some embodiments, the data representing each flow disturbance may then be analyzed to determine if there is an arousal present or not. If an arousal is detected, further analysis may then characterize the arousal into one of the following types:

(i) Apnea related arousal
(ii) Hypopnea related arousal
(iii) Respiratory effort related arousal
(iv) Non-Respiratory due to mouth leak
(v) Non-Respiratory due to Periodic Leg Movement (PLM)
(vi) Non-Respiratory due to High Leak
(vii) Non-Respiratory—Spontaneous arousal.

For example, with data representing the respiratory characteristics discussed above from the feature extraction module 110, the features may be applied to a threshold function so that a weight may be associated with each feature. A flow disturbance feature is derived from the weighted outputs of the threshold function. The flow signal is further analyzed to see which of the above mentioned events preceded the flow disturbance. Subsequently, the flow disturbance may be characterized as an arousal. Outputs of the module may optionally include (a) Arousal Type and (b) Arousal Duration.

Example Arousal Detector Embodiment

Figure 13:
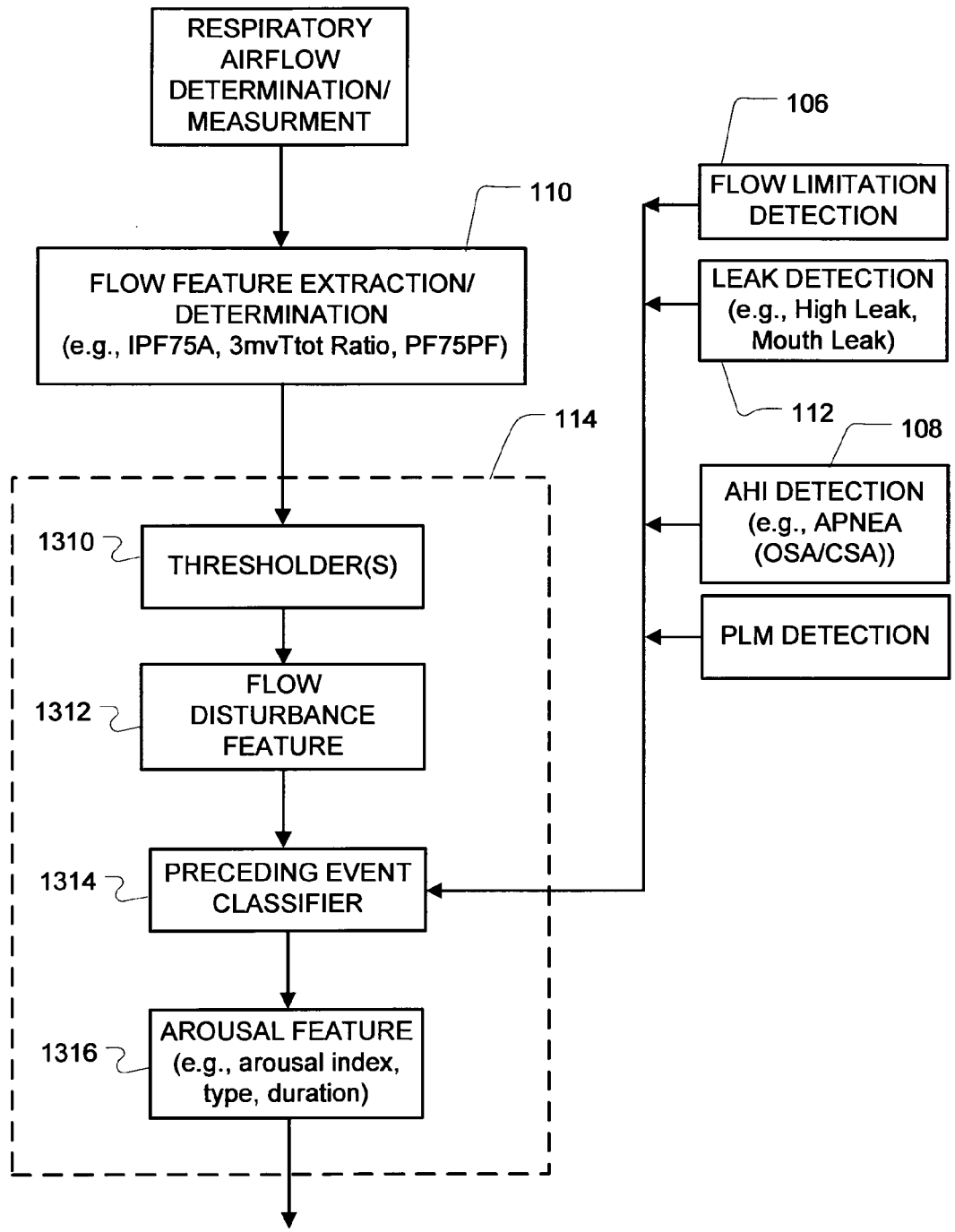
FIG. 13 is a block diagram illustrating processing methodologies of an example arousal detection module in some embodiments of the technology.
Figure 14:
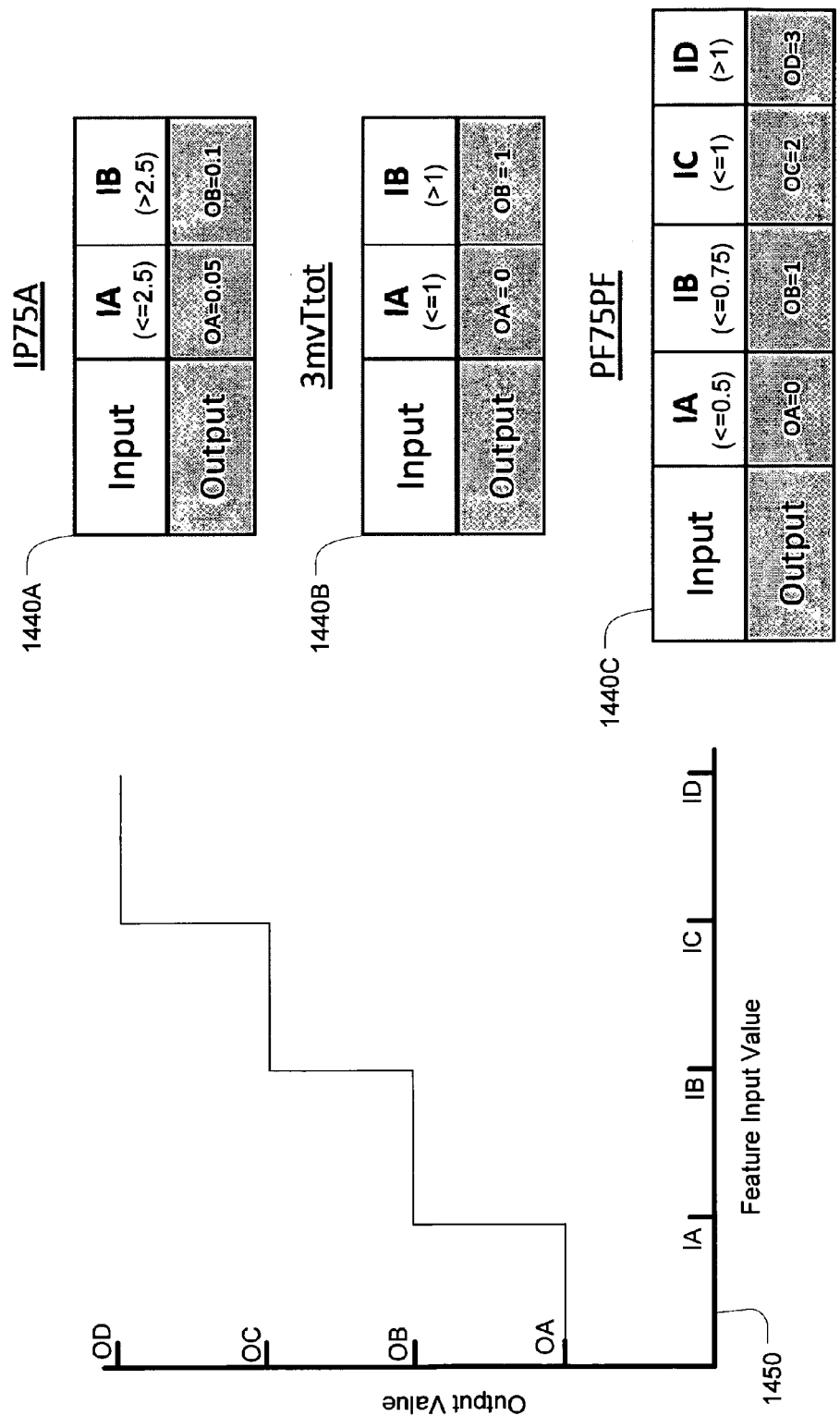
FIG. 14 shows an example graph of a generic threshold function with example input and output values for thresholding features in an example arousal detector of the technology.

In a further example embodiment of the technology, an arousal detection module 114 may be configured with the processing illustrated in the block flow diagram of FIG. 13. In the example, a respiratory airflow or filtered flow associated with a flow sensor of a flow generator is provided to and processed by the feature extractor. In this process, a particular subset of the previously described respiratory features determined by a feature extractor are utilized. This subset of features may optionally only include the IP75A (i.e., the area of the inspiratory flow curve above 75% inspiratory peak flow) feature, the 3mvTtot (i.e., the ratio between current 3 minute ventilation to Ttot (total breath time)) feature and the PF75PF (i.e., the ratio between inspiratory peak flow and 75% inspiratory peak flow) feature discussed above. Each feature is provided to a thresholder 1310 where one or more threshold function(s), such as the examples illustrated in FIG. 14, are applied to each feature of the feature subset. Although this example uses particular features, it will be understood that other embodiments may be based on other sets (e.g., all features) or subsets with any combination of the previously mentioned respiratory flow based features determined by the feature extractor.

In the example, when thresholding of the IP75A feature, the function of graph 1450 of FIG. 14 may be implemented with the example input values IA and IB and example output values OA and OB taken from table IP75A (shown as table at reference character 1440A). In the tables, the input values IA, IB, IC etc. represent consecutive ranges for the output values. Thus, for table IP75A, IA is a value of a range from less than 2.5 up to and including 2.5. IB is a value for a range greater than IA or greater than 2.5. For example, in the case IP75A feature having a determined value of less than or equal to 2.5, an output value, which may be considered a disturbance weight, of 0.05 is selected as the output that is attributable to the IP75A feature. Similarly, output weights are selected for the 3mvTtot feature. However, in the case of the 3mvTtot feature, the input and output values for function of graph 1450 will be based on the values of the 3mvTtot table (shown as table at reference character 1440B). Similarly, output weights are selected for the PF75PF feature by the function of graph 1450 and based on the values of the PF75PF table (shown as table at reference character 1440C). It is noted that although specific values are illustrated in the tables of FIG. 14 it will be understood that these are merely examples. Other values may be implemented and may be empirically determined either from a group of patients or for a particular patient. Thus, these values may be learned with processing based on machine learning and pattern recognition techniques. Examples of techniques that may be adopted for this include cluster analysis, support vector machines and Bayesian classification.

The three weights output from the thresholder are combined, such as by summing the weights, in the processing of the flow disturbance calculator 1312 to produce a flow disturbance feature. The processing of the flow disturbance calculator 1312 further compares the weight of the disturbance feature to an arousal threshold, which may be chosen empirically, to indicate whether or not the disturbance feature represents an arousal event. If it does, an arousal flag is set.

Based on the positive indication of the arousal flag, the flow data associated with arousal event is evaluated by the preceding event classifier 1314, to identify particular events that may have led to or caused the arousal. For example, the identified preceding event may be respiratory related (e.g., an obstructive or central apnea event, an obstructive or central hypopnea event, or a flow limitation event) or non-respiratory related (e.g., a Periodic Leg Movement (PLM) event and/or a Leak event (e.g., mouth leak or high leak)). If none of these events are found, then the arousal may be classified as a spontaneous arousal. In some embodiments, the processing for identification of these preceding events may be integrated with the processing of the classifier 1314. However, as illustrated in FIG. 13, they may also optionally be implemented by discrete detectors that communicate the detection results to the classifier 1314. Finally, the arousal detector 114 will output the arousal feature, which may be a signal or data indicating the type and/or duration of the arousal. For example, it may be identified as a mouth leak related arousal, an apnea related arousal, a flow limitation related arousal, a PLM related arousal, a spontaneous arousal, etc. The duration of the arousal may be determined as the time period from which the arousal flag is set to indicate the arousal until the time it changes to indicate that no arousal is occurring. Alternately, the time period may be a number of breaths.

K. Sleep Stability Detection Module

In some embodiments of the technology, the implemented sleep stability detection module 116 may be implemented with multiple functions. For example, in conjunction with the arousal detection module, the module may (1) classify a detected flow disturbance, (2) grade the level of flow disturbance intensity (e.g., a degree of the arousal) and/or (3) infer a level of autonomic activation.

Figure 8:
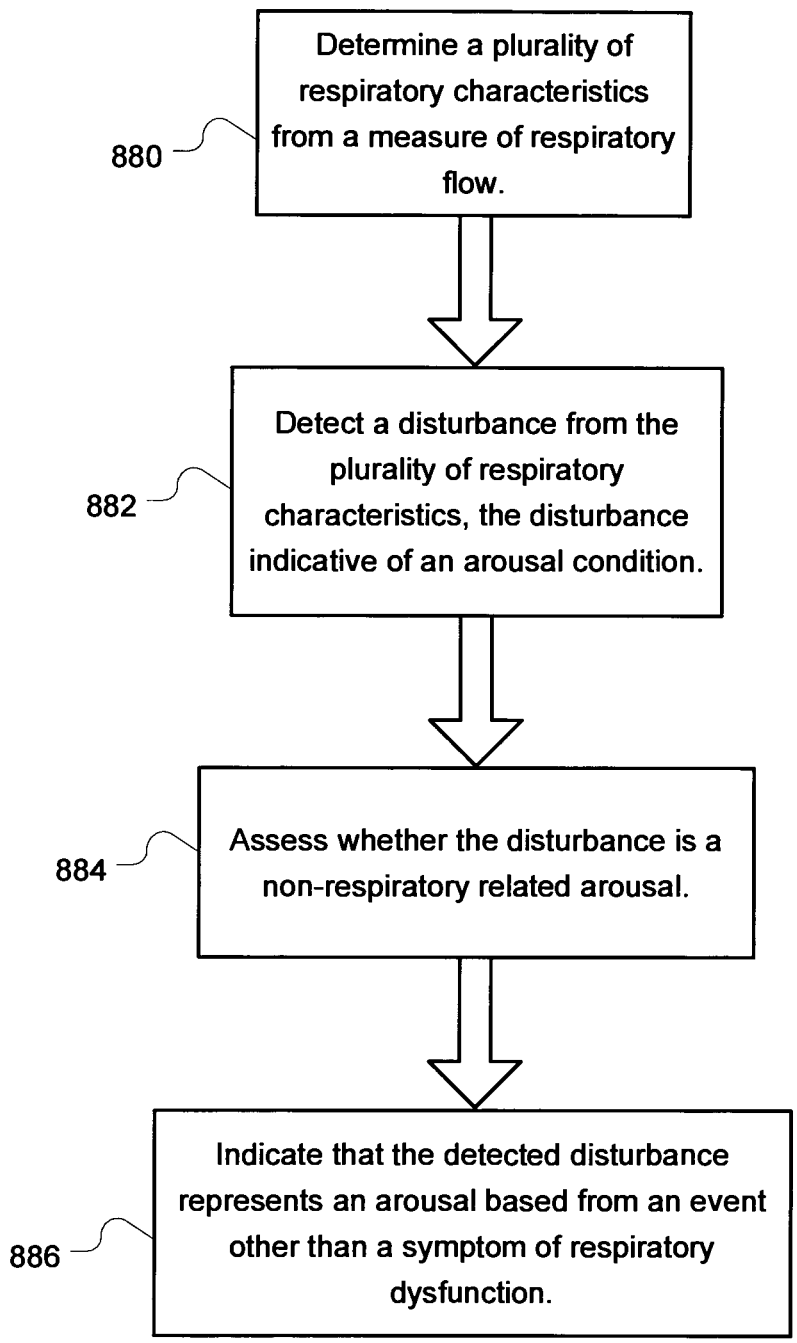
FIG. 8 is a flow diagram of an example embodiment of a methodology for controlling an apparatus to detect a non-respiratory related arousal with data from a flow sensor.

An example methodology associated with the arousal detection module 114 and sleep stability detection module 116 is illustrated in FIG. 8. Essentially, the modules may be implemented with a methodology to detect or classify a sleep arousal condition from data representing a measured flow of breathable gas. At 880, the methodology may include determining a plurality of respiratory characteristics from a measure of respiratory flow. This may be integrated with the detection modules or provided from another module such as the feature extraction module 110. At 882, a disturbance is detected from the plurality of respiratory characteristics as previously discussed. The disturbance may be indicative of an arousal condition. Optionally, at 884, as discussed in more detail herein, the methodology may assess whether the disturbance is a non-respiratory related arousal. At 886, the module may then indicate that the detected disturbance represents an arousal based from an event other than a symptom of respiratory dysfunction. For example, it may store data representing the determination in memory, apply it to the input of another module (e.g., the sleep quality module 120) and/or produce it as output such as on a display of the user interface module 124. Such a non-respiratory dysfunction related event may be, for example, an event associated with a periodic leg movement. Thus, the detected non-respiratory arousal may be attributed to a periodic leg movement or detected leak. In other words, one or more occurrences of periodic leg movement or a period of periodic leg movement may be identified from detecting arousals or disturbances and detecting a contemporaneous or synchronous absence of respiratory dysfunction symptoms (e.g., no or insignificant flow limitation, no or insignificant flow flattening, no or insignificant obstruction etc.).

Figure 9:
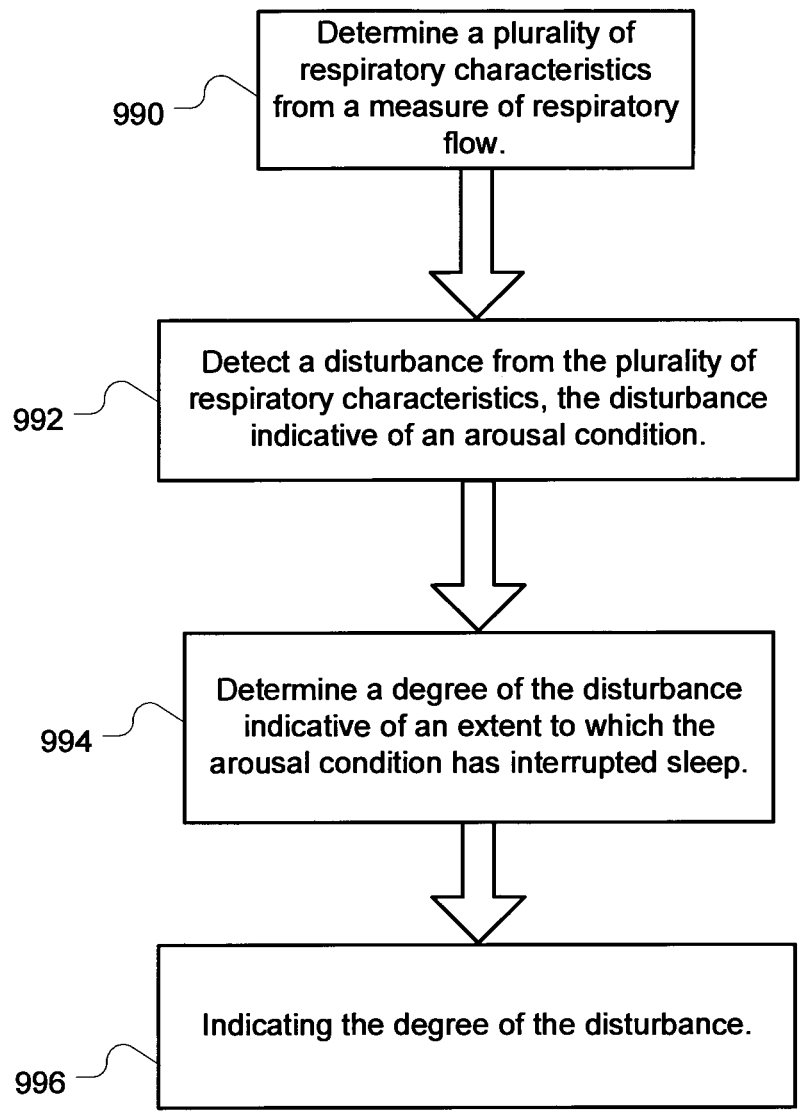
FIG. 9 is a flow diagram of an example embodiment of a methodology for controlling an apparatus to detect a sleep stability measure with data from a flow sensor.

A further example methodology associated with the arousal detection module 114 and sleep stability detection module 116 is illustrated in FIG. 9. Essentially, the modules may be implemented with a methodology to assess sleep stability from a measured flow of breathable gas. At 990, the method may include determining a plurality of respiratory characteristics from a measure of respiratory flow. This may be integrated with the detection modules or provided from another module such as the feature extraction module 110. At 992, a disturbance is detected from the plurality of respiratory characteristics, which may be indicative of an arousal condition, as previously discussed. At 994, a degree of the disturbance is determined. The degree of the disturbance may be indicative of an extent to which the arousal condition has interrupted sleep. The processor may then indicate the degree of the disturbance. For example, it may store data representing a calculated degree of disturbance in a memory, apply it to the input of another module (e.g., the sleep quality module 120) and/or produce it as output such as on a display of the user interface module 124.

In the following example embodiment, the flow disturbance is classified, graded and then also used as an index to infer a level of autonomic activation for the patient. In this embodiment, the following steps may be implemented:

(1) Receive Flow Disturbance Data Packet from Arousal Detector;

This may optionally occur where the module does not itself process the measured flow signal to detect the disturbance.

(2) Analyze Data of the Period Prior to Occurrence of the Flow Disturbance of the Data Packet to Classify the Disturbance.

For example, if there have been detected respiratory events such as apneas or hypopneas just prior to the flow disturbance, the disturbance of the packet may be regarded as a respiratory related arousal. If no such event has occurred prior to the flow disturbance, it may be classified as non-respiratory such as an arousal attributable to periodic leg movement rather than a respiratory dysfunction.

Optionally, if a leak has also been contemporaneously detected by the leak detection module 112, the device may classify the arousal or disturbance as non-respiratory but attributable to a valve-like leak of the mask.

(3) Calculate the Length (e.g., Duration) and Intensity of the Flow Disturbance.

For example, the length of the disturbance may be a determined or calculated duration or time taken for the disturbance (e.g., seconds or minutes). In addition to determining the length, in some embodiments, the intensity (e.g., degree of the disturbance) may be determined. For example, an intensity value may be calculated as a ratio of the disturbance data and respiratory breath data prior to the disturbance. For example, the intensity value may be calculated as a ratio of (a) a variance of the flow disturbance section of the data packet (e.g., samples from the flow signal during the flow disturbance) and (b) a variance of the flow data for a number of breaths (e.g., 15 breaths) prior to the disturbance (e.g., samples from the flow signal prior to the flow disturbance). Any of the respiratory characteristics may also be utilized in the calculation of such a ratio.

Optionally, the determined intensity value may be utilized to imply autonomic activation for the patient during the disturbance. For example, the module may include or have access to a memory with a look-up table. The look-up table may contain data mappings of flow disturbance intensities to levels of autonomic activation (e.g., values for heart rate variability, values of pulse transit time (PTT), etc.). Thus, the intensity may be utilized as an index to a autonomic activation value. Optionally, the table may be further indexed by data processed by the patient characteristics store module 122. In such a case, the table may include data for different classes of patients. Thus, the determination of inferred autonomic activation may be further indexed according to particular patient characteristics, such as the age, body mass index (BMI), weight, height, and/or other disease condition or current physiological condition, etc. for the particular patient utilizing the device. Such a table may optionally be developed through a large scale data mining exercise to compare and associate flow disturbance intensities and subsequent autonomic changes (e.g., Heart Rate Variability (HRV) and Pulse Transit Time (PTT)) in different classes of patients.

(4) Indicate Sleep Stability Score to Sleep Quality Index Module.

The intensity value, length, autonomic activation values, type of disturbance identified, etc. may optionally be stored in a memory of the device, used by other assessment modules (e.g., the sleep quality assessment module 120) and/or displayed on a visual output display of the user interface module 124.

In sum, an objective of respiratory treatment (e.g., positive airway pressure) therapy is to reduce respiratory related disturbances for a patient, and thereby increase sleep stability. Thus, embodiments of the sleep stability detection module quantify a level of sleep related disturbance that occurs during the patient's sleep session. For example, a detector with such a module may generate a score between 0 and 1 at the end of each breath cycle indicating the level of sleep disturbance. In such a case, a score of 1 can indicate maximum sleep stability. The score may then grade progressively lower levels of sleep stability as the score decreases to 0.

To this end, in some embodiments, by applying some or all of the features determined by the feature extractor 106 to one or more threshold functions, a weight may be applied to each feature. Optionally, these threshold functions may be adjusted by some or all of the patient characteristics from the patient characteristics data 122. A respiratory disturbance value may then be calculated from the weighted outputs of the threshold function(s). This value may then be de-weighted by outputs from the leak detection 112 and arousal detection modules 114 discussed herein. A sleep stability score may then be calculated as a rolling average of the de-weighted values determined over a number of breaths (e.g., a range of about 5 to 30 such as a 15 breath rolling average).

Example Sleep Stability Detector Embodiment

Figure 15:
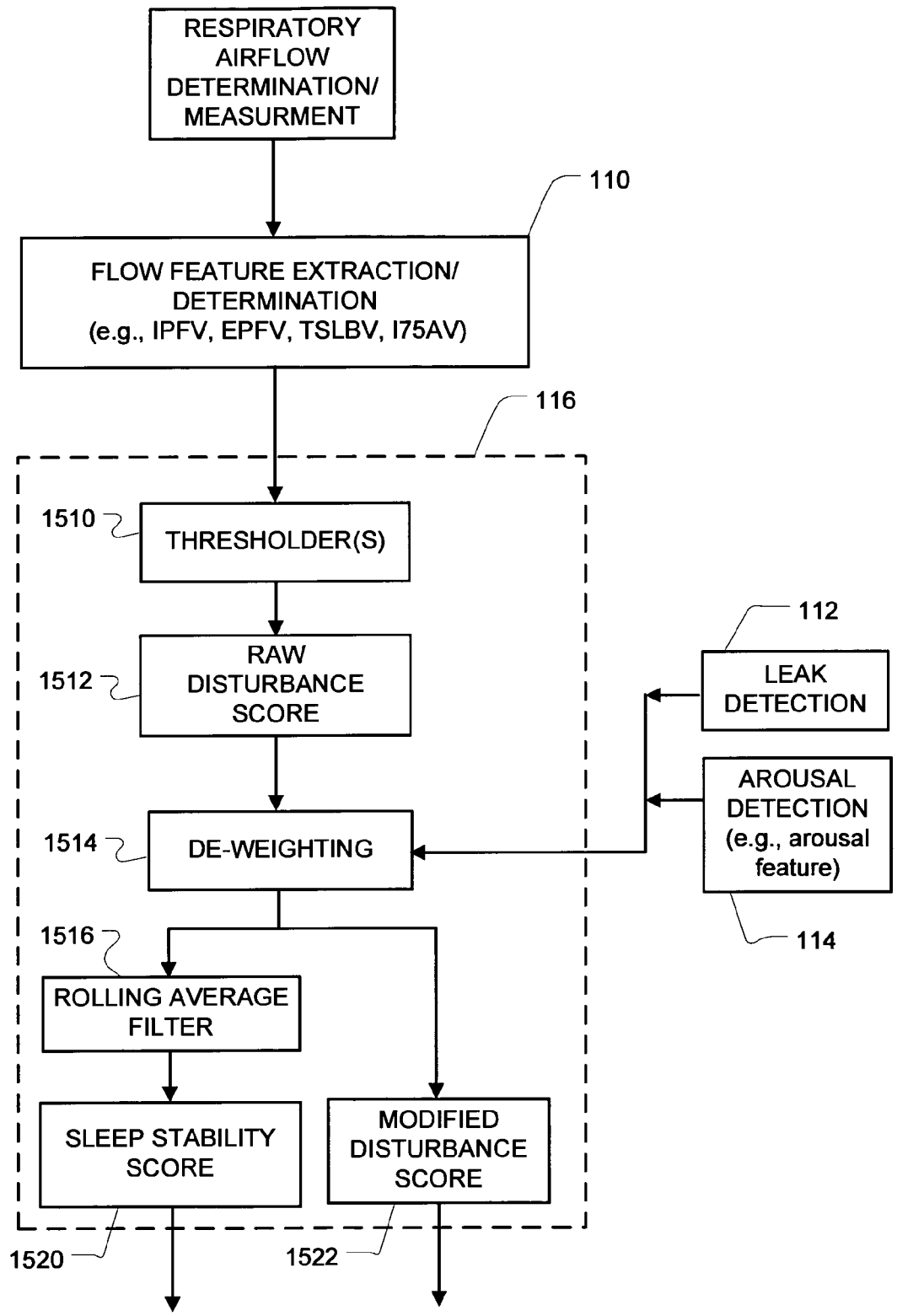
FIG. 15 is a block diagram illustrating processing methodologies of an example sleep stability detection module in some embodiments of the technology.
Figure 16:
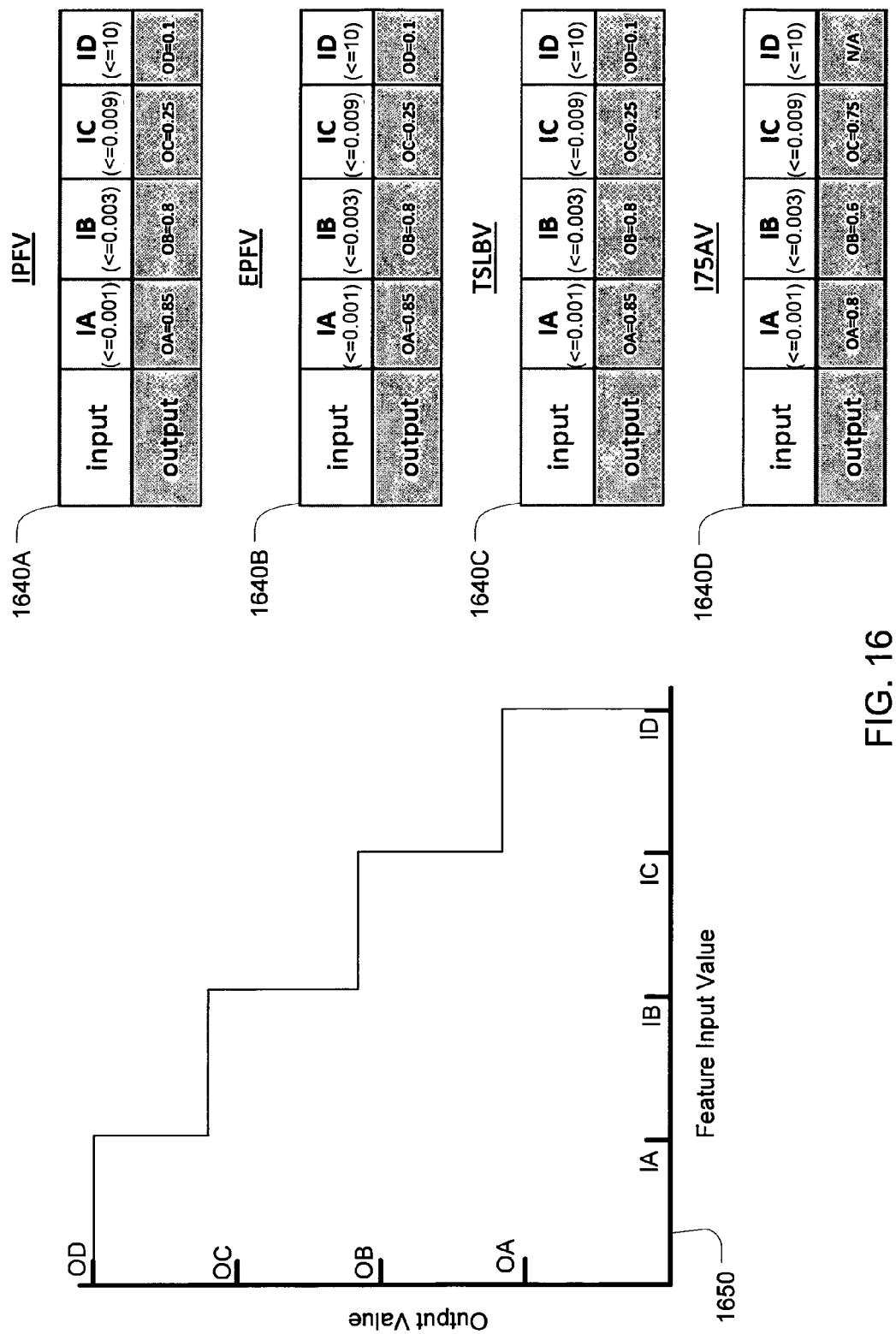
FIG. 16 shows a graph of an example function for adjusting sleep stability scoring to account for leak in an example sleep stability detector.

Such an example embodiment of the sleep stability detection module 116 may be configured with the processing illustrated in the block flow diagram of FIG. 15. In the example, a respiratory airflow or filtered flow associated with a flow sensor of a flow generator is provided to and processed by the feature extractor. In this process, a particular subset of the previously described respiratory features determined by a feature extractor are utilized. This subset of features may optionally only include the IPFV (i.e., Inspiratory Peak Flow Variation) feature, the EPFV (i.e., Expiratory Peak Flow Variation) feature, the TSLBV (i.e., Time Since Last Breath Variation) and the I75AV (i.e., Area above 75% Inspiratory Peak Flow Variation) feature, which are each previously discussed. Each feature is provided to a thresholder 1410 where one or more threshold function(s) such as the examples illustrated in FIG. 16 are applied to each feature of the feature subset. Although this example uses particular features, it will be understood that other embodiments may be based on other sets (e.g., all features) or subsets with any combination of the previously mentioned respiratory flow based features determined by the feature extractor.

In the example, when thresholding of the IPFV feature, the function of graph 1650 of FIG. 16 may be implemented with the example input values IA, IB, IC and ID and example output values OA, OB, OC and OD taken from table IPFV (shown as table at reference character 1640A). As previously mentioned in the tables, the input values IA, IB, IC etc. represent consecutive ranges for the output values. Thus, for table IPFV, IA is a range from less than 0.001 up to and including 0.001. IB is a value of a range greater than the range of IA up to and including 0.003. IC is a value of a range greater than the range of IB up to and including 0.009. ID is a value of a range greater than the range of IC up to and including 10, which may be considered a maximum possible input value. For example, in the case IPFV feature having a determined value of 0.003, an output value, which may be considered a disturbance weight, of 0.8 is selected as the output that is attributable to the IPFV feature. Similarly, output weights are selected for the EPFV feature. However, in the case of the EPFV feature, the input and output values for function of graph 1650 will be based on the values of the EPFV table (shown as table at reference character 1640B). Similarly, output weights are selected for the TSLBV feature by the function of graph 1650 and based on the values of the TSLBV table (shown as table at reference character 1640C). Similarly, output weights are selected for the I75AV feature by the function of graph 1650 and based on the values of the I75AV table (shown as table at reference character 1640D). It is noted that although specific values are illustrated in the tables of FIG. 16 it will be understood that these are merely examples. Other values may be implemented and may be empirically determined either from a group of patients or for a particular patient. Thus, these values may be learned with processing based on machine learning and pattern recognition techniques. Examples of techniques that may be adopted for this include cluster analysis, support vector machines and Bayesian classification.

A raw disturbance score is then determined by combining the weights, such as by summing the weights from thresholder 1510 in the raw score processing at scorer component 1512. The raw score from scorer component 1512 may then be adjusted or de-weighted based on certain system conditions. For example, it may be adjusted based on a detected leak and/or arousal conditions from a leak detection module or arousal module as illustrated in FIG. 15.

Figure 17:
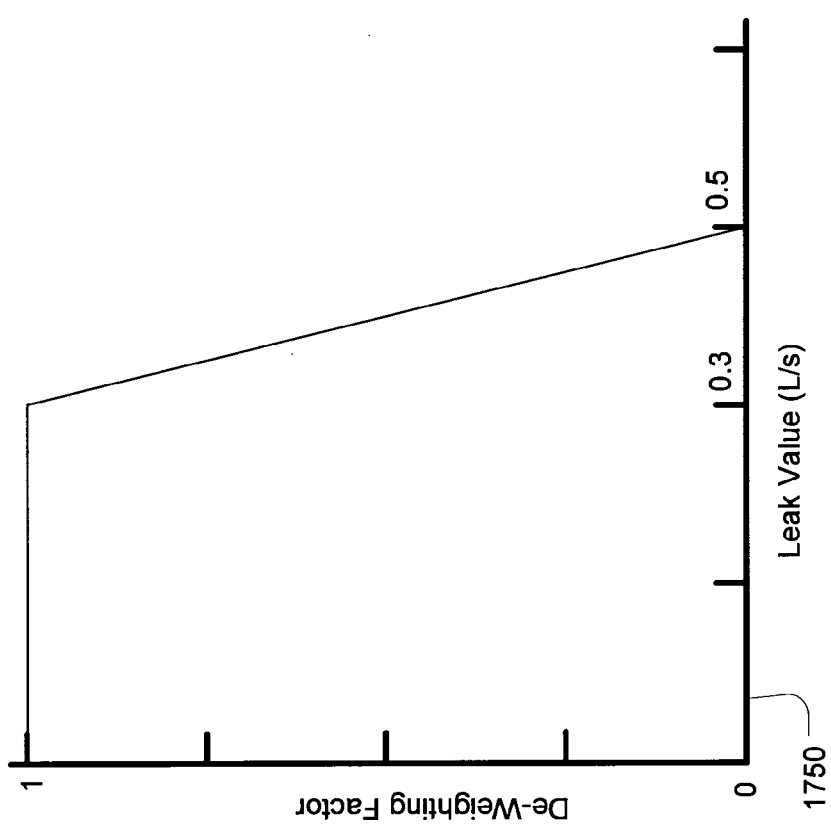
FIG. 17 shows an example graph of a generic threshold function with example input and output values for thresholding features in an example sleep stability detector.

For example, a modified disturbance score 1522, which is from a current breath, may be determined by de-weighting the raw disturbance score by a de-weighting factor determined from a de-weighting function such as the example function illustrated in FIG. 17. Thus, the function of FIG. 17 may be employed to take into account current leak levels. In the example, if there is a high level of leak (e.g., leak greater than about 0.4 l/s) in the system determined by the high leak detector, the signal-to-noise ratio (SNR) for the actual respiratory airflow signal may be greatly reduced. In such situations the raw disturbance score may be de-weighted to take into account this low SNR. The threshold of FIG. 17 linearly de-weights the sleep stability using the output de-weighting factor once leak levels reach 0.3 l/s. Once leak reaches 0.5 l/s, the Sleep Stability score will be 0.

Similarly, the de-weighting component may be employed to consider the current arousal status from the arousal detector. For example, respiratory, leak and PLM related arousals are disruptive to the patient's sleep and the sleep stability score should be utilized during these types of arousals. However, a detected spontaneous arousal may be considered a part of the natural sleep pattern of the patient. In such a case, a determined sleep stability score for a particular breath may be disregarded if it coincides with a detected spontaneous arousal. Therefore, the de-weighter 1514 may assess the input arousal feature, and if a spontaneous arousal is detected, it may be configured to prevent the modified disturbance score from being counted in the sleep stability score for the current breath.

A filter 1516, such as a rolling average filter, may then process the modified disturbance scores from the de-weighter 1514. For example, the output of the de-weighter may be averaged over a past number of determined scores, such as a number in a range from 10 to 20 scores, but preferably 15. Finally, the output of the filter may be considered the sleep stability score 1520 which may be considered a sleep stability index.

L. Sleep Quality Assessment Module

Figure 10:
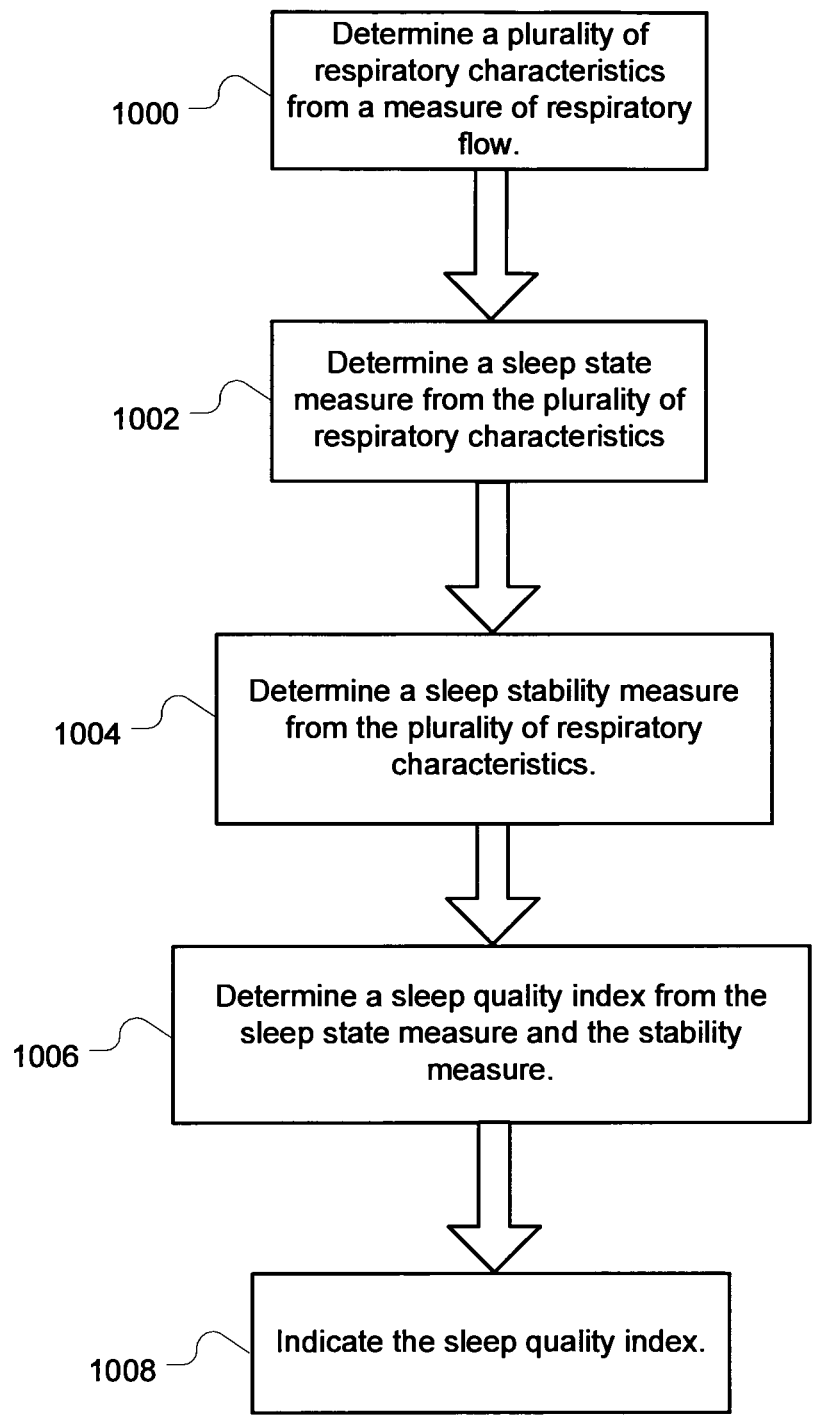
FIG. 10 is a flow diagram of an example embodiment of a methodology for controlling an apparatus to detect a sleep quality measure with data from a flow sensor.

A sleep quality assessment module 120 may be implemented to assess sleep quality. In some embodiments, the assessment or detection may be based on outputs of other modules. An example methodology associated with the sleep quality assessment module 120 is illustrated in FIG. 10. Essentially, the methodology determines a sleep quality indicator from a measured flow of breathable gas. At 1000, similar to the input of the prior modules, a plurality of respiratory characteristics from a measure of respiratory flow are determined. This may be integrated as part of the module or as part of another module (e.g., the feature extraction module 110). At 1002 and 1004 respectively, the method then involves a determination a sleep state measure and a sleep stability measure from the plurality of respiratory characteristics as previously discussed. At 1006 and 1008 respectively, the method then determines and indicates one or more a sleep quality index/indices from the sleep state measure and the stability measure. Thus, the index or indices may be stored in a memory of the device, used by other assessment modules (e.g., the feedback module 126) and/or displayed on a visual output display of the user interface module 124.

For example, an embodiment may be implemented with the following steps:
(1) Calculate a length of a sleep period (e.g., REM, non-REM, Deep REM, Light-REM, Phasic REM, Tonic REM, All Sleep States, etc.) as an index;
(2) Calculate a ratio between levels of sleep stability and total sleep time as an index; For example, a sleep stability index may be divided by a total sleep time index. This may serve to normalize the stability index.
(3) Weight this ratio using the length of awakening periods during the night as an index; Such a step may take into account the frequency of awakenings. For example, collectively the total awake time might be a figure X. However if this figure is made up of Y small awake periods and this figure Y is large, then they can be accounted for by the weighting factor. In other words, the sleep stability figure may be further normalized by the frequency of awakenings during the night.
(4) Weight the ratio to account for bias as a result of individual patient characteristics as an index; In some cases there may be a certain level of bias towards increased periods of an awake state. A weighting factor based on such a bias that is attributable to entered characteristics of a particular patient may be utilized to further normalize the ratio.
(5) Output a final sleep quality score as a set of indices.

Optionally, this module may also monitor or record as an index a number of breakdowns of awake to sleep periods from one night to the next for feedback purposes. Such a figure or figures can be a simple number that can be calculated as the number of Awake periods, the total awake time, the number of sleep periods and/or total sleep time. Optionally, this can be provided as a figure(s) averaged over a period of time such as a month. A day by day figure(s) may also be provided. Such information can provide some simple feedback to the patient about their sleep architecture.

The output of this module may be recorded, used for feedback purposes and/or displayed for the patient and/or a clinician. For example, it may be displayed through the user interface module 124 and/or returned or fed back into the therapy algorithm processing module 128 to implement adaptive control of a flow generator in real time. The feedback may serve to implement short term changes to therapy and/or longer term changes (e.g., weeks or months).

Example Sleep Quality Detector

A further example embodiment of a sleep quality assessment module 120 may be considered in reference to FIGS. 28 to 31. Generally, the processing in this sleep quality detector will involve an assessment of other processed data of the system such as the sleep stability index, the sleep state identifier and/or the arousal index. The input data can serve as a dynamic force(s) to change the sleep quality index (SQI) on a breath-by-breath basis. The processing of the assessment module is illustrated in the block diagram of FIG. 28. In this embodiment, the input data are applied to thresholders 2810A, 2810B and 2810C.

Figure 29:
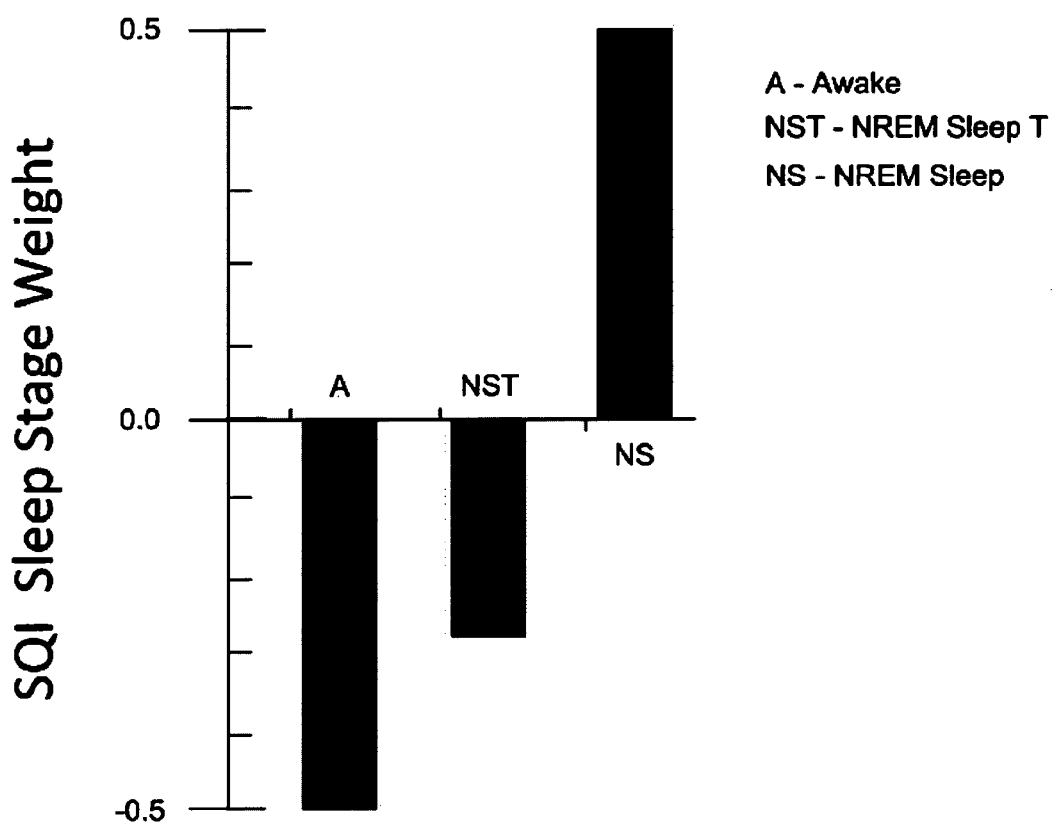
FIG. 29 is a graph illustrating a sleep state thresholding function for the sleep quality assessment module of FIG. 28.

In the event that the assessment module processes the sleep state identifier, thresholder 2810A may be implemented with a function such as the function illustrated in FIG. 29. In this case, the output of the thresholder 2810A may be a weight in a range of −0.05 and 0.5 based on the sleep state identifier. Generally, the function of FIG. 29 indicates that NREM Sleep will have the highest positive influence while Awake will have the highest negative influence. In this regard, if the input state identifier represents the Awake State 2110, then the output weight is −0.5. If the state identifier represents the NRem Sleep T state 2116, then the output weight is −0.3. If the state identifier represents the NRem Sleep state 2114, then the output weight is 0.5. In the case that the state machine includes additional detected states, additional weight values may be implemented by the thresholder.

In still further embodiments, detection of a REM state may also result in an adjustment to the sleep quality index. For example, if REM state periods are detected, then the sleep quality index may be positively weighted. Thus, in some embodiments, the sleep quality index may be increased as a function of a length of overall time spent in one or more REM states. Optionally, it may be increased as a function of an increase in a number of REM periods detected. Still further, it may be increased as a function of a particular point in time of the nights sleep that the REM state detection occurs. In still further embodiments, detection of REM state(s) may not result in any adjustment to the sleep quality index.

Figure 30:
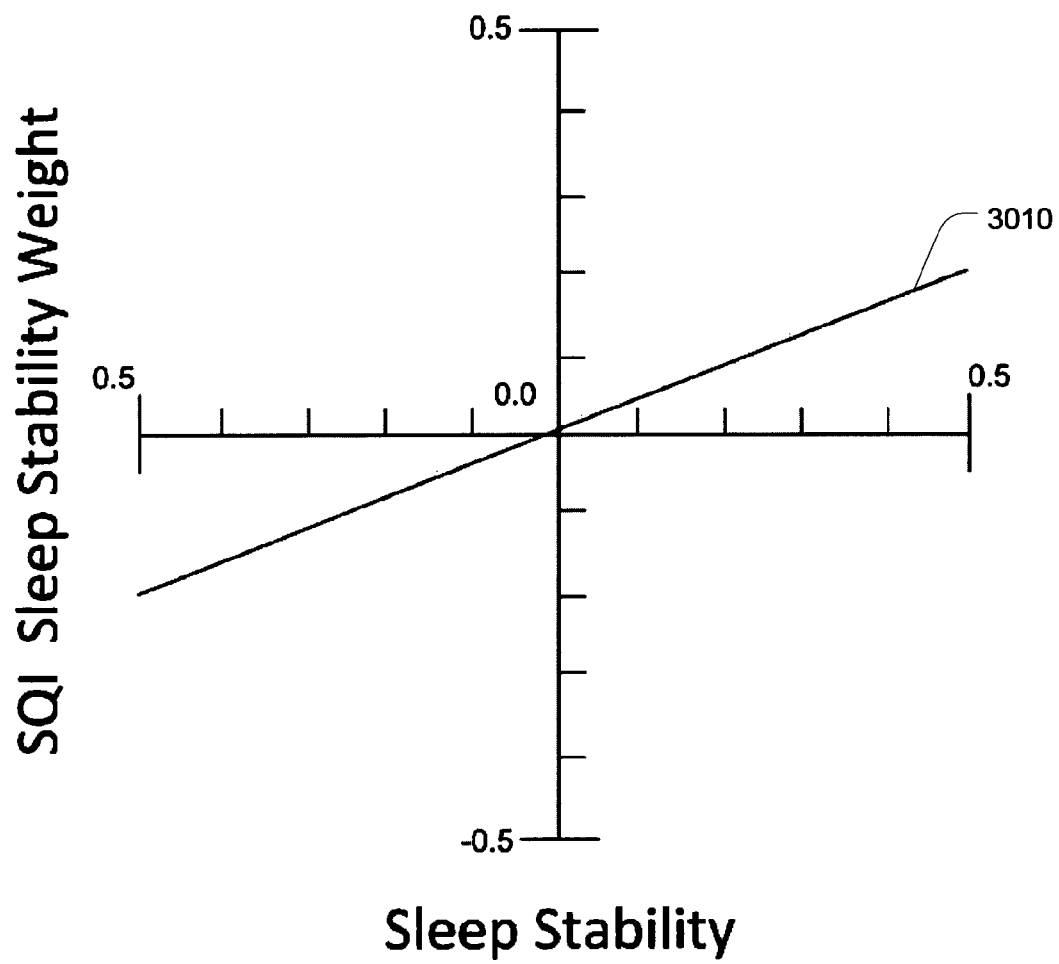
FIG. 30 is a graph illustrating a sleep stability index thresholding function for the sleep quality assessment module of FIG. 28.

In the event that the assessment module processes the sleep stability index or sleep stability score, thresholder 2810B may be implemented with a function such as the function illustrated in FIG. 30. In this case, the output of the thresholder 2810B may also be a weight in a range of −0.05 and 0.5 based on the sleep stability index. The association between the input sleep stability index and the output weight is represented by function line 3010. For example, an input of a sleep stability index of about 0.3 may result in an output weight of about 0.1.

Figure 31:
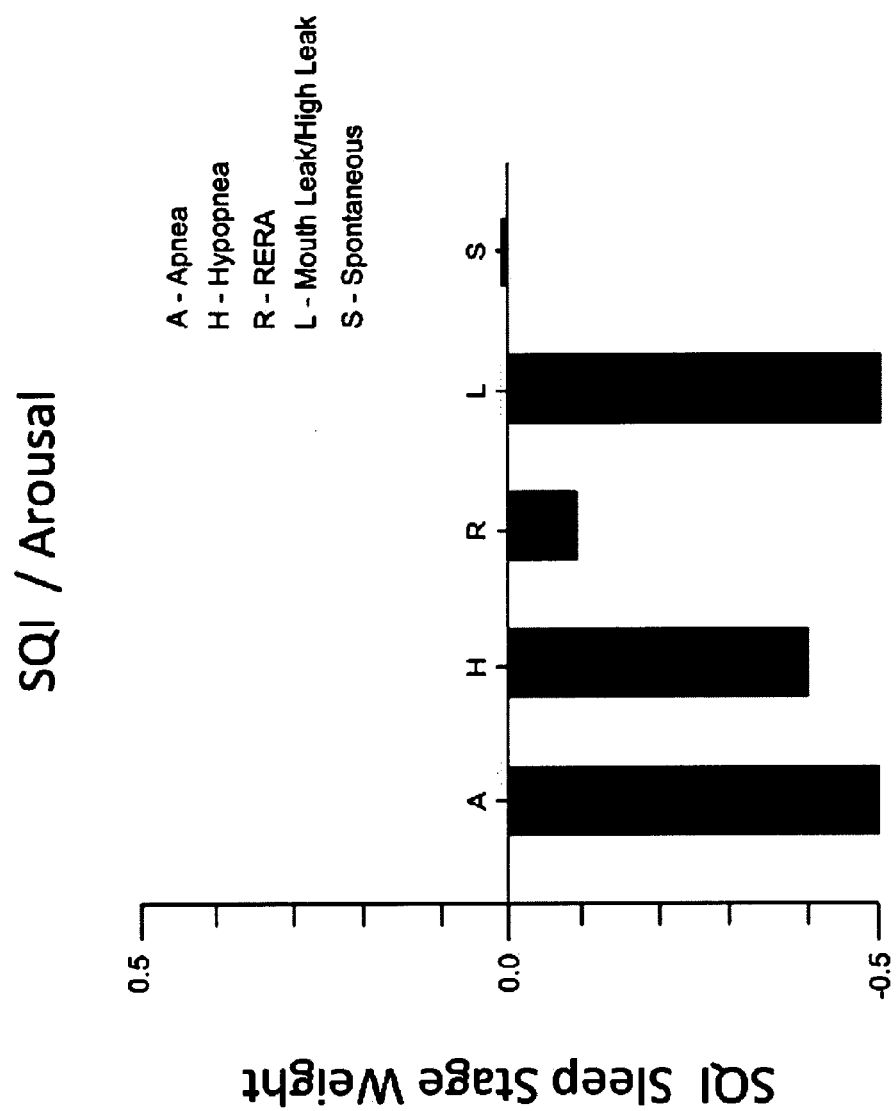
FIG. 31 is a graph illustrating an arousal data thresholding function for the sleep quality assessment module of FIG. 28.

In the event that the assessment module processes the arousal data, such as the arousal type, thresholder 2810C may be implemented with a function such as the function illustrated in FIG. 31. In this case, the output of the thresholder 2810C may also be a weight in a range of −0.05 and 0.5 based on the sleep stability index. In this regard, if the input arousal type represents an apnea, then the output weight is −0.5. If the input arousal type represents an hypopnea, then the output weight is −0.4. If the input arousal type represents a RERA (respiratory effort related arousal), then the output weight is −0.1. If the input arousal type represents a leak, such as a mouth leak or high leak, then the output weight is −0.5. Finally, if the input arousal type represents a spontaneous arousal, then the output weight is 0.

Based on the output of the thresholder(s), the sleep quality adjuster 2812 then sets the sleep quality index, which may be a real value between 0 and 1. For example, an existing sleep quality index may be raised or lowered by applying the weights of the thresholders as factors to a sleep quality index. For example, a sleep quality index may be reduced by multiplication with a negative weight factor or increased by multiplication by a positive weight factor. Alternatively, the thresholders may simply output true or false values if the threshold function is positive or negative respectively based on the input data. The true or false values may then control respectively incrementing or decrementing a sleep quality index, such as an integer value. This assessment may generally be based on the premise that (a) certain arousals will generally decrease sleep quality whereas an absence may increase sleep quality, (b) a decrease in sleep stability will decrease sleep quality, and (c) some sleep states will be indicative of better sleep quality.

In the above described functions of FIGS. 29-31, the weights have been chosen to permit output of a sleep quality index that may be between 0 and 1 as a suitable indicator of sleep quality where 1 is the best quality and 0 is the lowest quality. However, other weight values and indicator values may be chosen depending on the nature of the desired sleep quality index.

M. Feedback Control Module

Thus, in some embodiments, the output of these modules of the system may serve to control changes to a therapy control algorithm, such as a pressure treatment therapy (e.g., continuous positive airway pressure therapy ("CPAP")) provided by a processor controlled flow generator. For example, sleep quality assessment output or sleep state output may be fed back into a feedback control module 126. The feedback control module may then control, for example, a level of instantaneous and long term amounts of pressure therapy given to the patient. This feedback control module may implement dynamic or short term and/or static or long term changes to the delivered therapy by sending instructions or control signals to a flow generator or therapy control processing module 128.

In one example, a dynamic feedback control may be based on different sleep state outputs. For example, if a patient is initially in a detected awake state, delivered therapy may be kept at minimal levels. Similarly, the respiratory detection routines (e.g., AHI module) may be set to be disabled or otherwise be weighted to be less sensitive to any flow disturbances and otherwise avoid or minimize the making of pressure adjustments to treat AHI events. As the patient transitions into a detected sleep state, the feedback control module may set the controller to be more sensitive to flow disturbances or AHI events. In periods of detected deep sleep (e.g., a deep REM state or REM state), the sensitivity levels of the pressure therapy algorithm may be set at its maximum to fully treat/respond to detected events. Still optionally, if the device detects a patient waking up with a detected arousal and/or awake state, the therapy may then be ramped down or decreased at gradual steady rate to permit the patient to more comfortably return to sleep.

In some embodiments, the feedback control module may implement static changes to therapy control. For example, a sleep quality index may be used for long term feedback. As the patient's sleep patterns change over time as monitored by changes to sleep quality indices, the sensitivity levels of the therapy algorithm may be adjusted accordingly. For example, improvements in sleep quality indices may control a reduction to therapy levels. Similarly decreases in sleep quality indices may control an increase in therapy levels. Such long term changes may optionally be implemented at controlled time periods, e.g., only after a certain number of treatment sessions, at the beginning of each month, or a period of therapy equivalent to a month, etc.

In still further embodiments, an additional awake to sleep breakdown score may also be implemented to control changes to the therapy. For example, if there is a larger or increasing proportion of awake periods over a long term period (e.g., 1 month) then the pressure control algorithms may be weighted by a factor based on the score to provide a greater degree of therapy.

The following additional feedback example embodiments may be implemented based on the output of the aforementioned modules.

A. Awake Expiratory Pressure Relief (EPR)

In some respiratory pressure treatment devices, pressure control may include an Expiratory Pressure Relief (EPR) feature. Such a device is described in International Patent Application No. PCT/US2004019598 (Publ. No. WO 2004/112680) and corresponding U.S. Pat. No. 7,128,069, the disclosure of which is incorporated herein by reference. An EPR feature can provide patient comfort to allow a patient to achieve sleep more easily. Generally, the EPR control automatically reduces a delivered treatment pressure by some amount (e.g., cm $H_2O$) from a therapeutic pressure treatment setting upon the detection of each patient expiration while delivering the therapeutic treatment pressure during inspiration. Such a pressure treatment control may be modified based on the current technology. Typically, once a patient is asleep, EPR may be considered less necessary for treatment of the patient in that EPR may not provide maximum desired therapeutic benefit to the patient. Accordingly, a ramp time may be implemented based on the detected sleep state which may in turn control the EPR. For example, whenever the device detects that that patient is in the Awake state, the EPR control may be turned on or otherwise operate as described above to reduce pressure during expiration. However, once the sleep state detection module detects that a patient falls into either NREM Sleep T, NREM Sleep or REM Sleep, the EPR function may be disengaged to prevent the reduction during expiration. Optionally, the EPR control function may be gradually disengaged by gradually ramping down the amount of reduction of the therapeutic treatment pressure during a number of breathing cycles or period of time upon the detection of a transition from an awake state to a sleep related state. While this disengaging of the EPR function may be implemented at sleep onset, it may even optionally be implemented dynamically throughout a treatment session. For example, if after the sleep onset, the sleep state detection module detects that the patient has returned to an awake state from a sleep state (for example, by entering an awake state and remaining there for a certain period of time), the EPR function may be reengaged (or gradually re-engaged by gradually ramping up the amount of reduction of the therapeutic treatment pressure during a number of breathing cycles or period of time). The EPR may then subsequently be disengaged (e.g., gradually) as discussed above upon the further detection of patient's sleeping state.

B. Respiratory Event Reporting

In some embodiments, the sleep state detection may control how detected events are scored. For example, some events that may be detected by the respiratory treatment apparatus may not be reported as part of an event score even though these are detected by the device. For example, detected respiratory events such as apneas, hypopneas, arousals, mask leak, and/or mouth leak may not be reported as part of a particular event type score if the event is detected concurrently with a detected awake state. In such a case, the control algorithm of the treatment device may confirm that the patient is in NREM Sleep T, NREM Sleep or REM Sleep states before the detection algorithm will score such events. Optionally, all of the events may be scored but the scoring of each of the events may be categorized based the different detected sleep states during which they occurred or even more simply whether they occurred during either awake or sleep time. For example, a number of apneas may be scored for the awake time of a treatment session and a number of apneas may be separately scored for the sleep time (e.g., the sleep related states) of the treatment session. Thus, the scored events may be reported as output by the device based on the detected states such as in association with the detected sleep state during which they occurred.

C. Therapy Change Control.

In some respiratory treatment apparatus, a therapeutic treatment pressure may be automatically set by the device. For example, some pressure treatment devices may analyze the respiratory flow signal for abnormalities in the patients breathing and adjust the pressure for treatment of the abnormalities. For OSA patients, these abnormalities may be considered Flow limitation, Snoring and Obstructive Apneas. Once the pressure treatment device detects one or more of these events, it will control an increase in the pressure therapy based on the severity of the event up to some predefined maximum. In some such pressure treatment devices, after such an increase, if the abnormalities in the flow are removed (i.e., no longer detected), the device can automatically control a reduction in the pressure therapy to permit it to fall back down to some predefined minimum value (e.g., set by the doctor for the patient). However, in some cases this may not be the most desirable scenario because events can occur in quick succession and this quick succession can result in the pressure therapy being increased and decreased unnecessarily. Accordingly, with aspects of the present technology, such a pressure control algorithm may be modified. For example, the pressure control algorithm may be configured to treat the detected abnormalities and, rather than simply reducing the pressure in the further absence of detecting these abnormalities, the control may hold the therapy at the raised treatment level until the aforementioned sleep stability index is restored to a "high/acceptable" level based on comparing the sleep stability index against a threshold. Upon reaching the threshold after a treatment pressure increase, the pressure may then be reduced, or gradually ramped down, to the pre-determined minimum. The threshold representative of such a "high/acceptable" level may be pre-determined empirically, for example, by data mining of existing clinical data. Thus, reductions in the therapy pressure setting may be based on the sleep stability index instead of, or in addition to, the absence of the detection of the breathing abnormalities.

D. Assess Cardiopulmonary Coupling (CPC).

CPC is an interesting quantity which measures the coupling between heart rate and breath rate. There are many uses for it but two of the most relevant are being able to distinguish between central and obstructive apneas and also measuring overall sleep quality. The breath is easily derived via the respiratory flow signal. However, deriving heart rate is a bit more difficult. A measure of heart rate from the respiratory flow is done by analyzing the cardiogenic flow element of the overall respiratory flow signal. For example, U.S. Pat. No. 5,704,345 describes several methods for detecting cardiogenic airflow, the disclosure of which is incorporated herein by reference. Cardiogenic flow is small oscillations in the respiratory flow signal due to the pounding of the heart onto the lung. They are not easily distinguishable during all times of therapy. In particular, it can be difficult in Awake, NREM Sleep T and REM Sleep. However, during stable sleep or NREM Sleep it is possible to detect the cardiogenic flow signal more accurately. Accordingly, an automated method for detection of cardiogenic flow may be controlled so as to wait for the detection of a stable section of sleep to occur and during these sections of sleep, the device may then perform the procedure to determine the cardigenic airflow and/or calculate a CPC index. In other words, the detection of particular sleep states (e.g., the NREM sleep state) can trigger or permit the detection of cardiogenic flow while other states (e.g., NREM T, REM or awake) can prevent the cardiogenic airflow determination procedure. Thus, the cardiogenic airflow determination procedure may be based on the sleep state detection. For example, in one embodiment, based on the sleep state, a cardiogenic airflow determination procedure can be used if an apnea is detected to distinguish between obstructive and central apneas. Thus, if a controller of a treatment device detects the onset of an apnea, and the controller detects that the sleep state is a stable state (e.g., the NREM state), a CPC detector, or a process of the controller, may then be enabled to permit a decision on which type of apnea has occurred (e.g., central or obstructive) based on the cardiogenic airflow detection (e.g., the presence or absence of the cardiogenic airflow respectively).

N. Periodic Breathing State Detection Module

Figure 18:
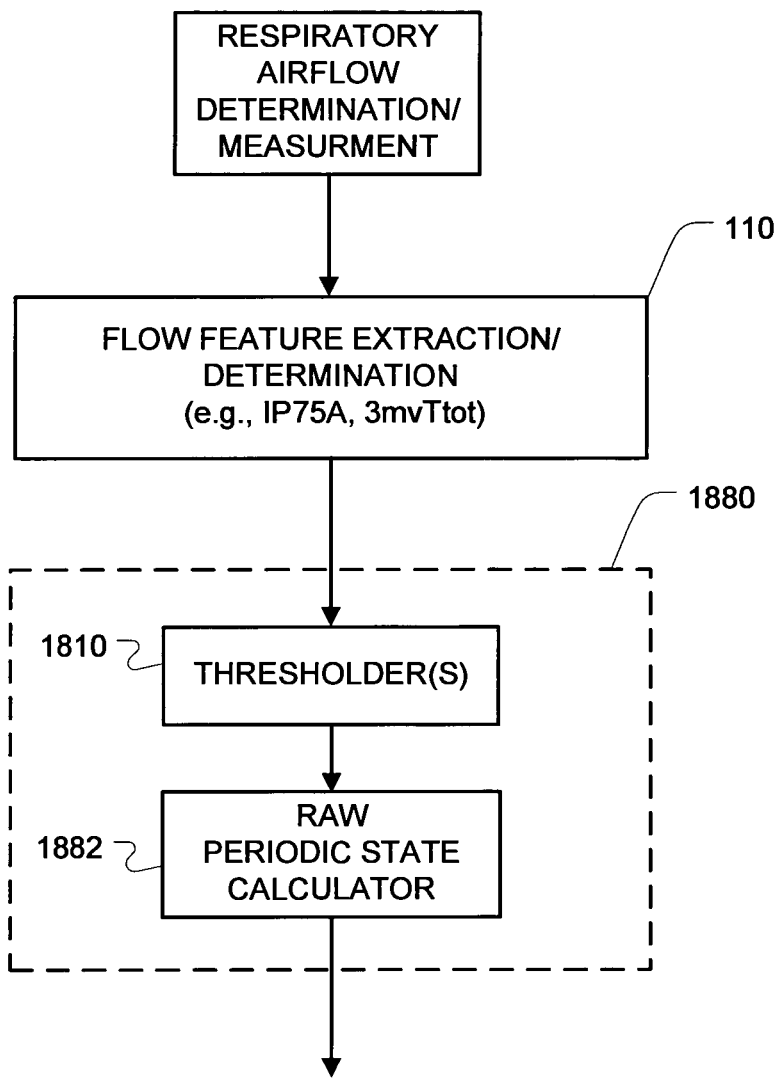
FIG. 18 is a block diagram illustrating processing methodologies of an example periodic breath state detection module in some embodiments of the technology.

In some embodiments, the sleep condition detection device 102 may implement a periodic breathing state detection module 1880 such as the module illustrated in FIG. 18. In this regard, during sleep there may exist sleep sections with high levels of breathing instability. More often than not, this can be periodic nature. In particular, in periods while a patient is transitioning from awake to sleep or periods that follow large arousals, the body's respiratory controller can lose rhythm and in turn cause unstable breathing patterns. A purpose of a periodic breathing state detection module is to identify such sections during sleep. In some embodiments, this may be detected by processing of respiratory flow signal data from a respiratory flow sensor and outputting a periodic breath state output signifying whether or not the patient is experiencing periodic breathing (e.g., a periodic breath state variable is 1 for yes and 0 for no) for a given breath.

For example, such a module may be based on an analysis of one or more of the features of the feature extractor 110 as discussed above. Processing associated with such an embodiment of the module may be considered in conjunction with the details of FIG. 18. Based on a measure of respiratory flow, the feature extractor 110 may determine one or more of the features discussed above. For example, in this example embodiment, the 3mvTtot feature and the IP75A feature may be analyzed. As previously discussed, the IP75A feature is the area of the Inspiratory Flow curve above 75% Inspiratory Peak Flow and the 3mvTtot feature is the ratio between current 3 minute ventilation to Ttot (total breath time).

Figure 19:
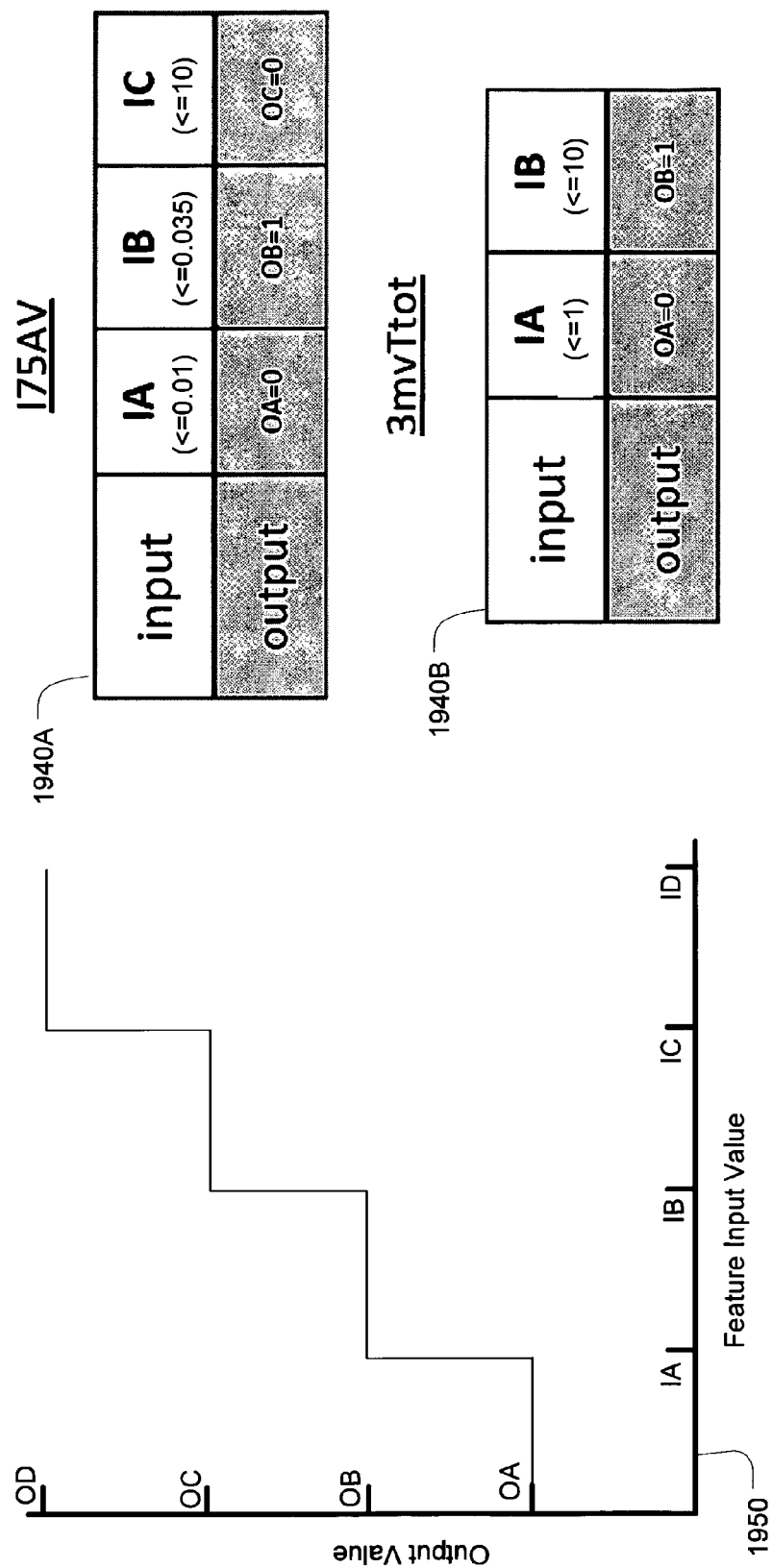
FIG. 19 shows an example graph of a generic threshold function with input and output values for thresholding features in an example periodic breath state detector of the technology.

Each feature is provided to a thresholder 1810 where one or more threshold function(s) such as the examples illustrated in FIG. 19 are applied to each feature of the feature subset. In the example, when thresholding of the I75AV feature, the function of graph 1950 of FIG. 19 may be implemented with the example input values IA, IB and IC and example output values OA, OB and OC taken from table I75AV (shown as table at reference character 1940A). As previously mentioned in these tables, the input values IA, IB, IC etc. represent consecutive ranges for the output values. Thus, for table I75AV (shown as table at reference character 1940A in FIG. 19), IA is a range from less than 0.01 up to and including 0.01. IB is a value of a range greater than the range of IA up to and including 0.035. IC is a value of a range greater than the range of IB up to and including 10, which may be considered a maximum possible input value. For example, in the case I75AV feature having a determined value of 0.035, an output value, which may be considered a periodic state weight, of 1 is selected as the output that is attributable to the I75AV feature. Similarly, output weights are selected for the 3mvTtot feature. However, in the case of the 3mvTtot feature, the input and output values for function of graph 1950 will be based on the values of the 3mvTtot table (shown as table at reference character 1940B). It is noted that although specific values are illustrated in the tables of FIG. 19 it will be understood that these are merely examples. Other values may be implemented and may be empirically determined either from a group of patients or for a particular patient. Thus, these values may be learned with processing based on machine learning and pattern recognition techniques. Examples of techniques that may be adopted for include cluster analysis, support vector machines and Bayesian classification.

These periodic state weights are then processed by the raw periodic state calculator 1882. The raw periodic state score may be determined by the following method:

IF (O_psT1==1) THEN Raw Periodic State=1
ELSE IF (O_psT1==0) AND (O_psT2==1)) THEN
   Raw Periodic State=1
ELSE Raw Periodic State=0

Where:

O_psT1 is the periodic state weight attributable to the I75AV feature;

O_psT2 is the periodic state weight attributable to the 3mvTtot feature.

The periodic state output (e.g., whether or not a periodic breath state has been detected) may then be determined according to the following methodology:

If Raw Periodic State score is 1:
  a. Set Periodic State Output to 1
  b. Increment Periodic State Counter by 1
  c. Set Steady Sleep counter to 0

If Raw Periodic State score is 0, then check if the Steady Sleep counter is less than a Counter Threshold (e.g., in a range from about 5 to 15, but preferably 10)

If Steady Sleep count less than equal to the Counter Threshold (e.g., <=10) then
    a. Set Periodic State Output to 1
    b. Increment Periodic State counter by 1
    c. Increment Steady Sleep counter by 1
  If Steady Sleep count is greater than the Counter Threshold (e.g., >10) then:
    a. Set Periodic State Output to 0
    b. Increment Steady Sleep counter by 1

In this embodiment, although a suitable Counter Threshold may be set to 10, it may be some other empirically determined value. For example, in some embodiments of the methodology, the counter threshold may be set as a result of processing based on machine learning and pattern recognition techniques. Such techniques may include cluster analysis, support vector machines and Bayesian classification or other similar machine learning techniques.

O. Sleep Onset Module

Detecting sleep onset accurately can provide a very interesting insight into the patient's sleeping patterns and overall quality of sleep. It can also be important in accurately detecting sleep state. Thus, in some embodiments of the sleep condition detection device 102, an index may be implemented to detect or calculate the first transition into sleep from awake in a particular sleep session. The transition to sleep may be either NREM Sleep or NREM Sleep T, which may depend on which state has a higher transition probability in the implementation discussed below. Subsequent transitions into sleep states may then be governed by sleep state modules previously discussed herein.

In the example implementation, the sleep onset detection module may utilize as input data representing one or more respiratory flow based features taken from the feature extractor 110. For example, sleep onset detection may be implemented by analysis of the following set of features:

1.) EPFL Ratio—This feature is the ratio between Expiratory Peak Flow Location and Total Expiratory Period, which may optionally be defined in samples (e.g., number of samples) rather than time units (e.g., seconds)).

2.) EPFL Difference Feature—This feature takes the current EPFL Ratio and subtracts the average EPFL Ratio over a set period of time. For example, the set period of time may be a previous number of breaths in a range from 10 to 20 but preferably 15.

Sleep onset detection may also be based on the following:

3.) Raw Sleep State Score—This may be a score output from the sleep state detector as previously discussed for a sleep state.

The sleep onset detector may then be implemented with the following processing methodology in the detection of sleep onset based on the above mentioned input data. This may be determined on a breath-by-breath basis at least until the patient has transitioned into the sleep onset:

1.) Derive a Sleep-Awake Transition Index (which may be preset to 0):
  If (EPFL Difference Feature>=T1) OR (Raw Sleep State Score>=T2) THEN (Increment Sleep-Awake Transition Index by 1)

2.) IF (Sleep-Awake Transition Index>=T3) THEN Sleep Onset=1 (i.e., This Sleep Onset Index may be taken to represent that the person using the sleep condition detection module has transitioned into a first sleep period for the night).

In these embodiments, the T1, T2 and T3 thresholds may be determined empirically with known data for a group of patients. It may also be determined and set in a device for a particular patient.

Accordingly, the Sleep Onset Index may be considered a binary switch or flag that is preset (e.g., to 0), such as at startup, to represent that the first onset of sleep has not occurred. In the example, if the index is subsequently set to 1, then the person using the detector is considered to be in sleep (e.g., the first onset of sleep for a sleep session (e.g. a night)). Otherwise, the patient may be considered to be in an awake state (e.g., not yet in an initial sleep state for the particular session using the detector). In this way, the device may be configured to distinguish the onset of sleep (the initial transition to sleep) from subsequent transitions to sleep of a common or particular treatment session having multiple transitions from an awake state into a sleep state.

P. Respiratory Treatment Device

Figure 11:
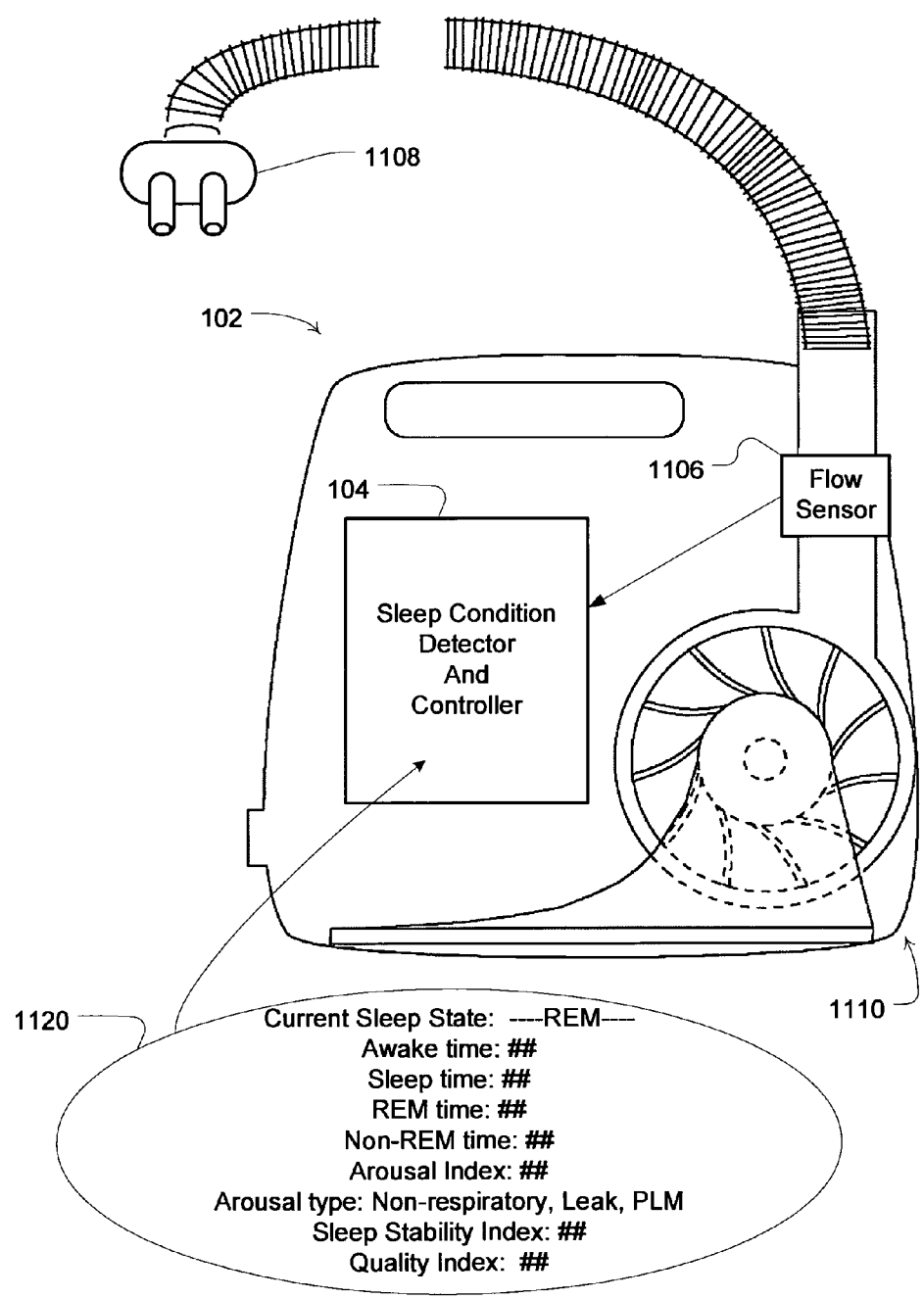
FIG. 11 shows an example sleep condition detection apparatus of the present technology.

Although the controller may be implemented without feedback, in a monitoring type device or data analysis device, some embodiments as previously discussed may implement the controller with a flow generator. For example, as illustrated in FIG. 11, the sleep condition detection device may be optionally implemented with a flow generator 1110 such as a servo controlled blower with suitable sensors for such control (e.g., a pressure sensor and/or flow sensor 1106).

A respiratory treatment or pressure therapy regime, such as a therapeutic pressure level associated with CPAP treatment, may be delivered by the controller of the device. Such therapeutic pressure levels may be automatically adjusted in response to the detection of sleep conditions as previously described herein that may be suitable for treatment of patients with Sleep Disorder Breathing (SDB). Other pressure adjustment schemes may also be implemented. Pressure may be delivered to a patient via a patient interface 1108 such as a mask, cannula and supply tube.

In this embodiment, the display 1120 is mounted on an exterior surface of the housing of the sleep condition detection device 102. As illustrated in this embodiment, the controller 104 may then be housed within the same housing as display. Output from the modules of the device may then optionally be displayed to the user or clinician on a display 1120 of the device or otherwise transferred from a memory of the device to other devices, systems or computers. Thus, the controller may then also optionally be configured to communicate with other external equipment including, for example, over the Internet with other computer based systems via a wired communications port (e.g., an Ethernet communications card and connection) (not shown) or a wireless communications port (e.g., a Bluetooth transceiver) (not shown).

Q. Example Controller Architecture

Figure 12:
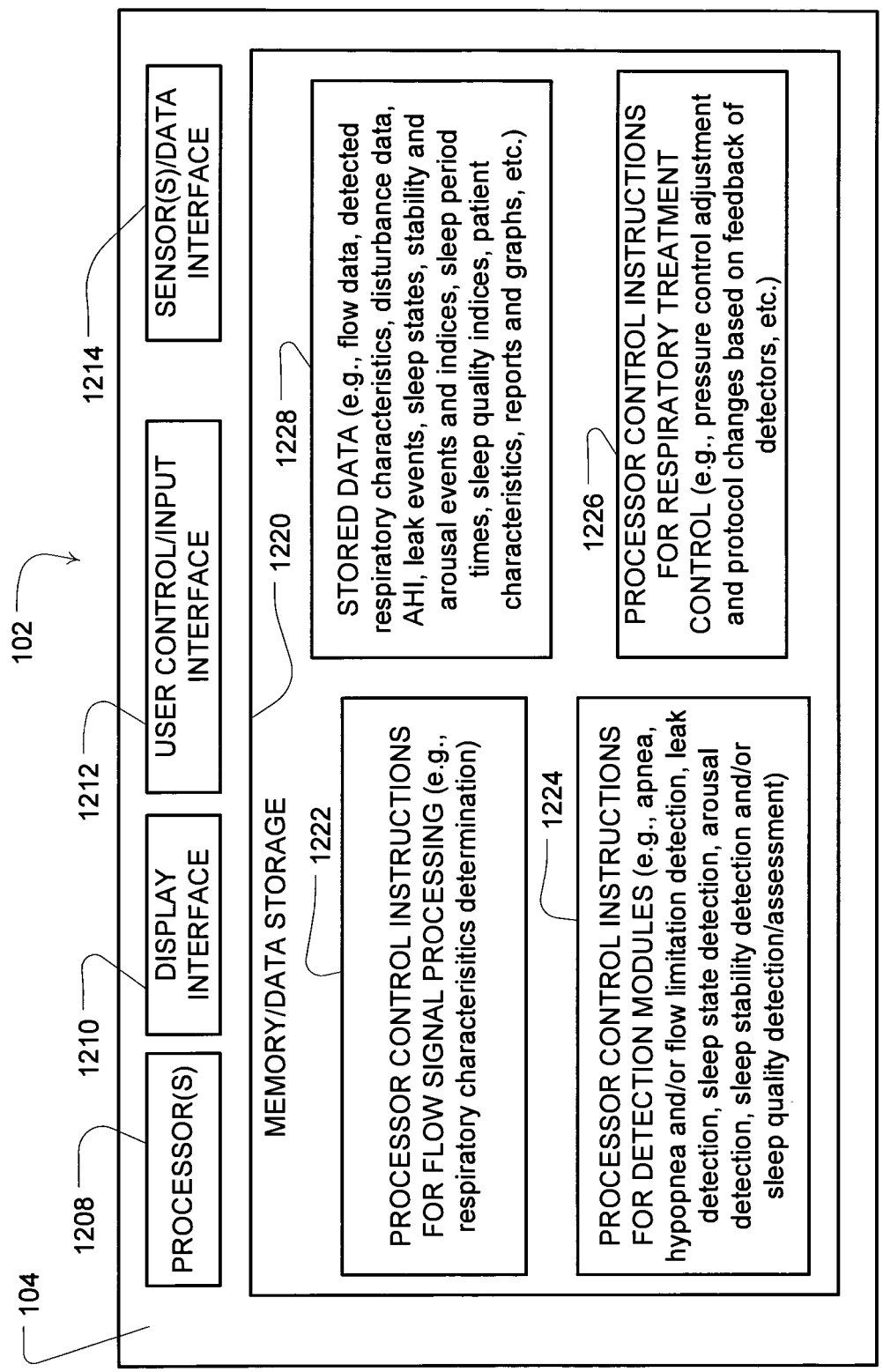
FIG. 12 is a block diagram of a controller in a hypopnea detection apparatus including example components thereof suitable for implementing the detection methodologies of the present technology.

An example system architecture of a controller 104 is illustrated in the block diagram of FIG. 12. In the illustration, a sleep condition detection device 102 may be implemented by a general purpose computer with one or more programmable processors 1208. The device may also include a display interface 1210 to output data from the modules as previously discussed (e.g., sleep states, durations, sleep quality indices, AHI, leak detection data, and/or stability indices, etc.), results or graphs as described herein to a display such as on a monitor or LCD panel. A user control/input interface 1214, for example, for a keyboard, touch panel, control buttons, mouse etc. may also be included as previously discussed and for adjusting a therapy of a flow generator, inputting data, or otherwise activating or operating the methodologies described herein. The device may also include a sensor or data interface 1214, such as a bus, for receiving/transmitting data such as programming instructions, flow data, pressure data, sleep quality data, sleep state data, sleep stability data, arousal data and other output or input of the previously described modules.

The device also includes memory/data storage components 1220 containing control instructions and data of the aforementioned methodologies and modules. For example, at 1222, they may include stored processor control instructions for flow signal processing such as measuring and/or feature extraction. At 1224, these may also include stored processor control instructions for flow limitation detection, AHI detection, leak detection, arousal detection, sleep state detection, sleep stability detection and/or sleep quality detection as discussed in more detail herein. At 1226, they may also include processor control instructions for respiratory treatment control such as feedback processing and pressure control adjustment, etc. Finally, they may also include stored data at 1228 for these methodologies such as flow data, detected respiratory characteristics, disturbance data, detected hypopnea and apnea events (AHI), sleep states, stability and arousal events and indices, sleep period times, sleep quality indices, patient characteristics, reports and graphs, etc.

In some embodiments, the processor control instructions and data for controlling the above described methodologies may be contained in a computer readable recording medium as software for use by a general purpose computer so that the general purpose computer may serve as a specific purpose computer according to any of the methodologies discussed herein upon loading the software into the general purpose computer.

In the foregoing description and in the accompanying drawings, specific terminology, equations and drawing symbols are set forth to provide a thorough understanding of the present technology. In some instances, the terminology and symbols may imply specific details that are not required to practice the technology. For example, although process steps in the detection methodologies have been illustrated in the figures in an order and with reference to particularly discrete modules, such an ordering and modularization is not required. Those skilled in the art will recognize that such ordering may be modified and/or aspects thereof may be conducted in parallel. Those skilled in the art will also recognize that some aspects of certain modules may be combined with some aspects of other modules to implement discrete features of the technology. Furthermore, although an entire system has been described with particular reference to the embodiment of FIG. 1, the distinct features may separately, or in different combinations, be implemented in other respiratory treatment and/or monitoring systems. Moreover, although tables with particular values and thresholds are illustrated, it will be understood that other values may be utilized, which may be determined from empirical data and/or machine learning.

Thus, although the technology herein has been described with reference to particular embodiments, it is to be understood that these embodiments are merely illustrative of the principles and applications of the technology. It is therefore to be understood that numerous modifications may be made to the illustrative embodiments and that other arrangements may be devised without departing from the spirit and scope of the technology.

The invention claimed is:

1. A method for controlling a processor to detect a sleep state from a measured flow of breathable gas, the method of the processor comprising:
   determining a plurality of respiratory characteristics from a measure of respiratory flow;
   detecting a sleep state from potential sleep states comprising a Non-REM sleep state and a REM sleep state, the detecting of the sleep state based on the determined respiratory characteristics, the detection of the sleep state based on data from the measure of flow from a flow sensor, the detecting of the sleep state not being based on data from electroencephalogram (E.E.G.), electromyography (E.M.G.) and electrooculography (E.O.G.) sensors; and
   indicating the detected sleep state,
   wherein the determined plurality of respiratory characteristics from which the sleep state is detected includes a set of two or more measures of (a) a measure of expiratory peak flow variation derived from a plurality of breaths, (b) a measure of a ratio of an expiratory peak flow location and expiratory time, (c) a measure of an expiratory peak flow location variation derived from a plurality of breaths, (d) a measure of an area of an expiratory peak flow, (e) a measure of an area of an expiratory peak flow variation, (f) a measure of a time from expiratory peak flow to inspiration start, (g) a measure of a time since last confirmed breath variability, (h) a measure of a high breath frequency period, and (i) a measure of inspiratory time variability.

2. The method of claim 1 wherein the potential sleep states further comprises an awake state.

3. The method of claim 2 wherein the REM sleep state is a light REM state and the potential sleep states further comprises a deep REM state.

4. The method of claim 1 wherein the processor determines a next sleep state as the detected sleep state by calculating probabilities representative of transitions from a current sleep state to each potential next sleep state with data from the plurality of respiratory characteristics, in which the next sleep state is of the potential sleep states which include the current sleep state, and determines the detected sleep state as a function of a most probable one of the calculated probabilities.

5. The method of claim 1 wherein the plurality of respiratory characteristics from which the sleep state is detected includes a measure of inspiratory peak flow variation.

6. The method of claim 1 wherein the plurality of respiratory characteristics from which the sleep state is detected includes a measure of expiratory peak flow variation derived from a plurality of breaths.

7. The method of claim 1 wherein the plurality of respiratory characteristics from which the sleep state is detected includes a measure of a ratio of an expiratory peak flow location and expiratory time.

8. The method of claim 1 wherein the plurality of respiratory characteristics from which the sleep state is detected includes a measure of an expiratory peak flow location variation derived from a plurality of breaths.

9. The method of claim 1 wherein the plurality of respiratory characteristics from which the sleep state is detected includes a measure of an area of an expiratory peak flow.

10. The method of claim 1 wherein the plurality of respiratory characteristics from which the sleep state is detected includes a measure of an area of an expiratory peak flow variation.

11. The method of claim 1 wherein the plurality of respiratory characteristics from which the sleep state is detected includes a measure of a time from expiratory peak flow to inspiration start.

12. The method of claim 1 wherein the plurality of respiratory characteristics from which the sleep state is detected includes a measure of a time since last confirmed breath variability.

13. The method of claim 1 wherein the plurality of respiratory characteristics from which the sleep state is detected includes a measure of a high breath frequency period.

14. The method of claim 1 wherein the plurality of respiratory characteristics from which the sleep state is detected includes a measure of inspiratory time variability.

15. The method of claim 1 wherein processer further controls a respiratory pressure treatment regime based on the detected sleep state.

16. A sleep state detection apparatus comprising:
a controller having at least one processor to access data representing a measured flow of breathable gas, the controller being further configured to:
  determine a plurality of respiratory characteristics from a measure of respiratory flow based on the accessed data;
  detect a sleep state from potential sleep states comprising a Non-REM sleep state and a REM sleep state, the detecting of the sleep state based on the determined respiratory characteristics, the detecting of the sleep state based on data from the measure of flow from a flow sensor, the detecting of the sleep state not being based on data from electroencephalogram (E.E.G.), electromyography (E.M.G.) and electrooculography (E.O.G.) sensors; and
  indicate the detected sleep state,
wherein the determined plurality of respiratory characteristics from which the sleep state is detected includes a set of two or more measures of (a) a measure of expiratory peak flow variation derived from a plurality of breaths, (b) a measure of a ratio of an expiratory peak flow location and expiratory time, (c) a measure of an expiratory peak flow location variation derived from a plurality of breaths, (d) a measure of an area of an expiratory peak flow, (e) a measure of an area of an expiratory peak flow variation, (f) a measure of a time from expiratory peak flow to inspiration start, (g) a measure of a time since last confirmed breath variability, (h) a measure of a high breath frequency period, and (i) a measure of inspiratory time variability.

17. The sleep state detection apparatus of claim 16 wherein the potential sleep states further comprises an awake state.

18. The sleep state detection apparatus of claim 17 wherein the REM sleep state is a light REM state and the potential sleep states further comprises a deep REM state.

19. The sleep state detection apparatus of claim 16 wherein the processor determines a next sleep state as the detected sleep state by calculating probabilities representative of transitions from a current sleep state to each potential next sleep state with data from the plurality of respiratory characteristics, in which the next sleep state is of the potential sleep states which include the current sleep state, and determines the detected sleep state as a function of a most probable one of the calculated probabilities.

20. The sleep state detection apparatus of claim 16 wherein the plurality of respiratory characteristics from which the sleep state is detected includes a measure of inspiratory peak flow variation.

21. The sleep state detection apparatus of claim 16 wherein the plurality of respiratory characteristics from which the sleep state is detected includes a measure of expiratory peak flow variation derived from a plurality of breaths.

22. The sleep state detection apparatus of claim 16 wherein the plurality of respiratory characteristics from which the sleep state is detected includes a measure of a ratio of an expiratory peak flow location and expiratory time.

23. The sleep state detection apparatus of claim 16 wherein the plurality of respiratory characteristics from which the sleep state is detected includes a measure of an expiratory peak flow location variation derived from a plurality of breaths.

24. The sleep state detection apparatus of claim 16 wherein the plurality of respiratory characteristics from which the sleep state is detected includes a measure of an area of an expiratory peak flow.

25. The sleep state detection apparatus of claim 16 wherein the plurality of respiratory characteristics from which the sleep state is detected includes a measure of an area of an expiratory peak flow variation.

26. The sleep state detection apparatus of claim 16 wherein the plurality of respiratory characteristics from which the sleep state is detected includes a measure of a time from expiratory peak flow to inspiration start.

27. The sleep state detection apparatus of claim 16 wherein the plurality of respiratory characteristics from which the sleep state is detected includes a measure of a time since last confirmed breath variability.

28. The sleep state detection apparatus of claim 16 wherein the plurality of respiratory characteristics from which the sleep state is detected includes a measure of a high breath frequency period.

29. The sleep state detection apparatus of claim 16 wherein the plurality of respiratory characteristics from which the sleep state is detected includes a measure of inspiratory time variability.

30. The sleep state detection apparatus of claim 16 further comprising the flow sensor to measure the flow of breathable gas, and wherein the apparatus further comprises a processor controlled flow generator, wherein the controller is configured to control the flow generator to provide a respiratory pressure treatment regime based on the detected sleep state.

31. A sleep state detection system comprising:
   means for accessing data representing a measured flow of breathable gas, and for determining a plurality of respiratory characteristics from a measure of respiratory flow based on the accessed data;
   means for detecting a sleep state from potential sleep states comprising a Non-REM sleep state and a REM sleep state, the detecting of the sleep state based on the determined respiratory characteristics, the detecting of the sleep state being based on data from the measure of flow from a flow sensor, the detecting of the sleep state not being based on data from electroencephalogram (E.E.G.), electromyography (E.M.G.) and electrooculography (E.O.G.) sensors; and
   means for indicating the detected sleep state,
   wherein the determined plurality of respiratory characteristics from which the sleep state is detected includes a set of two or more measures of (a) a measure of expiratory peak flow variation derived from a plurality of breaths, (b) a measure of a ratio of an expiratory peak flow location and expiratory time, (c) a measure of an expiratory peak flow location variation derived from a plurality of breaths, (d) a measure of an area of an expiratory peak flow, (e) a measure of an area of an expiratory peak flow variation, (f) a measure of a time from expiratory peak flow to inspiration start, (g) a measure of a time since last confirmed breath variability, (h) a measure of a high breath frequency period, and (i) a measure of inspiratory time variability.

32. The sleep state detection system of claim 31 further comprising the flow sensor for measuring a flow of breathable gas.

33. The sleep state detection system of claim 32 further comprising flow generation means for generating a flow of breathable gas based on the detected sleep state.

* * * * *